(12) United States Patent
Ju et al.

(10) Patent No.: US 8,298,792 B2
(45) Date of Patent: *Oct. 30, 2012

(54) FOUR-COLOR DNA SEQUENCING BY SYNTHESIS USING CLEAVABLE FLUORESCENT NUCLEOTIDE REVERSIBLE TERMINATORS

(75) Inventors: Jingyue Ju, Englewood Cliffs, NJ (US);
Dae Hyun Kim, New York, NY (US);
Lanrong Bi, New York, NY (US);
Qinglin Meng, New York, NY (US);
Xiaoxu Li, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/023,283

(22) Filed: Feb. 8, 2011

(65) Prior Publication Data

US 2012/0021408 A1    Jan. 26, 2012

Related U.S. Application Data

(63) Continuation of application No. 12/312,903, filed as application No. PCT/US2007/024646 on Nov. 30, 2007, now Pat. No. 7,883,869.

(60) Provisional application No. 60/872,240, filed on Dec. 1, 2006.

(51) Int. Cl.
*C12P 19/34*    (2006.01)
*C12Q 1/68*    (2006.01)
*B01L 3/00*    (2006.01)
*C07H 21/00*    (2006.01)
*C07H 21/02*    (2006.01)

(52) U.S. Cl. ............ 435/91.1; 435/6; 435/91.2; 536/4.1; 536/23.1; 536/24.3; 536/24.33; 536/25.3; 536/26.6; 422/430

(58) Field of Classification Search .................. 435/6.1, 435/91.1, 91.2; 536/4.1, 23.1, 24.3, 24.33, 536/25.3, 26.6; 422/430
See application file for complete search history.

(56) References Cited

U.S. PATENT DOCUMENTS

| | | | |
|---|---|---|---|
| 4,711,955 | A | 12/1987 | Ward et al. |
| 4,772,691 | A | 9/1988 | Herman |
| 4,824,775 | A | 4/1989 | Dattagupta et al. |
| 4,863,849 | A | 9/1989 | Melamede |
| 5,043,272 | A | 8/1991 | Hartley |
| 5,118,605 | A | 6/1992 | Urdea |
| 5,174,962 | A | 12/1992 | Brennan |
| 5,175,269 | A | 12/1992 | Stavrianopoulos et al. |
| 5,302,509 | A | 4/1994 | Cheeseman |

(Continued)

FOREIGN PATENT DOCUMENTS

DE    4141178    6/1993

(Continued)

OTHER PUBLICATIONS

Stratagene Catalog, 1988, p. 39.*

(Continued)

*Primary Examiner* — Jezia Riley
(74) *Attorney, Agent, or Firm* — John P. White; Cooper & Dunham LLP

(57) ABSTRACT

This invention provides a process for sequencing single-stranded DNA employing modified nucleotides.

20 Claims, 14 Drawing Sheets

U.S. PATENT DOCUMENTS

| | | | |
|---|---|---|---|
| 5,308,990 A | 5/1994 | Takahashi | |
| 5,328,824 A | 7/1994 | Ward et al. | |
| 5,332,666 A | 7/1994 | Prober et al. | |
| 5,436,143 A | 7/1995 | Hyman | |
| 5,437,975 A | 8/1995 | McClelland et al. | |
| 5,449,767 A | 9/1995 | Ward et al. | |
| 5,476,928 A | 12/1995 | Ward et al. | |
| 5,516,664 A | 5/1996 | Hyman | |
| 5,534,424 A | 7/1996 | Uhlen | |
| 5,547,839 A | 8/1996 | Dower | |
| 5,547,859 A | 8/1996 | Goodman | |
| 5,556,748 A | 9/1996 | Douglas | |
| 5,599,675 A | 2/1997 | Brenner | |
| 5,602,000 A | 2/1997 | Hyman | |
| 5,637,469 A | 6/1997 | Wilding et al. | |
| 5,654,419 A | 8/1997 | Mathies | |
| 5,658,736 A | 8/1997 | Wong | |
| 5,709,999 A | 1/1998 | Shattuck et al. | |
| 5,728,528 A | 3/1998 | Mathies | |
| 5,763,594 A | 6/1998 | Hiatt et al. | |
| 5,770,365 A | 6/1998 | Lane et al. | |
| 5,770,367 A | 6/1998 | Southern et al. | |
| 5,789,167 A | 8/1998 | Konrad | |
| 5,798,210 A | 8/1998 | Canard et al. | |
| 5,804,386 A | 9/1998 | Ju | |
| 5,808,045 A | 9/1998 | Hiatt et al. | |
| 5,814,454 A | 9/1998 | Ju | |
| 5,821,356 A | 10/1998 | Khan et al. | |
| 5,834,203 A | 11/1998 | Katzir | |
| 5,849,542 A | 12/1998 | Reeve et al. | |
| 5,853,992 A | 12/1998 | Glazer | |
| 5,856,104 A | 1/1999 | Chee et al. | |
| 5,869,255 A | 2/1999 | Mathies | |
| 5,872,244 A | 2/1999 | Hiatt et al. | |
| 5,876,936 A | 3/1999 | Ju | |
| 5,885,775 A | 3/1999 | Haff et al. | |
| 5,908,755 A | 6/1999 | Kumar et al. | |
| 5,945,283 A | 8/1999 | Kwok | |
| 5,952,180 A | 9/1999 | Ju | |
| 5,962,228 A | 10/1999 | Brenner | |
| 6,001,566 A | 12/1999 | Canard et al. | |
| 6,001,611 A | 12/1999 | Will | |
| 6,008,379 A | 12/1999 | Benson et al. | |
| 6,028,190 A | 2/2000 | Mathies | |
| 6,046,005 A | 4/2000 | Ju | |
| 6,074,823 A | 6/2000 | Koster | |
| 6,087,095 A | 7/2000 | Rosenthal et al. | |
| 6,136,543 A | 10/2000 | Anazawa | |
| 6,175,107 B1 | 1/2001 | Juvinall | |
| 6,197,557 B1 | 3/2001 | Markarov | |
| 6,207,831 B1 | 3/2001 | Auer et al. | |
| 6,210,891 B1 | 4/2001 | Nyren | |
| 6,214,987 B1 | 4/2001 | Hiatt | |
| 6,218,118 B1 | 4/2001 | Sampson | |
| 6,218,530 B1 | 4/2001 | Rothschild | |
| 6,221,592 B1 | 4/2001 | Schwartz | |
| 6,232,465 B1 | 5/2001 | Hiatt et al. | |
| 6,242,193 B1 | 6/2001 | Anazawa et al. | |
| 6,245,507 B1 | 6/2001 | Bogdanov | |
| 6,255,475 B1 | 7/2001 | Kwiatkowski | |
| 6,274,320 B1 | 8/2001 | Rothberg et al. | |
| 6,277,607 B1 | 8/2001 | Tyagi et al. | |
| 6,287,821 B1 | 9/2001 | Shi et al. | |
| 6,294,324 B1 | 9/2001 | Bensimon et al. | |
| 6,309,829 B1 | 10/2001 | Livak et al. | |
| 6,309,836 B1 | 10/2001 | Kwiatkowski | |
| 6,312,893 B1 | 11/2001 | Van Ness et al. | |
| 6,316,230 B1 | 11/2001 | Egholm | |
| 6,361,940 B1 | 3/2002 | Van Ness et al. | |
| 6,380,378 B1 | 4/2002 | Kitamura et al. | |
| 6,524,829 B1 | 2/2003 | Seeger | |
| 6,555,349 B1 | 4/2003 | O'Donnell | |
| 6,613,508 B1 | 9/2003 | Ness et al. | |
| 6,613,513 B1 | 9/2003 | Parce et al. | |
| 6,627,748 B1 | 9/2003 | Ju et al. | |
| 6,632,655 B1 | 10/2003 | Mehta et al. | |
| 6,639,088 B2 | 10/2003 | Kwiatkowski | |
| 6,664,079 B2 | 12/2003 | Ju et al. | |
| 6,664,399 B1 | 12/2003 | Sabesan | |
| 6,713,255 B1 | 3/2004 | Makino et al. | |
| 6,780,591 B2 | 8/2004 | Williams et al. | |
| 6,787,308 B2 | 9/2004 | Balasubramanian et al. | |
| 6,818,395 B1 | 11/2004 | Quake et al. | |
| 6,833,246 B2 | 12/2004 | Balasubramanian et al. | |
| 6,864,052 B1 | 3/2005 | Drmanac et al. | |
| 6,911,345 B2 | 6/2005 | Quake et al. | |
| 6,934,636 B1 | 8/2005 | Skierczynski et al. | |
| 6,982,146 B1 | 1/2006 | Schneider et al. | |
| 7,037,687 B2 | 5/2006 | Williams et al. | |
| 7,056,661 B2 | 6/2006 | Korlach et al. | |
| 7,056,666 B2 | 6/2006 | Dower et al. | |
| 7,057,026 B2 | 6/2006 | Barnes et al. | |
| 7,057,031 B2 | 6/2006 | Olejnik et al. | |
| 7,074,597 B2 | 7/2006 | Ju | |
| 7,078,499 B2 | 7/2006 | Odedra et al. | |
| 7,105,300 B2 | 9/2006 | Parce et al. | |
| 7,329,496 B2 | 2/2008 | Dower et al. | |
| 7,345,159 B2 | 3/2008 | Ju et al. | |
| 7,414,116 B2 | 8/2008 | Milton et al. | |
| 7,427,673 B2 | 9/2008 | Balasubramanian et al. | |
| 7,459,275 B2 | 12/2008 | Dower et al. | |
| 7,566,537 B2 | 7/2009 | Balasubramanian et al. | |
| 7,622,279 B2 | 11/2009 | Ju | |
| 7,635,578 B2 | 12/2009 | Ju et al. | |
| 7,713,698 B2 | 5/2010 | Ju et al. | |
| 7,883,869 B2 * | 2/2011 | Ju et al. | 435/91.1 |
| 2002/0012966 A1 | 1/2002 | Shi et al. | |
| 2002/0168642 A1 | 11/2002 | Drukier | |
| 2003/0008285 A1 | 1/2003 | Fischer | |
| 2003/0022225 A1 | 1/2003 | Monforte | |
| 2003/0027140 A1 | 2/2003 | Ju et al. | |
| 2003/0044871 A1 | 3/2003 | Cutsforth et al. | |
| 2003/0054360 A1 | 3/2003 | Gold et al. | |
| 2003/0099972 A1 | 5/2003 | Olejnik et al. | |
| 2003/0166282 A1 | 9/2003 | Brown et al. | |
| 2003/0186256 A1 | 10/2003 | Fischer | |
| 2003/0190680 A1 | 10/2003 | Rothschild et al. | |
| 2003/0198982 A1 | 10/2003 | Seela et al. | |
| 2004/0014096 A1 | 1/2004 | Anderson et al. | |
| 2004/0096825 A1 | 5/2004 | Chenna et al. | |
| 2004/0185466 A1 | 9/2004 | Ju et al. | |
| 2005/0032081 A1 | 2/2005 | Ju et al. | |
| 2005/0239134 A1 | 10/2005 | Gorenstein et al. | |
| 2006/0003352 A1 | 1/2006 | Ju et al. | |
| 2006/0057565 A1 | 3/2006 | Ju et al. | |
| 2006/0105461 A1 | 5/2006 | Tom-Moy et al. | |
| 2006/0240439 A1 | 10/2006 | Smith et al. | |
| 2006/0252038 A1 | 11/2006 | Ju et al. | |
| 2007/0166705 A1 | 7/2007 | Milton et al. | |
| 2007/0275387 A1 | 11/2007 | Ju | |
| 2008/0131895 A1 | 6/2008 | Ju et al. | |
| 2008/0199868 A1 | 8/2008 | Ju et al. | |
| 2008/0319179 A1 | 12/2008 | Ju et al. | |
| 2009/0088332 A1 | 4/2009 | Ju et al. | |

FOREIGN PATENT DOCUMENTS

| | | |
|---|---|---|
| EP | 0995804 | 4/2000 |
| EP | 1182267 | 2/2002 |
| EP | 1291354 | 3/2003 |
| EP | 0808320 | 4/2003 |
| EP | 1337541 | 3/2007 |
| EP | 1218391 | 4/2007 |
| EP | 1790736 | 5/2007 |
| EP | 0992511 | 3/2009 |
| WO | WO 89/09282 | 10/1989 |
| WO | WO 90/13666 | 11/1990 |
| WO | WO 91/06678 | 5/1991 |
| WO | WO 92/10587 | 6/1992 |
| WO | WO 93/05183 | 3/1993 |
| WO | WO 93/21340 | 10/1993 |
| WO | WO 94/14972 | 7/1994 |
| WO | WO 96/07669 | 3/1996 |
| WO | WO 96/23807 | 8/1996 |
| WO | WO 96/27025 | 9/1996 |
| WO | WO 97/08183 | 3/1997 |
| WO | WO 97/27317 | 7/1997 |
| WO | WO 97/35033 | 9/1997 |

| | | |
|---|---|---|
| WO | WO 98/30720 | 7/1998 |
| WO | WO 98/44151 | 10/1998 |
| WO | WO 99/05315 | 2/1999 |
| WO | WO 99/57321 | 11/1999 |
| WO | WO 00/02895 | 1/2000 |
| WO | WO 00/06770 | 2/2000 |
| WO | WO 00/09753 | 2/2000 |
| WO | WO 00/15844 | 3/2000 |
| WO | WO 00/18956 | 4/2000 |
| WO | WO 00/21974 | 4/2000 |
| WO | WO 00/50172 | 8/2000 |
| WO | WO 00/50642 | 8/2000 |
| WO | WO 00/53805 | 9/2000 |
| WO | WO 00/53812 | 9/2000 |
| WO | WO 00/70073 | 11/2000 |
| WO | 01/16375 | 3/2001 |
| WO | WO 01/23610 | 4/2001 |
| WO | WO 01/25247 | 4/2001 |
| WO | WO 01/27625 | 4/2001 |
| WO | WO 01/32930 | 5/2001 |
| WO | WO 01/57248 | 8/2001 |
| WO | WO 01/57249 | 8/2001 |
| WO | WO 01/92284 | 12/2001 |
| WO | WO 02/02813 | 1/2002 |
| WO | WO 02/22883 | 3/2002 |
| WO | WO 02/29003 | 4/2002 |
| WO | WO 02/072892 | 9/2002 |
| WO | WO 02/079519 | 10/2002 |
| WO | WO 02/088381 | 11/2002 |
| WO | WO 02/088382 | 11/2002 |
| WO | WO 03/002767 | 1/2003 |
| WO | WO 03/020968 | 3/2003 |
| WO | WO 03/048178 | 6/2003 |
| WO | WO 03/048387 | 6/2003 |
| WO | WO 03/085135 | 10/2003 |
| WO | WO 2004/007773 | 1/2004 |
| WO | WO 2004/055160 | 1/2004 |
| WO | WO 2004/018493 | 3/2004 |
| WO | WO 2004/018497 | 3/2004 |
| WO | WO 2005/084367 | 9/2005 |
| WO | WO 2006/073436 | 7/2006 |
| WO | WO 2007/002204 | 1/2007 |
| WO | WO 2007/053702 | 5/2007 |
| WO | WO 2007/053719 | 5/2007 |
| WO | WO 2007/062105 | 5/2007 |
| WO | WO 2008/069973 | 6/2008 |

OTHER PUBLICATIONS

Notice of Allowance issued Feb. 24, 2009 in connection with U.S. Appl. No. 11/894,690.

Notice of Allowance issued Mar. 23, 2009 in connection with U.S. Appl. No. 11/894,808.

Notification Concerning Transmittal of International Preliminary Report on Patentability issued Jun. 11, 2009 in connection with International Application No. PCT/US07/024646.

Collins, F. S.; Morgan, M.; Patrinos, A. (2003) "The Human Genome Project: Lessons from Large-Scale Biology." Science, 300, pp. 286-290.

Prober JM, Trainor GL, Dam RJ, Hobbs FW, Robertson CW, Zagursky RJ, Cocuzza AJ, Jensen MA, Baumeister K. (1987) "A system for rapid DNA sequencing with fluorescent chain-terminating dideoxynucleotides". Science 238: 336-341.

Ju J., Ruan C., Fuller, C.W., Glazer, A.N., and Mathies, R.A. (1995) Fluorescence energy transfer dye-labeled primers for DNA sequencing and analysis. Proc. Natl. Acad. Sci. USA 92: 4347-4351.

Kan, C.-W.; Doherty, E. A. S.; Barron, A. E. (2003) "A novel thermogelling matrix for microchannel DNA sequencing based on poly-N-alkoxyalkylacrylamide copolymers." Electrophoresis, 24, pp. 4161-4169.

Drmanac, S.; Kita, D.; Labat, I.; et al. (1998) "Accurate sequencing by hybridization for DNA diagnostics and individual genomics." Nat. Biotech., 16, pp. 54-58.

Fu, D.J., Tang, K., Braun, A., Reuter, D., Darnhofer-Demar, B., Little, D.P., O'Donnell, M.J., Cantor, C.R., and Koster, H. (1998) "Sequencing exons 5 to 8 of the p53 gene by MALDI-TOF mass spectrometry." Nat. Biotechnol. 16:381-384.

Roskey, M.T, Juhasz, P., Smirnov, I.P., Takach, E.J., Martin, S.A., and Haff, L.A. (1996) "DNA sequencing by delayed extraction-matrix-assisted laser desorption/ionization time of flight mass spectrometry." Proc. Natl. Acad. Sci. USA. 93:4724-4729.

Edwards, J. at al. (2001) DNA sequencing using biotinylated dideoxynucleotides and mass spectrometry. Nucleic Acids Res., 29(21), pp. 1041-1046.

Kasianowicz, J.J., Brandin, B., Branton, D. and Deamer, D.W. Characterization of individual polynucleotide molecules using a membrane channel. Proc. Natl. Acad. Sci. USA 1996, 93, 13770-13773.

Shendure, J.; Porreca, G. J.; Reppas, N.B.; et al. (2005) "Accurate Multiplex Polony Sequencing of an Evolved Bacterial Genome." Science, 309, pp. 1728-1732.

Ronaghi M, Uhlen M, Nyren P. (1998) "A sequencing Method based on real-time pyrophosphate". Science 281; 364-365.

Braslaysky, I.; Hebert, B.; Kartalov, E.; et al. (2003) "Sequence information can be obtained from single DNA molecules." Proc. Natl. Acad. Sci., 100 (7), pp. 3960-3964.

Mitre, R. D.; Shendure J.; Olejnik, J.; et al. (2003) "Fluorescent in situ sequencing on polymerase colonies." Anal. Biochem., 320, pp. 55-65.

Hyman ED, (1988) "A new method of sequencing DNA". Analytical Biochemistry 174: 423-436.

Margulies, M.; Egholm, M.; Altman, W. E.; at al. (2005) "Genome sequencing in microfabricated high-density picolitre reactors." Nature, 437, pp. 376-380.

Metzker ML, Raghavachari R, Richards S, Jacutin SE, Civitello A, Burgess K, Gibbs RA. (1994) "Termination of DNA synthesis by novel 3' modified deoxyribonucleoside 5' triphosphates". Nucleic Acids Res. 22; 4259-4267.

Welch MB, Burgess K, (1999) "Synthesis of fluorescent, photolabile 3'-O-protected nucleoside triphosphates for the base addition sequencing scheme". Nucleosides and Nucleotides 18:197-201.

Lu, G. and Burgess, K. (2006) "A diversity oriented synthesis of 3'-O-modified nucleoside triphosphates for DNA 'sequencing by synthesis'" Bioorg. Med. Chem. Lett., 16, pp. 3902-3905.

Metzker M. L. (2005) "Emerging technologies in DNA sequencing." Genome Res., 15, pp. 1767-1776.

Pelletier H, Sawaya MR, Kumar A, Wilson SH, Kraut J. (1994) "Structures of ternary complexes of rat DNA polymerase β, a DNA template-primer, and ddCTP". Science 264: 1891-1903.

Rosenblum, B.B. et al. (1997) "New dye-labeled terminators for improved DNA sequencing patterns". Nucleic Acids Res. 25: 4500-4504.

Seo et al., (2005) "Four-Color DNA Sequencing by Synthesis on a Chip Using Photocleavable Fluorescent Nucleotides" PNAS 102(17) :5926-5931.

Bi, L.; Kim D. H.; and Ju, J. (2006) "Design and Synthesis of a Chemically Cleavable Fluorescent Nucleotide, 3'-O-Allyl-dGTP-allyl-Bodipy-FL-510, as a Reversible Terminator for DNA Sequencing by Synthesis" J. Am. Chem. Soc., 128, pp. 2542-2543.

Ruparel et al., (2005) "Design and Synthesis of a 3'-O-Allyl Photocleavable Fluorescent Nucleotide as a Reversible Terminator for DNA Sequencing by Synthesis" PNAS, 102(17):5932-5937.

Meng et al., (2006) "Design and Synthesis of a Photocleavable Fluorescent Nucleotide 3'-O-Allyl-dGTP-PC-Biodipy-FL-510 as a Reversible Terminator for DNA Sequencing by Synthesis" J. Org. Chem 71:3248-3252.

Jingyue Ju, et al. (1996) Cassette labeling for facile construction of energy transfer fluorescent primers. Nucleic Acids Res. 24(6):1144-1148.

Ju J., Glazer, A.N., and Mathies, R.A. (1996) Energy transfer primers: A new fluorescence labeling paradigm for DNA sequencing and analysis. Nature Medicine 2: 246-249.

Ju J et al. Four-color DNA sequencing by synthesis using cleavable fluorescent nucleotide reversible terminators. Proc Natl Acad Sci U S A. Dec. 26, 2006;103(52):19635-40. Epub Dec. 14, 2006.

Bai, X., Kim, S., Li, Z., Turro, N.J. and Ju, J. Design and synthesis of a photocleavable biotinylated nucleotide for DNA analysis by mass spectrometry. Nucleic Acids Research 2004, 32(2); pp. 534-541.

Li, Z., Bai, X., Ruparel, H., Kim, S., Turro, N.J. and Ju, J. A photocleavable fluorescent nucleotide for DNA sequencing and analysis. Proc. Natl. Acad. Sci. USA 2003, 100, 414-419.

Seo, T. S., Bai, X., Ruparel, H., Li, Z., Turro, N.J. and Ju, J. Photocleavable fluorescent nucleotides for DNA sequencing on a chip constructed by site-specific coupling chemistry. Proc. Natl. Acad. Sci. USA 2004, 101, 5488-5493.

Smith, L. M.; Sanders, J. Z.; Kaiser, R. J.; et al. "Fluorescence detection in automated DNA sequence analysis." Nature (1986), 321, pp. 674-679.

Zhu, Z.; Chao, J.; Yu, H; et al. "Directly labeled DNA probes using fluorescent nucleotides with different length linkers." Nucleic Acids Res. (1994), 22, pp. 3418-3422.

Notice of Allowance issued Apr. 2, 2010 in connection with U.S. Appl. No. 11/810,509, filed Jun. 5, 2007.

Office Action issued Feb. 18, 2010 in connection with U.S. Appl. No. 12/312,903, filed May 29, 2009.

Notice of Allowance issued Sep. 27, 2010 in connection with U.S. Appl. No. 12/312,903, filed May 29, 2009.

Arbo et al. (1993) "Solid Phase Synthesis of Protected Peptides Using New Cobalt (III) Amine Linkers," Int. J. Peptide Protein Res. 42:138-154.

Axelrod, V.D. et al. (1978) "Specific termination of RNA polymerase synthesis as a method of RNA and DNA sequencing," Nucleic Acids Res. 5(10):3549-3563.

Badman, E. R. et al. (2000) "A Parallel Miniature Cylindrical Ion Trap Array," Anal. Chem (2000) 72:3291-3297.

Badman, E. R. et al. (2000) "Cylindrical Ion Trap Array with Mass Selection by Variation in Trap Dimensions," Anal. Chem. 72:5079-5086.

Bai et al. (2003) "Photocleavage of a 2-nitrobenzyl Linker Bridging a Fluorophore to the 5' end of DNA," PNAS, vol. 100, No. 2, pp. 409-413.

Benson, S.C., Mathies, R.A., and Glazer, A.N. (1993) "Heterodimeric DNA-binding dyes designed for energy transfer: stability and applications of the DNA complexes," Nucleic Acids Res. 21:5720-5726.

Benson, S.C., Singh, P., and Glazer, A.N. (1993) "Heterodimeric DNA-binding dyes designed for energy transfer: synthesis and spectroscopic properties," Nucleic Acids Res. 21:5727-5735.

Bergmann et al. (1995) "Allyl as Internucleotide Protecting Group in DNA Synthesis to be Cleaved Off by Ammonia," Tetrahedron, 51:6971-6976.

Bergseid M., Baytan A.R., Wiley J.P., Ankener W.M., Stolowitz, Hughs K.A., and Chestnut J.D. (2000) "Small-molecule base chemical affinity system for the purification of proteins," BioTechniques 29:1126-1133.

Brunckova, J. et al. (1994) "Intramolecular Hydrogen Atom Abstrction in Carbohydrates and Nucleosides: Inversion of an α- to β-Mannopyranoside and Generation of Thymidine C-4' Radicals." Tetrahedron Letters, vol. 35, pp. 6619-6622.

Buck, G.A. et al. (1999) "Design Strategies and Performance of Custom DNA Sequencing Primers," BioTechniques 27(3):528-536.

Burgess, K. et al. (1997) "Photolytic Mass Laddering for Fast Characterization of Oligomers on Single Resin Beads," J. Org. Chem. 62:5662-5663.

Buschmann et al. (1999) "The Complex Formation of alpha,omega-Dicarboxylic Acids and alpha,omega-Diols with Cucurbituril and alpha-Cyclodextrin," Acta Chim. Slov. 46(3):405-411.

Buschmann et al. (2003) "Spectroscopic Study and Evaluation of Red-Absorbing Fluorescent Dyes," Bioconjugate Chem., 14:195-204.

Canard, B. et al. (1994) "DNA polymerase fluorescent substrates with reversible 3'-tags," Gene, 148:1-6.

Canard, B. et al. (1995) "Catalytic editing properties of DNA polymerases," Proc. Natl. Acad. Sci. USA 92:10859-10863.

Caetano-Anolies (1994) "DNA Amplification Fingerprinting Using Arbitrary Mini-hairpin Oligonucleotide Primers." Nature Biotechnology, 12:619-623.

Caruthers, M.H. (1985) "Gene synthesis machines: DNA chemistry and its uses," Science 230:281-285.

Chee, M. et al. (1996) "Accessing genetic information with high density DNA arrays," Science 274:610-614.

Chen, X. and Kwok, P.-Y. (1997) "Template-directed dye-terminator incorporation (TDI) assay: a homogeneous DNA diagnostic method based on fluorescence resonance energy transfer," Nucleic Acids Res. 25:347-353.

Chiu, N.H., Tang, K., Yip, P., Braun, A., Koster, H., and Cantor, C.R. (2000) "Mass spectrometry of single-stranded restriction fragments captured by an undigested complementary sequence," Nucleic Acids Res. 28:E31.

Crespo-Hernandez et al., (2000) "Part 1. Photochemical and Photophysical Studies of Guanine Derivatives: Intermediates Contributing to its Photodestruction Mechanism in Aqueous Solution and the Participation of the Electron Adduct," Photochemistry and Photobiology, 71(5):534-543.

Elango, N. et al. (1983) "Amino Acid Sequence of Human Respiratory Syncytial Virus Nucleocapsid Protein," Nucleic Acids Research 11(17):5941-5951.

Fallahpour, R.A. (2000) "Photochemical and Thermal reactions of Azido-Oligopyridines: Diazepinones, A New Class of Metal-Complex Ligands," Helvetica Chimica Acta. 83:384-393.

Fei, Z. et al. (1998) "MALDI-TOF mass spectrometric typing of single nucleotide polymorphisms with mass-tagged ddNTPs," Nucleic Acids Research 26(11):2827-2828.

Finzi, L. et al. (1995) "Measurement of Lactose Repressor-Mediated Loop Formation and Breakdown in Single DNA Molecules." Science, 267:378-380.

Gibson, K.J. et al. (1987) "Synthesis and Application of Derivatizable Oligonucleotides," Nucleic Acids Research, 15(16): 6455-6467.

Godovikova, T.S. et al. (1999) "5-[3-(E)-(4-Azido-2,3,5,6,-tetrafluorobenzamido)propenyl-1]-2'deoxyuridine-5'-triphosphate Substitutes for Thymidine-5'triphosphate in the Polymerase Chain Reaction," Bioconjugate Chem., 10:529-537.

Green, T.W. et al. and Wuts, P.G.M. "Protective Groups in Organic Synthesis" 3rd ed. New York: John Wiley & Sons, Inc., 1999. 96-99, 190-191, 260-261, 542-543, and 750-751.

Griffin, T.J. et al. (1999) "Direct Genetic Analysis by Matrix-Assisted Laser Desorption/Ionization Mass Spectrometry," Proc. Nat. Acad. Sci. USA 96:6301-6306.

Guibé (1997) "Allylic Protecting Groups and Their Use in a Complex Environment Part I: Allylic Protection of Alcohols," Tetrahedron, 53:13509-13556.

Guibé (1998) "Allylic Protecting Groups and Their Use in a Complex Environment Part II: Allylic Protecting Groups and their Removal through Catalytic Palladium n-Allyl Methodology," Tetrahedron, 54:2967-3042.

Hacia J.G., Edgemon K., Sun B., Stern D., Fodor S.A., and Collins F.S. (1998) "Two Color Hybridization Analysis Using High Density Oligonucleotide Arrays and Energy Transfer Dyes," Nucleic Acids Res. 26:3865-6.

Haff L.A., et al. (1997) "Multiplex Genotyping of PCR Products with Mass Tag-Labeled Primers," Nucleic Acids Res. 25(18):3749-3750.

Hafliger, D. et al. (1997) "Seminested RT-PCR Systems for Small Round Structured Viruses and Detection of Enteric Viruses in Seafood," International Journal of Food Microbiology 37:27-36.

Hanshaw et al. (2004) "An Indicator Displacement System for Fluorescent Detection of Phosphate Oxyanions Under Physiological Conditions," Tetrahedron Letters, vol. 45, pp. 8721-8724.

Hayakawa et al. (1993) "O-Allyl Protection of Guanine and Thymine Residues in Oligodeoxyribonucleotides," J. Org. Chem., 58:5551-5555.

Henner, W.D. et al. (1983) "Enzyme Action at 3' Termini of Ionizing Radiation-Induced DNA Strand Breaks," J. Biol. Chem. 258(24):15198-15205.

Hovinen et al. (1994) "Synthesis of 3'-O-(ω-Aminoalkoxymethyl) thymidine 5'-Triphosphates, Terminators of DNA Snythesis that Enable 3'-Labelling," J. Chem. Soc. Perkin Trans., 1:211-217.

Hu et al. (1999) "Optical Mapping of DNA Polymerase I Action and Products," BBRC, 254:466-473.

Huang, B.G. et al. "Synthesis and in vitro Antitumor Activity of Some Amino-deoxy 3-hexofuranosylpyrrolo [2,3-d]pyrimidines." Carbohydrate Research, 1998, 308(3-4):319-328.

Huber et al. (1999) "Monitoring Solid Phase Synthesis by Infrared Spectroscopic Techniques." Analytica Chimica Acta, 393:213.

Hultman et al. (1989) "Direct Solid Phase Sequencing of Genomic and Plasmid DNA Using Magnetic Beads as Solid Support," Nucleic Acids Research 17(3):4937-4946.

Ikeda, K. et al. (1995) "A Non-Radioactive DNA Sequencing Method Using Biotinylated Dideoxynucleoside Triphosphates and Delta TTH DNA Polymerase," DNA Research 2(31):225-227.

Ireland, R.E. and Varney, M.D. (1986) "Approach to the total synthesis of chlorothricolide: synthesis of (±)-19.20-dihydro-24-O-methylchlorothricolide, methyl ester, ethyl carbonate," J. Org. Chem. 51:635-648.

Jiang-Baucom, P. et al. (1997) "DNA Typing of Human Leukocyte Antigen Sequence Polymorphisms by Peptide Nucleic Acid Probes and MALDI-TOF Mass Spectrometry," Anal. Chem. 69:4894-4896.

Jurinke, C., van de Boom, D., Collazo, V., Luchow, A., Jacob, A., and Koster H. (1997) "Recovery of nucleic acids from immobilized biotin-streptavidin complexes using ammonium hydroxide and application in MALDI-TOF mass spectrometry," Anal. Chem. 69:904-910.

Kamal, A., Laxman, E., and Rao, N.V. (1999) "A mild and rapid regeneration of alcohols from their allylic ethers by chlorotrimethylsilane/sodium iodide," Tetrahedron Lett 40:371-372.

Kim Sobin et al. (2002) "Solid Phase Capturable Dideoxynucleotides for Multiplex Genotyping Using Mass Spectrometry," Nucleic Acids Research 30(16):e85.1-e85.6.

Kim, S. et al. (2003) "Multiplex Genotyping of the Human Beta2-adrenergic Receptor Gene Using Solid-phase Capturable Dideoxynucleotides and Mass Spectrometry," Analytical Biochemistry 316:251-258.

Kimzey A.L. et al. (1998) "Specific Regions of Contact Between Human T-cell Leukemia Virus Type I Tax Protein and DNA Identified by Photocross-linking," Journal of Biological Chemistry, 273(22): 13768-13775.

Kitamura et al. (2002) "(P(C6H5)3)CpRu+Catalyzed Deprotection of Allyl Carboxylic Esters," J. Org. Chem., 67:4975-497.

Kloosterman et al. (1985) "The relative stability of allyl ether, allyloxycarbonyl ester and prop-2 enylidene acetal, protective groups toward Iridium, Rhodium and Palladium catalysts," Tetrahedron Letters, 26:5045-5048.

Kokoris, M. et al. (2000) "High-throughput SNP Genotyping With the Masscode System," Molecular Diagnosis 5(4):329-3.

Kolb et al. (2001) "Click Chemistry: Diverse Chemical Function From a Few Good Reactions," Angew. Chem. Int. Ed. 40:2004-2021.

Kraevskii, A.A. et al. (1987) "Substrate Inhibitors of DNA Biosynthesis," Molecular Biology 21:25-29.

Krečmerová (1990) "Synthesis of 5'-O-Phosphonomethyl Derivatives of Pyrimidine 2'-Deoxynucleosides." Coll. Czech. Chem. Commun., 55:2521-2536.

Kurata et al. (2001) "Fluorescent quenching-based quantitative detection of specific DNA/RNA using BODIPY® FL-labeled probe of primer," Nucleic Acids Research, vol. 29, No. 6, p. e34.

Kvam et al., (1994) "Characterization of singlet oxygen-induced guanine residue damage after photochemical treatment of free nucleosides and DNA," Biochemica et Biophysica Acta., 1217:9-15.

Lee, L.G., et al. (1992) "DNA sequencing with dye labeled terminators and T7 DNA polymerase effect of dyes and dNTPs on incorporation of dye terminators and probability analysis of termination fragments," Nucleic Acids Res. 20:2471-2483.

Lee, L.G. et al, (1997) "New energy transfer dyes for DNA sequencing," Nucleic Acids Res. 25:2816-2822.

Leroy, E.M. et al. (2000) "Diagnosis of Ebola Haemorrhagic Fever by RT-PCR in an Epidemic Setting," Journal of Medical Virology 60:463-467.

Lewis et al. (2002) "Click Chemistry in Situ: Acetylcholinesterase as a Reaction Vessel for the Selective Assembly of a Femtomolar Inhibitor from an Array of Building Blocks," Angew. Chem. Int. Ed. 41(6):1053-1057.

Li, J. (1999) "Single Oligonucleotide Polymorphism Determination Using Primer Extension and Time-of-Flight Mass Spectrometry," Electrophoresis 20:1258-1265.

Liu, H. et al. (2000) "Development of Multichannel Devices with an Array of Electrospray Tips for High-Throughput Mass Spectrometry," Anal. Chem. 72:3303-3310.

Loubinoux, B. et al. "Protection Des Phenols Par Le Groupement Azidomethylene Application A La Synthese De Phenols Instables," Tetrahedron, 1998, 44 (19) : 6055 (English Abstract Only).

Lyamichev, V. et al. (1999) "Polymorphism Identification and Quantitative Detection of Genomic DNA by Invasive Cleavage of Oligonucleotide Probes," Nat. Biotech 17:292-296.

Maier et al. (1995) "Synthesis and Properties of New Fluorescein-Labeled Oligonucleotides," Nucleosides and Nucleotides, 14:961-965.

Markiewicz et al. (1997) "A new method of synthesis of fluorescently labeled oligonucleotides and their application in DNA sequencing," Nucleic Acids Research, 25:3672-3690.

Marquez et al. (2003) "Selective Fluorescence Quenching of 2,3-Diazabicyclo[2.2.2]oct-2-ene by Nucleotides," Organic Letters, 5:3911-3914.

Mathew C.K. et al. (1985) "Chemical Synthesis of Oligonucleotides," Biochemistry, 2nd Edition, pp. 127-128.

Monforte, J.A. and Becker, C.H. (1997) "High-throughput DNA analysis by time-of-flight mass spectrometry," Nat. Med. 3(3):360-362.

Nazarenko et al. (2002) "Effect of primary and secondary structure of oligodeoxyribonucleotides on the fluorescent properties of conjugated dyes," Nucleic Acids Research, 30:2089-2095.

Nickel et al. (1992) "Interactions of Azidothymidine triphosphate with the Cellular DNA polymerases alpha, delta, and episilon and with DNA Primase," J. Biol. Chem. 267(2):848-854.

Nielsen et al. (2004) "Multiplexed Sandwich Assays in Microarray Format," Journal of Immunological Methods, vol. 290, pp. 107-120.

Nishino et al. (1991) "Efficient Deanilidation of Phosphoranilidates by the Use of Nitrites and Acetic Anhydride." Heteroatom Chemistry, vol. 2, pp. 187-196.

Olejnik, J. et al. (1995) "Photocleavable biotin derivatives: a versatile approach for the isolation of biomolecules," Proc. Natl. Acad. Sci. USA. 92:7590-7594.

Olejnik, J. et al. (1999) "Photocleavable peptide DNA conjugates: synthesis and applications to DNA analysis using MALDI MS," Nucleic Acids Res. 27:4626-4631.

Pastinen et al. (1997) "Minisequencing: A Specific Tool for DNA Analysis and Diagnostics on Oligonucleotide Arrays," Genomic Res., 7:606-614.

Quaedflieg et al. (1992) "An Alternative Approach Toward the Synthesis of (3'->5') Methylene Acetal Linked Dinucleosides." Tetrahedron Letters, vol. 33, pp. 3081-3084.

Rao et al. (2001) "Four Color FRET Dye Nucleotide Terminators for DNA Sequencing," Nucleosides, Nucleotides and Nucleic Acids, 20:673-676.

Rasolonjatovo et al. (1998) "6-N-(N-Methylanthranylamido)-4-Oxo-Hexanoic Acid: A New Fluorescent Protecting Group Applicable to a New DNA Sequencing Method," Nucleosides and Nucleotides, 17:2021-2025.

Ronaghi, (1998) "PCR-Introduced Loop Structure As Primer in DNA Sequencing." BioTechniques, 25:876.

Ross, P.L. et al. (1997) "Discrimination of Single-Nucleotide Polymorphisms in Human DNA Using Peptide Nucleic Acid Probes Detected by MALDI-TOF Mass Spectrometry," Anal. Chem. 69:4197-4202.

Ross, P. et al. (1998) High Level Multiplex Genotyping by MALDI-TOF Mass Spectrometry. Nat. Biotech 16:1347-1351.

Sarfati et al., (1995) "Synthesis of fluorescent derivatives of 3'-O-(6-aminohexanoyl)-pyrimidine nucleosides 5'-triphosphates that act as DNA polymerase substrates reversibly tagged at C-3'," JCS Perkin Trans, 1163-1171.

Saxon, E. and Bertozzi, C.R. (2000) "Cell surface engineering by a modified Staudinger reaction," Science 287:2007-2010.

Schena, M., Shalon, D. and Davis, R. Brown P.O. (1995) "Quantitative monitoring of gene expression patterns with a cDNA microarray," Science 270: 467-470.

Seeger (1998) "Single Molecule Fluorescence: High-Performance Molecular Diagnosis and Screening," Bioforum, Git Verlag, Darmstadt, DE vol. 21.

Seo et al. (2003) "Click Chemistry to Construct Fluorescent Oligonucleotides for DNA Sequencing," J. Org. Chem. 68:609.

Speicher, M.R., Ballard, S.G., and Ward, D.C. (1996) "Karyotyping human chromosomes by combinatorial multi-fluor FISH," Nature Genetics 12: 368-375.

Stoerker, J. et al. (2000) "Rapid Genotyping by MALDI-monitored nuclease selection from probe Libraries," Nat. Biotech 18:1213-1216.

Tang, K., Fu, D.J., Julien, D., Braun, A., Cantor, C.R., and Koster, H. (1999) "Chip-based genotyping by mass spectrometry," Proc. Natl. Acad. Sci. USA. 96:10016-10020.

Tong, X. and Smith, L.M. (1992) "Solid-Phase Method for the Purification of DNA Sequencing Reactions," Anal. Chem. 64:2672-2677.

Torimura et al. (2001) "Fluorescence-Quenching Phenomenon by Photoinduced Electron Transfer between a Fluorescent Dye and Nucleotide Base," Analytical Sciences, 17:155-160.

Tuncel et al. (1999) "Catalytically Self-Threading Polyrotaxanes," Chem. Comm. 1509-1510.

Veeneman et al. (1991) "An Efficient Approach to the Synthesis of Thymidine Driatives Containing Phosphate-Isoteric Methylene Acetyl Linkages," Tetrahedron, 47:1547-1562.

Wada et al. (2001) "2-(Azidomethyl)benzoyl as a new protecting group in nucleosides," Tetrahedron Letters, 42:1069-10.

Weiss (1999) "Fluorescent Spectroscopy of Single Biomolecules." Science, 283:1676.

Welch et al. (1999) "Synthesis of Nucleosides Designed for Combinatorial DNA Sequencing," Chemistry, European Journal, 5:951-960.

Wendy, Jen. Et al. (2000) "New Strategies for Organic Catalysis: The First Enantioselective Orgacnocatalytic 1,3-Dipolar Cycloaddition," J. Am. Chem. Soc. 122:9874-9875.

Woolley, A. T. et al. (1997) "High-Speed DNA Genotyping Using Microfabricated Capillary Array Electrophoresis Chips," Anal. Chem. 69:2181-2186.

Yamashita et al. (1987) "Studies on Antitumor Agents VII. Antitumor Activities of O-Alkoxyalkyl Derivatives of 2'-Deoxy-5-trifluoromethyluridine." Chem Pharm. Bull., vol. 35, pp. 2373-2381.

Zavgorodny, S. et al. (1991) "1-Alkylthioalkylation of Nucleoside Hydroxyl Functions and Its Synthetic Applications: A New Versatile Method in Nucleoside Chemistry," Tetrahedron Letters, 32(51): 7593-7596.

Zavgorodny et al. (2000) Nucleosides, Nucleotides and Nucleic Acids, 19(10-12):1977-1991.

Zhang et al. (2002) "Synthesis of Releasable Electrophore Tags for Applications in Mass Spectrometry," Bioconjugate Chem., vol. 13, pp. 1002-1101.

Partial European Search Report issued Apr. 26, 2007 in connection with European Patent Application No. 07004522.4.

Extended European Search Report issued Jul. 18, 2007 in connection with European Patent Application No. 07004522.4.

Official Action issued Mar. 3, 2007 in connection with European Patent Application No. 07004522.4.

Communication Pursuant to Article 94(3) EPC issued Apr. 30, 2009 in connection with counterpart European Patent Application No. 07004522.4.

International Search Report issued Jan. 23, 2002 in connection with PCT/US01/28967.

International Search Report issued May 13, 2002 in connection with PCT/US01/31243.

International Search Report issued Sep. 18, 2002 in connection with PCT/US02/09752.

International Preliminary Examination Report issued on Feb. 25, 2003 in connection with PCT/US01/28967.

International Preliminary Examination Report issued on Mar. 17, 2003 in connection with PCT/US02/09752.

International Preliminary Examination Report issued on Jun. 13, 2003 in connection with PCT/US01/31243.

International Search Report issued Sep. 26, 2003 in connection with PCT/US03/21818.

International Preliminary Examination Report issued on Mar. 18, 2005 in connection with PCT/US03/21818.

International Preliminary Report on Patentability issued on Sep. 5, 2006 in connection with PCT/US05/06960.

International Search Report issued Oct. 29, 2007 in connection with PCT International Application No. PCT/US07/13559.

International Search Report issued Jun. 8, 2004 in connection with PCT/US03/39354.

International Search Report issued Nov. 4, 2005 in connection with PCT/US05/06960.

International Search Report issued Dec. 15, 2006 in connection with PCT/US05/13883.

Supplementary European Search Report issued Feb. 16, 2004 in connection with European Patent Application No. 01977533.

Supplementary European Search Report issued May 25, 2005 in connection with European Patent Application No. 02728606.1.

Supplementary European Search Report issued Jun. 7, 2005 in connection with European Patent Application No. 01968905.

Supplementary European Search Report issued Feb. 9, 2007 in connection with European Patent Application No. 03764568.6.

Supplementary European Search Report issued Sep. 9, 2008 in connection with PCT International Application No. PCT/US05/06960.

Written Opinion of the International Searching Authority issued Oct. 27, 2005 in connection with PCT/US05/06960.

Written Opinion of the International Searching Authority issued Dec. 15, 2006 in connection with PCT/US05/13883.

Office Action issued Oct. 25, 2002 in connection with U.S. Appl. No. 09/972,364.

Office Action issued Mar. 14, 2003 in connection with U.S. Appl. No. 09/972,364.

Office Action issued Aug. 10, 2007 in connection with U.S. Appl. No. 11/119,231.

Office Action issued Sep. 21, 2007 in connection with U.S. Appl. No. 10/380,256.

Restriction Requirement issued Oct. 1, 2007 in connection with U.S. Appl. No. 10/521,206.

Office Action issued Nov. 14, 2007 in connection with U.S. Appl. No. 10/735,081.

Office Action issued Jun. 24, 2008 in connection with U.S. Appl. No. 11/894,690.

Office Action issued Jun. 5, 2009 in connection with U.S. Appl. No. 11/894,690.

Office Action issued Sep. 3, 2008 in connection with U.S. Appl. No. 11/894,808.

Office Action issued Jul. 8, 2008 in connection with U.S. Appl. No. 10/591,520.

Official Action issued Mar. 31, 2006 in connection with European Patent Application No. 01968905.8.

Official Action issued May 21, 2007 in connection with European Patent Application No. 01968905.8.

Notice of Allowance issued Sep. 6, 2007 in connection with U.S. Appl. No. 10/702,203.

Notification of Transmittal of International Search Report and Written Opinion, issued Nov. 23, 2007 in connection with International Application No. PCT/US06/42698.

Notification of Transmittal of International Search Report and Written Opinion, issued Feb. 6, 2008 in connection with International Application No. PCT/US06/42739.

Notification Concerning Transmittal of International Preliminary Report on Patentability (Including Written Opinion of the International Searching Authority) issued May 15, 2008 in connection with PCT/US2006/042698.

Notification of Transmittal of International Search Report and Written Opinion, issued May 22, 2008 in connection with International Application No. PCT/US06/45180.

Notification of Transmittal of International Search Report and Written Opinion, issued Aug. 12, 2008 in connection with International Application No. PCT/US07/24646.

Notification of Transmittal of International Search Report and the Written Opinion of the International Searching Authority, or the Declaration issued Sep. 9, 2008 in connection with International Application No. PCT/US06/24157.

* cited by examiner

Extension with 3'-O-allyl-dNTP-allyl-Dye on a repeat A template.

Extension with 3'-O-allyl-dNTP-allyl-Dye on a repeat G template:

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
gttgatgtac acattgtcaa                    20

<210> SEQ ID NO 2
<211> LENGTH: 100

```
<212> TYPE: DNA
<213> ORGANISM: Artificial Sequence
<220> FEATURE:
<223> OTHER INFORMATION: template

<400> SEQUENCE: 2
tacccggagg ccaagtacgg cgggtacgtc cttgacaatg tgtacatcaa catcacctac      60
caccatgtca gtctcggttg gatcctctat tgtgtccggg                           100

<210> SEQ ID NO 3
<211> LENGTH: 48
<212> TYPE: DNA
<213> ORGANISM: Artificial Sequence
<220> FEATURE:
<223> OTHER INFORMATION: template

<400> SEQUENCE: 3
tttttgtttt tttttttcgat cgacttaagg cgcttgcgcc ttaagtcg                  48

<210> SEQ ID NO 4
<211> LENGTH: 82
<212> TYPE: DNA
<213> ORGANISM: Artificial Sequence
<220> FEATURE:
<223> OTHER INFORMATION: template

<400> SEQUENCE: 4
agtcagtctc tcatctcgac atctacgcta ctcgtcgatc ggaaacagct atgaccatgc      60
ttgcatggtc atagctgttt cc                                               82

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
agaggatcca accgagac                                                    18

<210> SEQ ID NO 6
<211> LENGTH: 60
<212> TYPE: DNA
<213> ORGANISM: Artificial Sequence
<220> FEATURE:
<223> OTHER INFORMATION: template

<400> SEQUENCE: 6
gtgtacatca acatcaccta ccaccatgtc agtctcggtt ggatcctcta ttgtgtccgg      60
```

FOUR-COLOR DNA SEQUENCING BY SYNTHESIS USING CLEAVABLE FLUORESCENT NUCLEOTIDE REVERSIBLE TERMINATORS

This application is a continuation of U.S. Ser. No. 12/312,903, filed May 9, 2009, now U.S. Pat. No. 7,883,869, issued Feb. 8, 2011, which is a §371 national stage of PCT International Application No. PCT/US2007/024646, filed Nov. 30, 2007, and claims the benefit of U.S. Provisional Application No. 60/872,240, filed Dec. 1, 2006, the contents of each of which are hereby incorporated by reference in their entireties into this application.

Throughout this application, various publications are referenced in parentheses by number. Full citations for these references may be found at the end of the specification immediately preceding the claims. The disclosures of these publications in their entireties are hereby incorporated by reference into this application to more fully describe the state of the art to which this invention pertains.

This invention was made with government support under grant number P50-HG002806 awarded by the National Institutes of Health. The government has certain rights in the invention.

BACKGROUND OF THE INVENTION

DNA sequencing is driving genomics research and discovery. The completion of the Human Genome Project has set the stage for screening genetic mutations to identify disease genes on a genome-wide scale (1). Accurate high-throughput DNA sequencing methods are needed to explore the complete human genome sequence for applications in clinical medicine and health care. To overcome the limitations of the current electrophoresis-based sequencing technology (2-5), a variety of new DNA-sequencing methods have been investigated. Such approaches include sequencing by hybridization (6), mass spectrometry based sequencing (7-9), sequence-specific detection of single-stranded DNA using engineered nanopores (10) and sequencing by ligation (11). More recently, DNA sequencing by synthesis (SBS) approaches such as pyrosequencing (12), sequencing of single DNA molecules (13) and polymerase colonies (14) have been widely explored.

The concept of DNA sequencing by synthesis (SBS) was revealed in 1988 with an attempt to sequence DNA by detecting the pyrophosphate group that is generated when a nucleotide is incorporated in a DNA polymerase reaction (15). Pyrosequencing which was developed based on this concept and an enzymatic cascade has been explored for genome sequencing (16). However, there are inherent difficulties in this method for determining the number of incorporated nucleotides in homopolymeric regions of the template. Additionally, each of the four nucleotides needs to be added and detected separately, which increases the overall detection time. The accumulation of un-degraded nucleotides and other components could also lower the accuracy of the method when sequencing a long DNA template. It is thus desirable to have a simple method to directly detect a reporter group attached to the nucleotide that is incorporated into a growing DNA strand in the polymerase reaction rather than relying on a complex enzymatic cascade. The SBS scheme based on fluorescence detection coupled with a chip format has the potential to markedly increase the throughput of DNA sequencing projects. Consequently, several groups have investigated such a system with an aim to construct an ultra high-throughput DNA sequencing method (17-18). Thus far, no complete success of using such a system to unambiguously sequence DNA has been published.

Previous work in the literature exploring the SBS method is mostly focused on designing and synthesizing a cleavable chemical moiety that is linked to a fluorescent dye to cap the 3'-OH group of the nucleotides (19-21). The rationale is that after the fluorophore is removed, the 3'-OH would be regenerated to allow subsequent nucleotide addition. However, no success has been reported for the incorporation of such a nucleotide with a cleavable fluorescent dye on the 3' position by DNA polymerase into a growing DNA strand. The reason is that the 3' position on the deoxyribose is very close to the amino acid residues in the active site of the polymerase, and the polymerase is therefore sensitive to modification in this area of the ribose ring, especially with a large fluorophore (22).

SUMMARY OF THE INVENTION

This invention provides a method for determining the sequence of a DNA comprising performing the following steps for each residue of the DNA to be sequenced:
(a) contacting the DNA with a DNA polymerase in the presence of (i) a primer and (ii) four nucleotide analogues under conditions permitting the DNA polymerase to catalyze DNA synthesis, wherein (1) the nucleotide analogues consist of an analogue of dGTP, an analogue of dCTP, an analogue of dTTP or dUTP, and an analogue of dATP, (2) each nucleotide analogue comprises (i) a base selected from the group consisting of adenine, guanine, cytosine, thymine or uracil, and analogues thereof, (ii) a deoxyribose, (iii) a moiety cleavably linked to the 3'-oxygen of the deoxyribose and (iv) a unique label cleavably linked to the base, so that a nucleotide analogue complementary to the residue being sequenced is incorporated into the DNA by the DNA polymerase, and (3) each of the four analogues has a unique label which is different than the unique labels of the other three analogues;
(b) removing unbound nucleotide analogues;
(c) again contacting the DNA with a DNA polymerase in the presence of (i) a primer and (ii) four reversible terminators under conditions permitting the DNA polymerase to catalyze DNA synthesis, wherein (1) the reversible terminators consist of an analogue of dGTP, an analogue of dCTP, an analogue of dTTP or dUTP, and an analogue of dATP, (2) each nucleotide analogue comprises (i) a base selected from the group consisting of adenine, guanine, cytosine, thymine or uracil, and analogues thereof, which base does not have a unique label bound thereto, (ii) a deoxyribose, and (iii) a moiety cleavably linked to the 3'-oxygen of the deoxyribose;
(d) removing unbound reversible terminators;
(e) determining the identity of the nucleotide analogue incorporated in step (a) via determining the identity of the corresponding unique label, with the proviso that step (e) can either precede step (c) or follow step (d); and
(f) following step (e), except with respect to the final DNA residue to be sequenced, cleaving from the incorporated nucleotide analogues the unique label, if applicable, and the moiety linked to the 3'-oxygen atom of the deoxyribose,
thereby determining the sequence of the DNA.

This invention also provides a kit for performing the method of claim 1, comprising, in separate compartments,
(a) nucleotide analogues of (i) GTP, (ii) ATP, (iii) CTP and (iv) TTP or UTP, wherein each analogue comprises (i) a base selected from the group consisting of adenine, guanine, cytosine, thymine or uracil, or an analogue thereof, (ii) a deoxyribose, (iii) a cleavable moiety bound to the 3'-oxygen of the deoxyribose and (iv) a unique label bound to the base via a cleavable linker, (b) reversible terminators comprising a nucleotide analogue of (i) GTP, (ii) ATP, (iii) CTP and (iv) TTP or UTP, wherein each analogue comprises (i) a base selected from the group consisting of adenine, guanine, cytosine, thymine or uracil, or an analogue thereof, which base does not have a unique label bound thereto, (ii) a deoxyribose, and (iii) a cleavable moiety bound to the 3'-oxygen of the deoxyribose;

(c) reagents suitable for use in DNA polymerization; and (d) instructions for use.

DETAILED DESCRIPTION OF THE INVENTION

Terms

Figure 1:
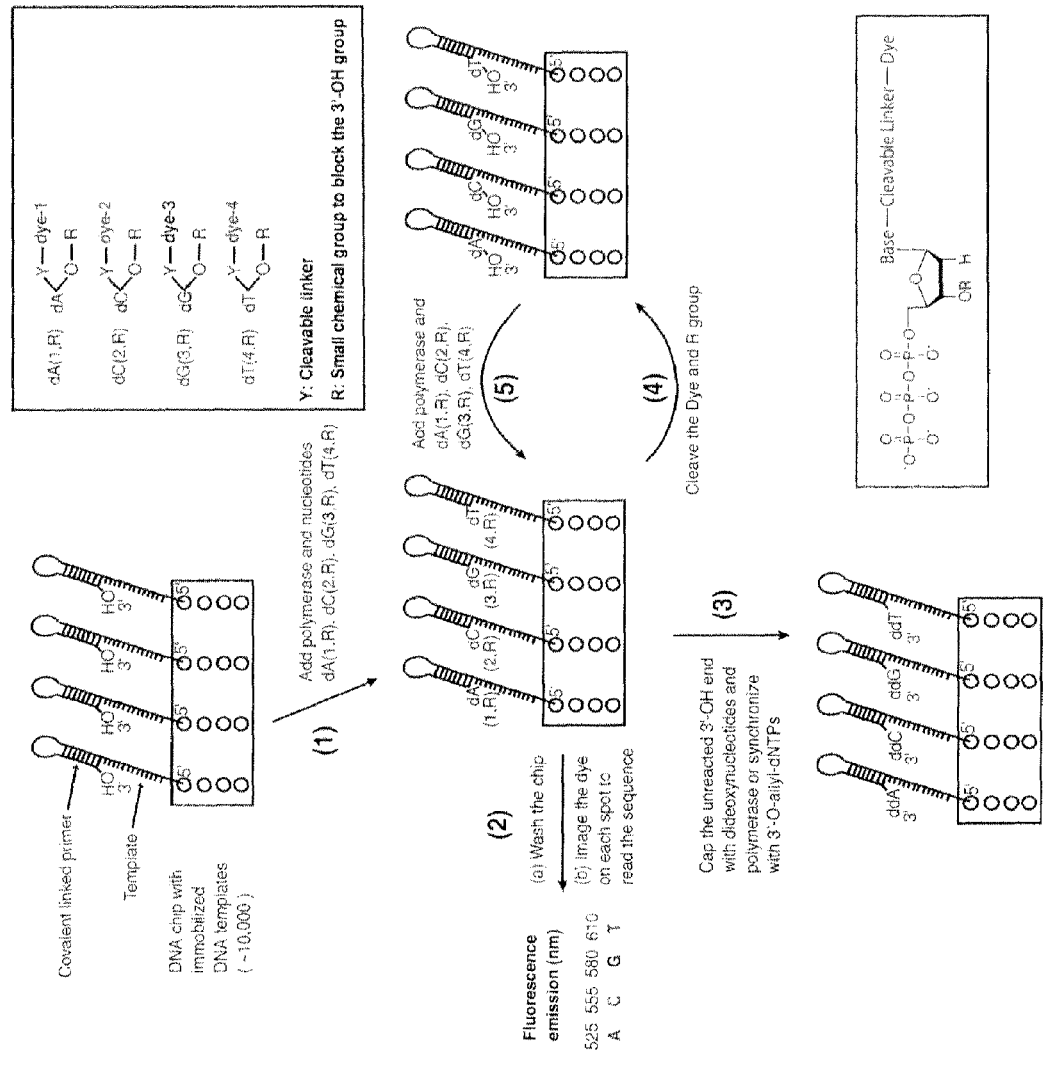
FIG. 1. A chip is constructed with immobilized DNA templates that are able to self-prime for initiating the polymerase reaction. Four nucleotide analogues are designed such that each is labeled with a unique fluorescent dye on the specific location of the base through a cleavable linker, and a small chemically reversible moiety (R) to cap the 3'-OH group. Upon adding the four nucleotide analogues and DNA polymerase, only the nucleotide analogue complementary to the next nucleotide on the template is incorporated by polymerase on each spot of the chip (step 1). A 4 color fluorescence imager is used to image the surface of the chip, and the unique fluorescence emission from the specific dye on the nucleotide analogues on each spot of the chip will yield the identity of the nucleotide (step 2). After imaging, the small amount of unreacted 3'-OH group on the self-primed template moiety is capped by excess ddNTPs and DNA polymerase to avoid interference with the next round of synthesis Or by to synchronize the incorporation (step 3). The dye moiety and the R protecting group will be removed to generate a free 3'-OH group with high yield (step 4). The self-primed DNA moiety on the chip at this stage is ready for the next cycle of the reaction to identify the next nucleotide sequence of the template DNA (step 5).

As used herein, and unless stated otherwise, each of the following terms shall have the definition set forth below.

A—Adenine;

C—Cytosine;

DNA—Deoxyribonucleic acid;

G—Guanine;

RNA—Ribonucleic acid;

T—Thymine; and

U—Uracil.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Type" of nucleotide refers to A, G, C, T or U.

"Mass tag" shall mean a molecular entity of a predetermined size which is capable of being attached by a cleavable bond to another entity.

"Solid substrate" shall mean any suitable medium present in the solid phase to which an antibody or an agent may be affixed.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Embodiments of the Invention

This invention provides a method for determining the sequence of a DNA comprising performing the following steps for each residue of the DNA to be sequenced:

(a) contacting the DNA with a DNA polymerase in the presence of (i) a primer and (ii) four nucleotide analogues under conditions permitting the DNA polymerase to catalyze DNA synthesis, wherein (1) the nucleotide analogues consist of an analogue of dGTP, an analogue of dCTP, an analogue of dTTP or dUTP, and an analogue of dATP, (2) each nucleotide analogue comprises (i) a base selected from the group consisting of adenine, guanine, cytosine, thymine or uracil, and analogues thereof, (ii) a deoxyribose, (iii) a moiety cleavably linked to the 3'-oxygen of the deoxyribose and (iv) a unique label cleavably linked to the base, so that a nucleotide analogue complementary to the residue being sequenced is incorporated into the DNA by the DNA polymerase, and (3) each of the four analogues has a unique label which is different than the unique labels of the other three analogues;

(b) removing unbound nucleotide analogues;

(c) again contacting the DNA with a DNA polymerase in the presence of (i) a primer and (ii) four reversible terminators under conditions permitting the DNA polymerase to catalyze DNA synthesis, wherein (1) the reversible terminators consist of an analogue of dGTP, an analogue of dCTP, an analogue of dTTP or dUTP, and an analogue of dATP, (2) each nucleotide analogue comprises (i) a base selected from the group consisting of adenine, guanine, cytosine, thymine or uracil, and analogues thereof, which base does not have a unique label bound thereto, (ii) a deoxyribose, and (iii) a moiety cleavably linked to the 3'-oxygen of the deoxyribose;

(d) removing unbound reversible terminators;

(e) determining the identity of the nucleotide analogue incorporated in step (a) via determining the identity of the corresponding unique label, with the proviso that step (e) can either precede step (c) or follow step (d); and (f) following step (e), except with respect to the final DNA residue to be sequenced, cleaving from the incorporated nucleotide analogues the unique label, if applicable, and the moiety linked to the 3'-oxygen atom of the deoxyribose, thereby determining the sequence of the DNA.

This invention also provides the instant method, wherein step (e) is performed before step (c).

This invention also provides the instant method, wherein the moiety cleavably linked to the 3'-oxygen of the deoxyribose is chemically cleavable or photocleavable. This invention also provides the instant method, wherein the moiety cleavably linked to the 3'-oxygen of the deoxyribose in the nucleotide analogs of step (a) is an allyl moiety or a 2-nitrobenzyl moiety.

This invention also provides the instant method, wherein the moiety cleavably linked to the 3'-oxygen of the deoxyribose in the reversible terminators of step (c) is an allyl moiety or a 2-nitrobenzyl moiety.

This invention also provides the instant method, wherein the unique label is bound to the base via a chemically cleavable or photocleavable linker.

This invention also provides the instant method, wherein the unique label bound to the base via a cleavable linker is a dye, a fluorophore, a chromophore, a combinatorial fluorescence energy transfer tag, a mass tag, or an electrophore.

This invention also provides the instant method, wherein the moiety is chemically cleavable with $Na_2PdCl_4/P(PhSO_3Na)_3$. This invention also provides the instant method, wherein the linker is chemically cleavable with $Na_2PdCl_4/P(PhSO_3Na)_3$.

This invention also provides the instant method, wherein the primer is a self-priming moiety.

This invention also provides the instant method, wherein the DNA is bound to a solid substrate. This invention also provides the instant method, wherein the DNA is bound to the solid substrate via 1,3-dipolar azide-alkyne cycloaddition chemistry. This invention also provides the instant method, wherein the DNA is bound to the solid substrate via a polyethylene glycol molecule. This invention also provides the instant method, wherein the DNA is alkyne-labeled. This invention also provides the instant method, wherein the DNA is bound to the solid substrate via a polyethylene glycol molecule and the solid substrate is azide-functionalized. This invention also provides the instant method, wherein the DNA is immobilized on the solid substrate via an azido linkage, an alkynyl linkage, or biotin-streptavidin interaction.

This invention also provides the instant method, wherein the solid substrate is in the form of a chip, a bead, a well, a capillary tube, a slide, a wafer, a filter, a fiber, a porous media, or a column. This invention also provides the instant method, wherein the solid substrate is gold, quartz, silica, plastic, glass, diamond, silver, metal, or polypropylene. This invention also provides the instant method, wherein the solid substrate is porous.

This invention also provides the instant method, wherein about 1000 or fewer copies of the DNA are bound to the solid substrate. This invention also provides the instant invention wherein $1\times10^7$, $1\times10^4$ or $1\times10^4$ or fewer copies of the DNA are bound to the solid substrate.

This invention also provides the instant method, wherein the four nucleotide analogues in step (a) are 3'-O-allyl-dGTP-allyl-Cy5, 3'-O-allyl-dCTP-allyl-Bodipy-FL-510, 3'-O-allyl-dATP-allyl-ROX and 3'-O-allyl-dUTP-allyl-R6G. This invention also provides the instant method, wherein the four nucleotide analogues in step (a) are 3'-O-allyl-dGTP-allyl-Bodipy-FL-510, 3'-O-allyl-dCTP-allyl-Bodipy-650, 3'-O-allyl-dATP-allyl-ROX and 3'-O-allyl-dUTP-allyl-R60. This invention also provides the instant method, wherein the four nucleotide analogues in step (a) are 3'-O-allyl-dGTP-allyl-Bodipy-650, 3'-O-allyl-dCTP-allyl-Bodipy-FL-510, 3'-O-allyl-dATP-allyl-ROX and 3'-O-allyl-dUTP-allyl-R6G.

It is understood that in other embodiments the nucleotide analogues are photocleavable. For example, 2-nitrobenzyl can replace any of the allyl moieties in the analogues described herein. For example, 3'-O-2-nitrobenzyl-dGTP-allyl-Bodipy-650, 3'-O-2-nitrobenzyl-dGTP-2-nitrobenzyl-Bodipy-650, 3'-O-allyl-dGTP-2-nitrobenzyl-Bodipy-650. One of skill in the art would recognize various other chemically cleavable or photochemically cleavable moieties or linkers that can be used in place of the examples described herein. Additionally, the unique labels may also be varied, and the examples set forth herein are non-limiting. In an embodiment UV light is used to photochemically cleave the photochemically cleavable linkers and moieties.

This invention also provides the instant method, wherein the reversible terminators in step (c) are 3'-O-allyl-dGTP, 3'-O-allyl-dCTP, 3'-O-allyl-dATP and 3'-O-allyl-dUTP. This invention also provides the instant method, wherein the reversible terminators in step (c) are 3'-O-2-nitrobenzyl-dGTP, 3'-O-2-nitrobenzyl-dCTP, 3'-O-2-nitrobenzyl-dATP and 3'-O-2-nitrobenzyl-dUTP.

In an embodiment the reversible terminator is incorporated into the growing strand of DNA.

This invention also provides the instant method, wherein the DNA polymerase is a 9°N polymerase or a variant thereof. DNA polymerases which can be used in the instant invention include, for example E. Coli DNA polymerase I, Bacteriophage T4 DNA polymerase, Sequenase™, Taq DNA polymerase and 9° N polymerase (exo-) A485L/Y409V.RNA polymerases which can be used in the instant invention include, for example, Bacteriophage SP6, T7 and T3 RNA polymerases.

This invention also provides the instant method, wherein the DNA is bound to the solid substrate via a polyethylene glycol molecule and the solid substrate is azide-functionalized or the DNA is immobilized on the solid substrate via an azido linkage, an alkynyl linkage, or biotin-streptavidin interaction; wherein (i) the four nucleotide analogues in step (a) are 3'-O-allyl-dGTP-allyl-Cy5, 3'-O-allyl-dCTP-allyl-Bodipy-FL-510, 3'-O-allyl-dATP-allyl-ROX and 3'-O-allyl-dUTP-allyl-R6G, (ii) the four nucleotide analogues in step (a) are 3'-O-allyl-dGTP-allyl-Bodipy-FL-510, 3'-O-allyl-dCTP-allyl-Bodipy-650, 3'-O-allyl-dATP-allyl-ROX and 3'-O-allyl-dUTP-allyl-R6G, or (iii) the four nucleotide analogues in step (a) are 3'-O-allyl-dGTP-allyl-Bodipy-650, 3'-O-allyl-dCTP-allyl-Bodipy-FL-510, 3'-O-allyl-dATP-allyl-ROX and 3'-O-allyl-dUTP-allyl-R60; and wherein the reversible terminators in step (c) are 3'-O-allyl-dGTP, 3'-O-allyl-dCTP, 3'-O-allyl-dATP and 3'-O-allyl-dUTP.

This invention also provides a kit for performing the instant method comprising, in separate compartments,
(a) nucleotide analogues of (i) GTP, (ii) ATP, (iii) CTP and (iv) TTP or UTP, wherein each analogue comprises (i) a base selected from the group consisting of adenine, guanine, cytosine, thymine or uracil, or an analogue thereof, (ii) a deoxyribose, (iii) a cleavable moiety bound to the 3'-oxygen of the deoxyribose and (iv) a unique label bound to the base via a cleavable linker,
(b) reversible terminators comprising a nucleotide analogue of (i) GTP, (ii) ATP, (iii) CTP and (iv) TTP or UTP, wherein each analogue comprises (i) a base selected from the group consisting of adenine, guanine, cytosine, thymine or uracil, or an analogue thereof, which base does not have a unique label bound thereto, (ii) a deoxyribose, and (iii) a cleavable moiety bound to the 3'-oxygen of the deoxyribose;
(c) reagents suitable for use in DNA polymerization; and
(d) instructions for use.

This invention further provides the instant kit, wherein the nucleotide analogues of part (a) are 3'-O-allyl-dGTP-allyl-Cy5, 3'-O-allyl-dCTP-allyl-Bodipy-FL-510, 3'-O-allyl-dATP-allyl-ROX and 3'-O-allyl-dUTP-allyl-R6G. This invention further provides the instant kit, wherein the nucleotide analogues of part (a) are 3'-O-allyl-dGTP-allyl-Bodipy-FL-510, 3'-O-allyl-dCTP-allyl-Bodipy-650, 3'-O-allyl-dATP-allyl-ROX and 3'-O-allyl-dUTP-allyl-R6G. This invention further provides the instant kit, wherein the nucleotide analogues of part (a) are 3'-O-allyl-dGTP-allyl-Bodipy-650, 3'-O-allyl-dCTP-allyl-Bodipy-FL-510, 3'-O-allyl-dATP-allyl-ROX and 3'-O-allyl-dUTP-allyl-R6G. This invention further provides the instant kit, wherein the nucleotide analogues of part (b) are 3'-O-allyl-dGTP, 3'-O-allyl-dCTP, 3'-O-allyl-dATP and 3'-O-allyl-dUTP. This invention further provides the instant kit, the reversible terminators in step (c) are 3'-O-2-nitrobenzyl-dGTP, 3'-O-2-nitrobenzyl-dCTP, 3'-O-2-nitrobenzyl-dATP and 3'-O-2-nitrobenzyl-dUTP.

The methods and kits of this invention may be applied, mutatis mutandis, to the sequencing of RNA, or to determining the identity of a ribonucleotide.

Methods for production of cleavably capped and/or cleavably linked nucleotide analogues are disclosed in U.S. Pat. No. 6,664,079, which is hereby incorporated by reference. Combinatorial fluorescence energy tags and methods for production thereof are disclosed in U.S. Pat. No. 6,627,748, which is hereby incorporated by reference.

In an embodiment, the DNA or nucleic acid is attached/bound to the solid surface by covalent site-specific coupling chemistry compatible with DNA.

This invention will be better understood by reference to the Experimental Details which follow, but those skilled in the art will readily appreciate that the specific experiments detailed are only illustrative of the invention as described more fully in the claims which follow thereafter.

Experimental Details

DNA sequencing by synthesis (SBS) on a solid surface during polymerase reaction offers a new paradigm to decipher DNA sequences. Disclosed here is the construction of such a novel DNA sequencing system using molecular engineering approaches. In this approach, four nucleotides (A, C, G, T) are modified as reversible terminators by attaching a cleavable fluorophore to the base and capping the 3'-OH group with a small chemically reversible moiety so that they are still recognized by DNA polymerase as substrates. It is found that an allyl moiety can be used successfully as a linker to tether a fluorophore to 3'-O-allyl-modified nucleotides, forming chemically cleavable fluorescent nucleotide reversible terminators, 3'-O-allyl-dNTPs-allyl-fluorophore, for application in SBS. The fluorophore and the 3'-allyl group on a DNA extension product, which is generated by incorporating 3'-O-allyl-dNTPs-allyl-fluorophore in a polymerase reaction, are removed simultaneously in 30 seconds by Pd-catalyzed deallylation in aqueous buffer solution. This one-step dual-deallylation reaction thus allows the re-initiation of the polymerase reaction and increases the SBS efficiency. DNA templates consisting of homopolymer regions were accurately sequenced by using this new class of fluorescent nucleotide analogues on a DNA chip and a 4-color fluorescent scanner.

It is known that some modified DNA polymerases are highly tolerable for nucleotides with extensive modifications with bulky groups such as energy transfer dyes at the 5-position of the pyrimidines (T and C) and 7-position of purines (G and A) (23, 24). The ternary complexes of a rat DNA polymerase, a DNA template-primer, and dideoxycytidine triphosphate have been determined (22) which supports this fact. It was hypothesizrf that if a unique fluorescent dye is linked to the 5-position of the pyrimidines (T and C) and the 7-position of purines (G and A) via a cleavable linker, and a small chemical moiety is used to cap the 3'-OH group, then the resulting nucleotide analogues may be able to incorporate into the growing DNA strand as terminators. Based on this rationale, SBS approach was conceived using cleavable fluorescent nucleotide analogues as reversible terminators to sequence surface-immobilized DNA in 2000 (FIG. 1) (25). In this approach, the nucleotides are modified at two specific locations so that they are still recognized by DNA polymerase as substrates: (i) a different fluorophore with a distinct fluorescent emission is linked to each of the 4 bases through a cleavable linker and (ii) the 3'-OH group is capped by a small chemically reversible moiety. DNA polymerase incorporates only a single nucleotide analogue complementary to the base on a DNA template covalently linked to a surface. After incorporation, the unique fluorescence emission is detected to identify the incorporated nucleotide and the fluorophore is subsequently removed. The 3'-OH group is then chemically regenerated, which allows the next cycle of the polymerase reaction to proceed. Since the large surface on a DNA chip can have a high density of different DNA templates spotted, each cycle can identify many bases in parallel, allowing the simultaneous sequencing of a large number of DNA molecules. The feasibility of performing SBS on a chip using 4 photocleavable fluorescent nucleotide analogues was previously established (26) and it was discovered that an allyl group can be used as a cleavable linker to bridge a fluorophore to a nucleotide (27). The design and synthesis of two photocleavable fluorescent nucleotides as reversible terminators for polymerase reaction has already been reported (28, 29).

Previous research efforts in the present laboratory have firmly established the molecular level strategy to rationally modify the nucleotides by attaching a cleavable fluorescent dye to the base and capping the 3'-OH with a small chemically reversible moiety for SBS. This approach was recently adopted by Genomics Industry to potentially provide a new platform for DNA sequencing (30). Here the design and synthesis of 4 chemically cleavable fluorescent nucleotide analogues as reversible terminators for SBS is disclosed. Each of the nucleotide analogues contains a 3'-O-allyl group and a unique fluorophore with a distinct fluorescence emission at the base through a cleavable allyl linker.

It was first established that these nucleotide analogues are good substrates for DNA polymerase in a solution-phase DNA extension reaction and that the fluorophore and the 3'-O-allyl group can be removed with high efficiency in aqueous solution. Then SBS was performed using these 4 chemically cleavable fluorescent nucleotide analogues as reversible terminators to identify ~20 continuous bases of a DNA template immobilized on a chip. Accurate DNA sequences were obtained for DNA templates containing homopolymer sequences. The DNA template was immobilized on the surface of the chip that contains a PEG linker with 1,3-dipolar azide-alkyne cycloaddition chemistry. These results indicated that successful cleavable fluorescent nucleotide reversible terminators for 4-color DNA sequencing by synthesis can be designed by attaching a cleavable fluorophore to the base and capping the 3'-OH with a small chemically reversible moiety so that they are still recognized by DNA polymerase as substrates. Further optimization of the approach will lead to even longer sequencing readlengths.

Design and Synthesis of Chemically Cleavable Fluorescent Nucleotide Analogues as Reversible Terminators for SBS.

Figure 2:
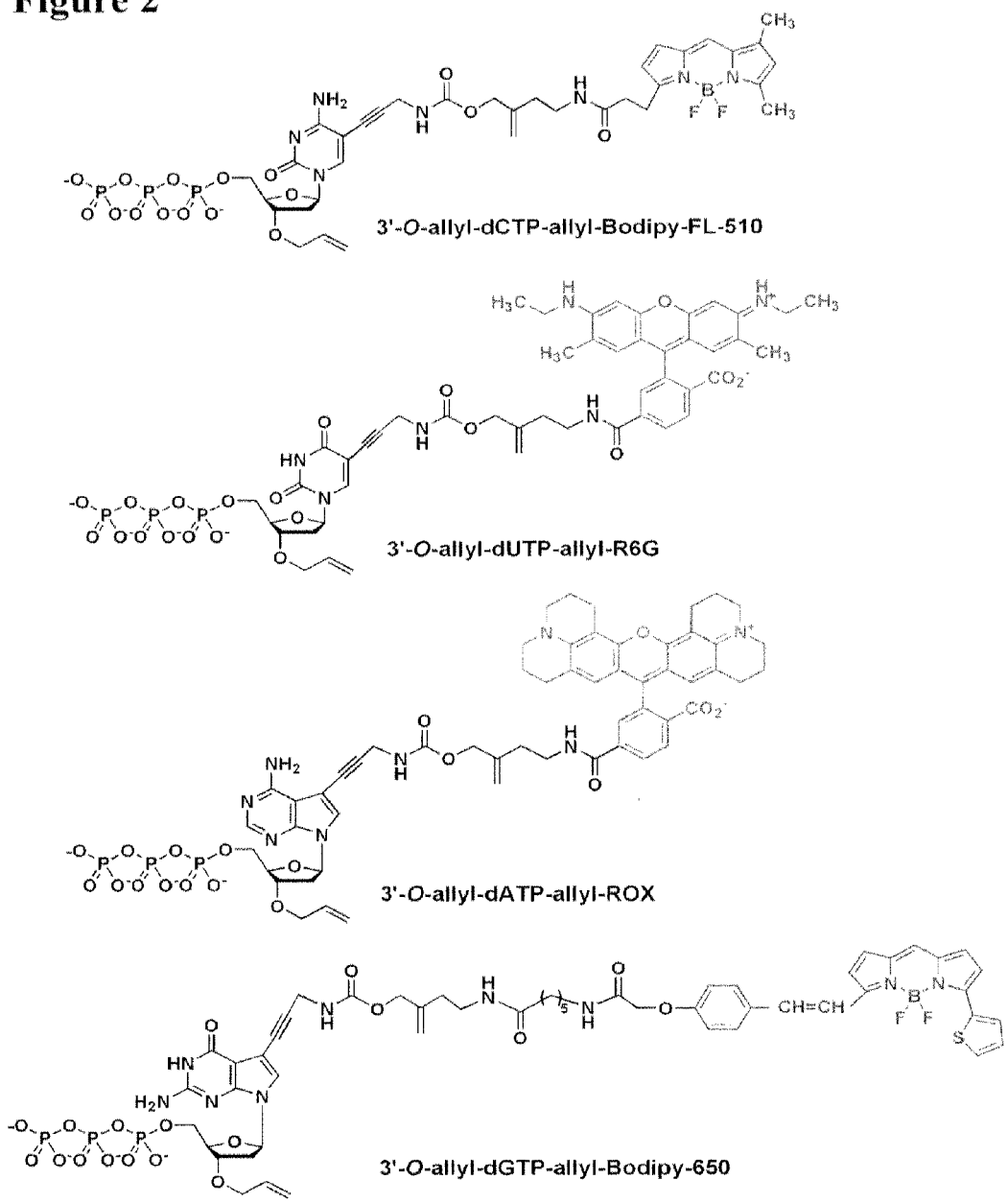
FIG. 2. Structures of 3'-O-allyl-dCTP-allyl-Bodipy-FL-510 ($\lambda_{abs\,(max)}$=502 nm; $\lambda_{em\,(max)}$=510 nm), 3-O-allyl-dUTP-allyl-R6G ($\lambda_{abs\,(max)}$=525 nm; =550 nm), 3'-O-allyl-dATP-allyl-ROX ($\lambda_{abs\,(max)}$=585 nm; $\lambda_{em\,(max)}$=602 nm), and 3'-O-allyl-dGTP-allyl-Bodipy-650 ($\lambda_{abs\,(max)}$=630 nm; $\lambda_{em\,(max)}$=650 nm).

To demonstrate the feasibility of carrying out de novo DNA sequencing by synthesis on a chip, four chemically cleavable fluorescent nucleotide analogues (3'-O-allyl-dCTP-allyl-Bodipy-FL-510, 3'-O-allyl-dUTP-allyl-R6G, 3'-O-allyl-dATP-allyl-ROX and 3'-O-allyl-dGTP-allyl-Bodipy-650/Cy5) (FIG. 2) were designed and synthesized as reversible terminators for DNA polymerase reaction. Modified DNA polymerases have been shown to be highly tolerant to nucleotide modifications with bulky groups at the 5-position of pyrimidines (C and U) and the 7-position of purines and G). Thus, each unique fluorophore was attached to the 5 position of C/U and the 7 position of A/G through an allyl carbamate linker. However, due to the close proximity of the 3' position on the sugar ring of a nucleotide to the amino acid residues of the active site of the DNA polymerase, a relatively small allyl moiety was chosen as the 3'-OH reversible capping group. It was found that the fluorophore and the 3'-O-allyl group on a DNA extension product, which is generated by incorporation of the chemically cleavable fluorescent nucleotide analogues, are removed simultaneously in 30 seconds by Pd-catalyzed deallylation in aqueous solution. This one-step dual-deallylation reaction thus allows the re-initiation of the polymerase reaction. The detailed synthesis procedure and characterization of the 4 novel nucleotide analogues in FIG. 2 are described in Materials and Methods.

Figure 3:
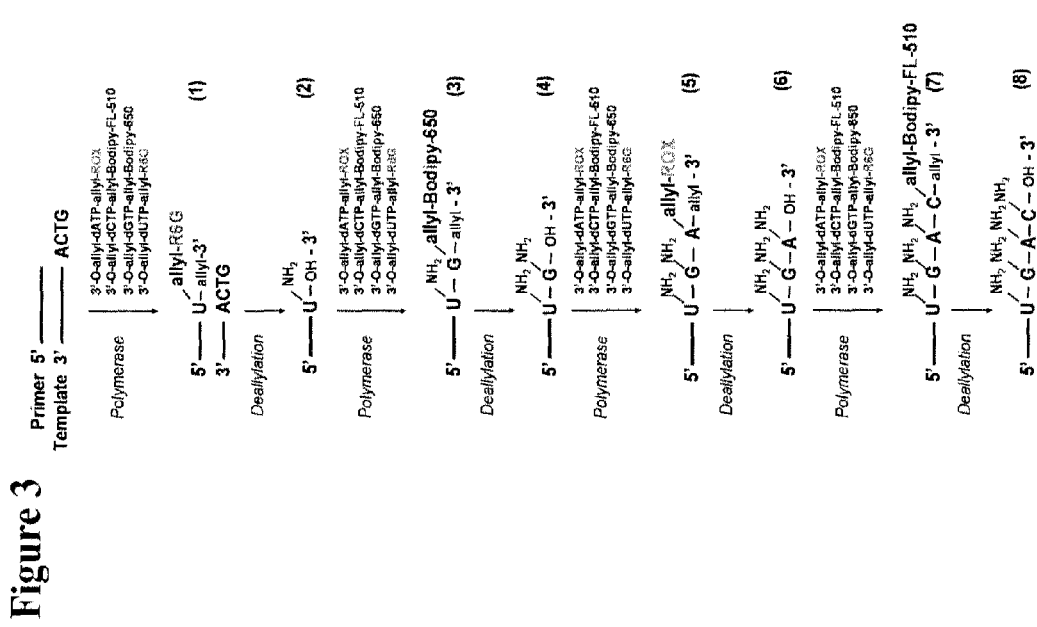
FIG. 3. The polymerase extension scheme (left) and MALDI-TOF MS spectra of the four consecutive extension products and their deallylated products (right). Primer extended with 3'-O-allyl-dUTP-allyl-R6G (1), and its deallylated product 2; Product 2 extended with 3'-O-allyl-dGTP-allyl-Bodipy-650 (3), and its deallylated product 4; Product 4 extended with 3'-O-allyl-dATP-allyl-ROX (5), and its deallylated product 6; Product 6 extended with 3'-O-allyl-dCTP-allyl-Bodipy-FL-510 (7), and its deallylated product 8. After 30 seconds of incubation with the palladium/TPPTS cocktail at 70° C., deallylation is complete with both the fluorophores and the 3'-O-allyl groups cleaved from the extended DNA products.
Figure 4:
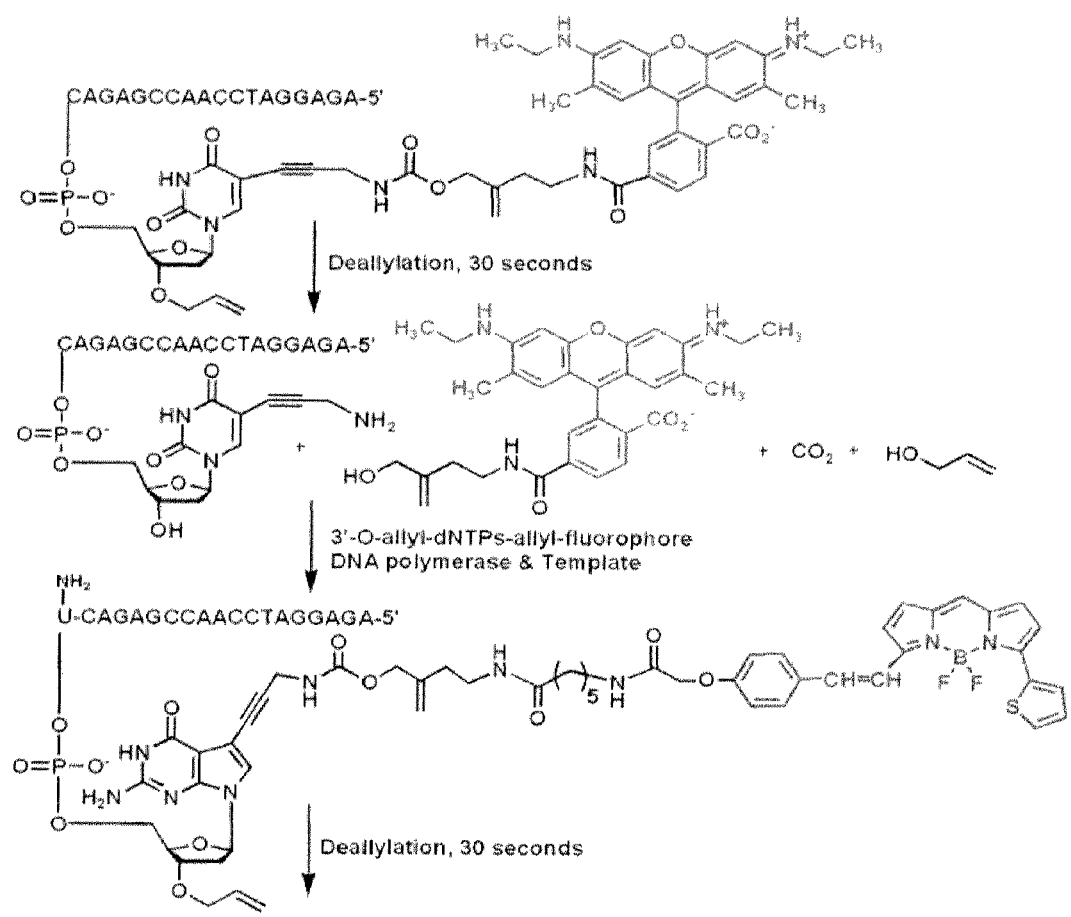
FIG. 4. DNA extension reaction performed in solution phase to characterize the four different chemically cleavable fluorescent nucleotide analogues (3'-O-allyl-dUTP-allyl-R6G, 3'-O-allyl-dGTP-allyl-Bodipy-650, 3'-O-allyl-dATP-allyl-ROX and 3'-O-allyl-dCTP-allyl-Bodipy-FL-510). After each extension reaction, the DNA extension product is purified by HPLC for MALDI-TOF MS measurement to verify that it is the correct extension product. Pd-catalyzed deallylation reaction is performed to produce a DNA product that is used as a primer for the next DNA extension reaction.
Figure 4:
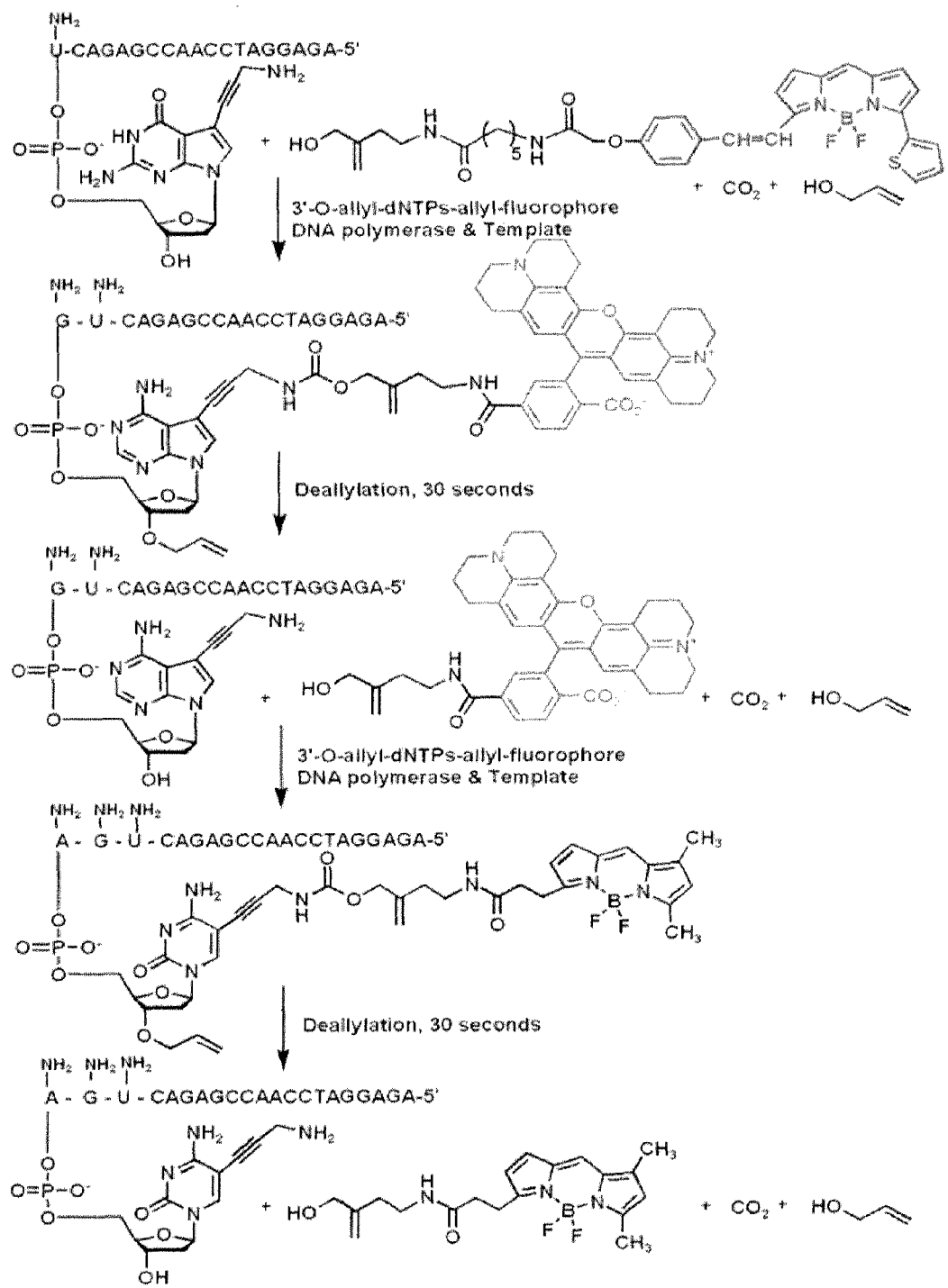

In order to verify that these fluorescent nucleotide analogues are incorporated accurately in a base-specific manner in a polymerase reaction, four continuous steps of DNA extension and deallylation were carried out in solution. This allows the isolation of the DNA product at each step for detailed molecular structure characterization by MALDI-TOF mass spectrometry (MS) as shown in FIG. 3. The first extension product 5'-U(allyl-R6G)-3'-O-allyl (1) was purified by HPLC and analyzed using MALDI-TOF MS [FIG. 3(A)]. This product was then deallylated using a Pd-catalyzed deallylation cocktail [1× Thermopol I reaction buffer/ $Na_2PdCl_4$/P(PhSO$_3$Na)$_3$]. The active Pd catalyst is generated from $Na_2PdCl_4$ and a ligand P(PhSO$_3$Na)$_3$ (TPPTS) to mediate the deallylation reaction in DNA compatible aqueous condition to simultaneously cleave both the fluorophore and the 3'-O-allyl group (28). The deallylated product (2) was also analyzed using MALDI-TOF MS [FIG. 3(B)]. As can be seen from FIG. 3(A), the MALDI-TOF MS spectrum consists of a distinct peak at m/z 6469 corresponding to the DNA extension product 5'-U(allyl-R6G)-3'-O-allyl (1), which confirms that the nucleotide analogue can be incorporated base specifically among pool of all four (A, C, G, T) by DNA polymerase into a growing DNA strand. FIG. 3(B) shows the deallylation result of the above DNA product. The peak at m/z 6469 has completely disappeared while the peak corresponding to the dual deallylated product 5'-U (2) appears as the sole dominant peak at m/z 5870, which establishes that the Pd-catalyzed deallylation reaction completely cleaves both the fluorophore and the 3'-O-allyl group with high efficiency without damaging the DNA. The next extension reaction was carried out using this deallylated DNA product with a free 3'-OH group regenerated as a primer along with four allyl modified fluorescent nucleotide mixture to yield an extension product 5'-UG(allyl-Bodipy-650)-3'-O-allyl (3). As described above, the extension product 3 was analyzed by MALDI-TOF MS producing a dominant peak at m/z 6984 [FIG. 3(C)], and then deallylated for further MS analysis yielding a single peak at m/z 6256 (product 4) [FIG. 3(D)]. The third extension reaction yielding 5'-UGA(allyl-ROX)-3'-O-allyl (5), the fourth extension reaction yielding 5'-UGAC(allyl-Bodipy-FL-510)-3'-O-allyl (7) and their deallylation reactions to yield products 6 and 8 were similarly carried out and analyzed by MALDI-TOF MS as shown in FIGS. 3(E), 3(F), 3(G) and 3(H). The chemical structures of the extension and cleavage products for each step are shown in FIG. 4. These results demonstrate that the above-synthesized 4 chemically cleavable fluorescent nucleotide analogues are successfully incorporated with high fidelity into the growing DNA strand in a polymerase reaction, and furthermore, both the fluorophore and the 3'-O-allyl group are efficiently removed by using a Pd-catalyzed deallylation reaction, which makes it feasible to use them for SBS on a chip.

Figure 5:
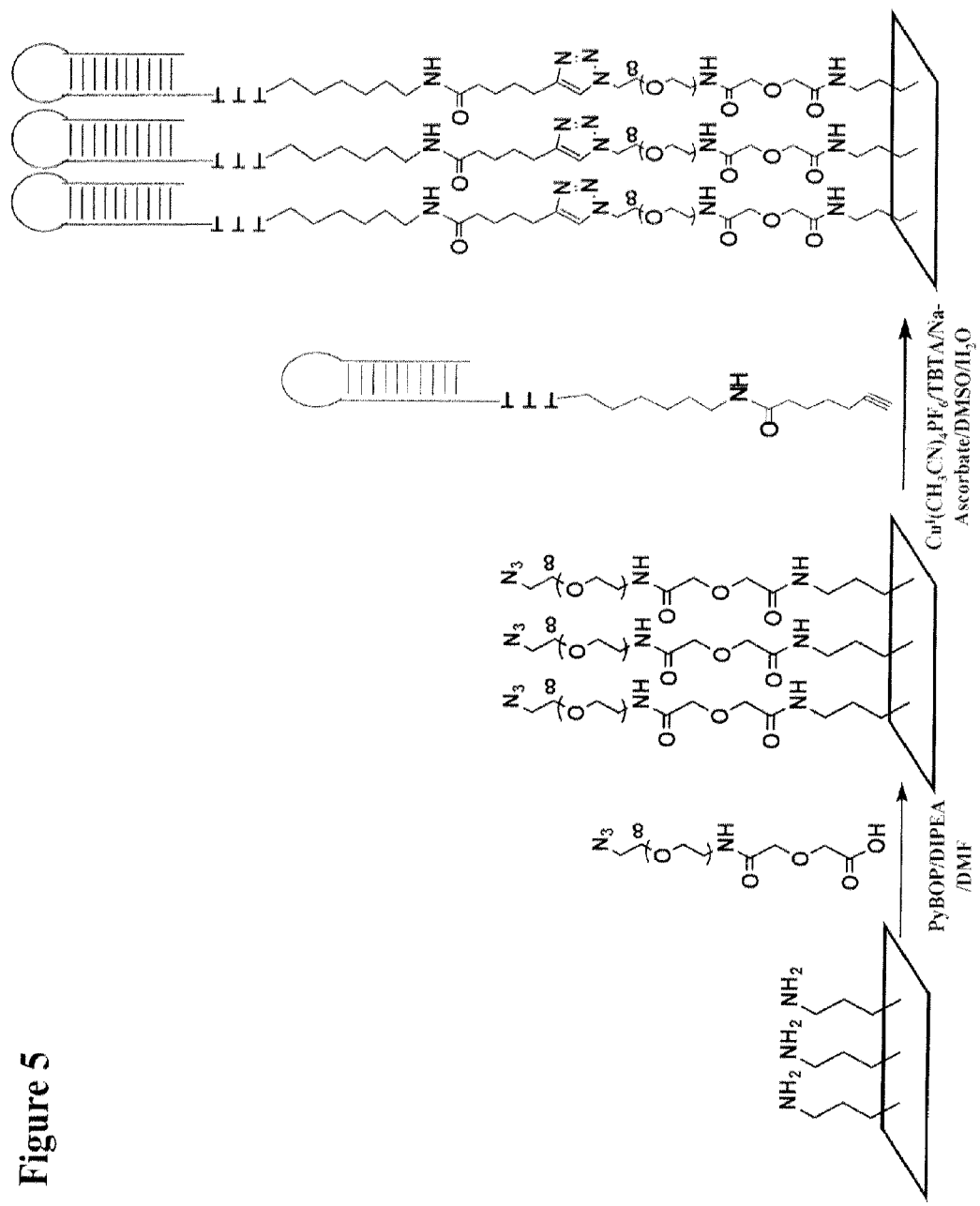
FIG. 5. Preparation of azide-functionalized glass chip through a PEG linker for the immobilization of alkyne labeled self-priming DNA template for SES.

4-Color DNA Sequencing with Chemically Cleavable Fluorescent Nucleotide Analogues as Reversible Terminators on a DNA Chip The chemically cleavable fluorescent nucleotide analogues were then used in an SBS reaction to identify the sequence of the DNA template immobilized on a solid surface. A site-specific 1,3-dipolar cycloaddition coupling chemistry was used to covalently immobilize the alkyne-labeled self-priming DNA template on the azido-functionalized surface in the presence of a Cu(I) catalyst. The principal advantage offered by the use of a self-priming moiety as compared to using separate primers and templates is that the covalent linkage of the primer to the template in the self-priming moiety prevents any possible dissociation of the primer from the template during the process of SBS. To prevent non-specific absorption of the unincorporated fluorescent nucleotides on the surface of the chip, a PEG linker is introduced between the DNA templates and the chip surface (FIG. 5). This approach was shown to produce very low background fluorescence after cleavage to remove the fluorophore as demonstrated by the DNA sequencing data described below.

Figure 6:
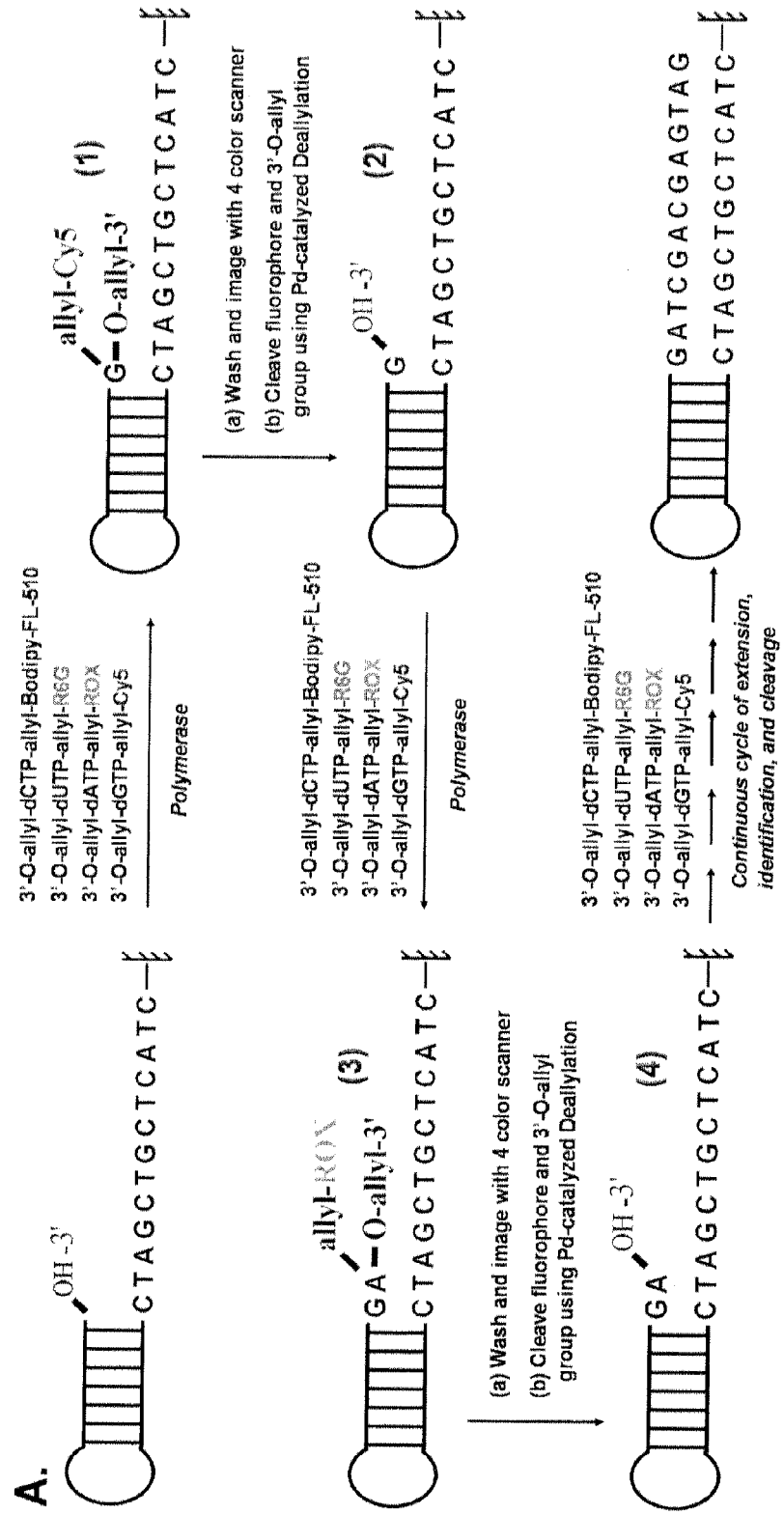
FIG. 6. (A) Reaction scheme of SBS on a chip using four chemically cleavable fluorescent nucleotides. (B) The scanned 4-color fluorescence images for each step of SES on a chip: (1) incorporation of 3'-O-allyl-dGTP-allyl-Cy5; (2) cleavage of allyl-Cy5 and 3'-allyl group; (3) incorporation of 3'-O-allyl-dATP-allyl-ROX; (4) cleavage of allyl-ROX and 3'-allyl group; (5) incorporation of 3'-O-allyl-dUTP-allyl-R6G; (6) cleavage of allyl-R6G and 3'-allyl group; (7) incorporation of 3'-O-allyl-dCTP-allyl-Bodipy-FL-510; (8) cleavage of allyl-Bodipy-FL-510 and 3'-allyl group; images (9) to (25) are similarly produced. (C) A plot (4-color sequencing data) of raw fluorescence emission intensity at the four designated emission wavelength of the four chemically cleavable fluorescent nucleotides.
Figure 6:
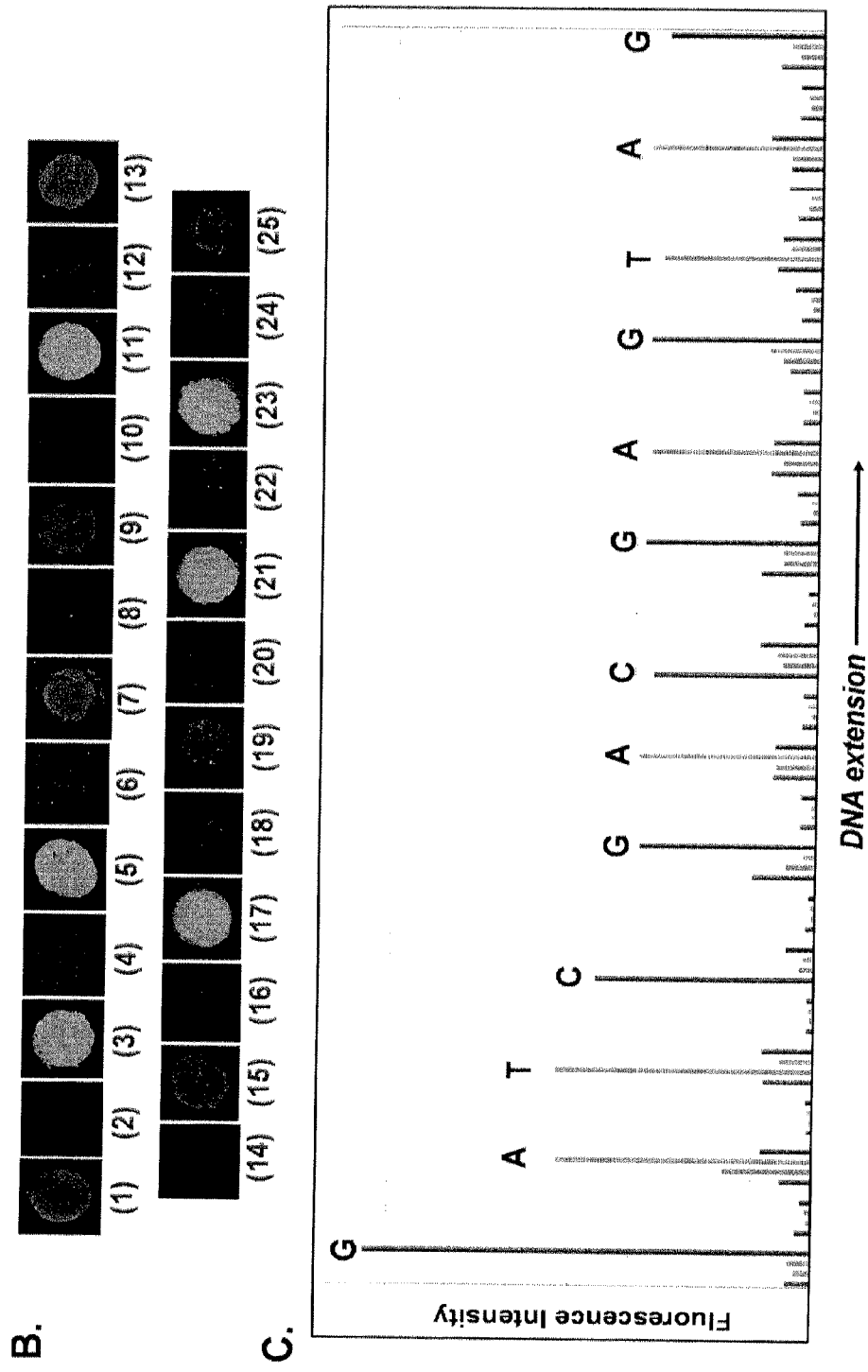
Figure 7:
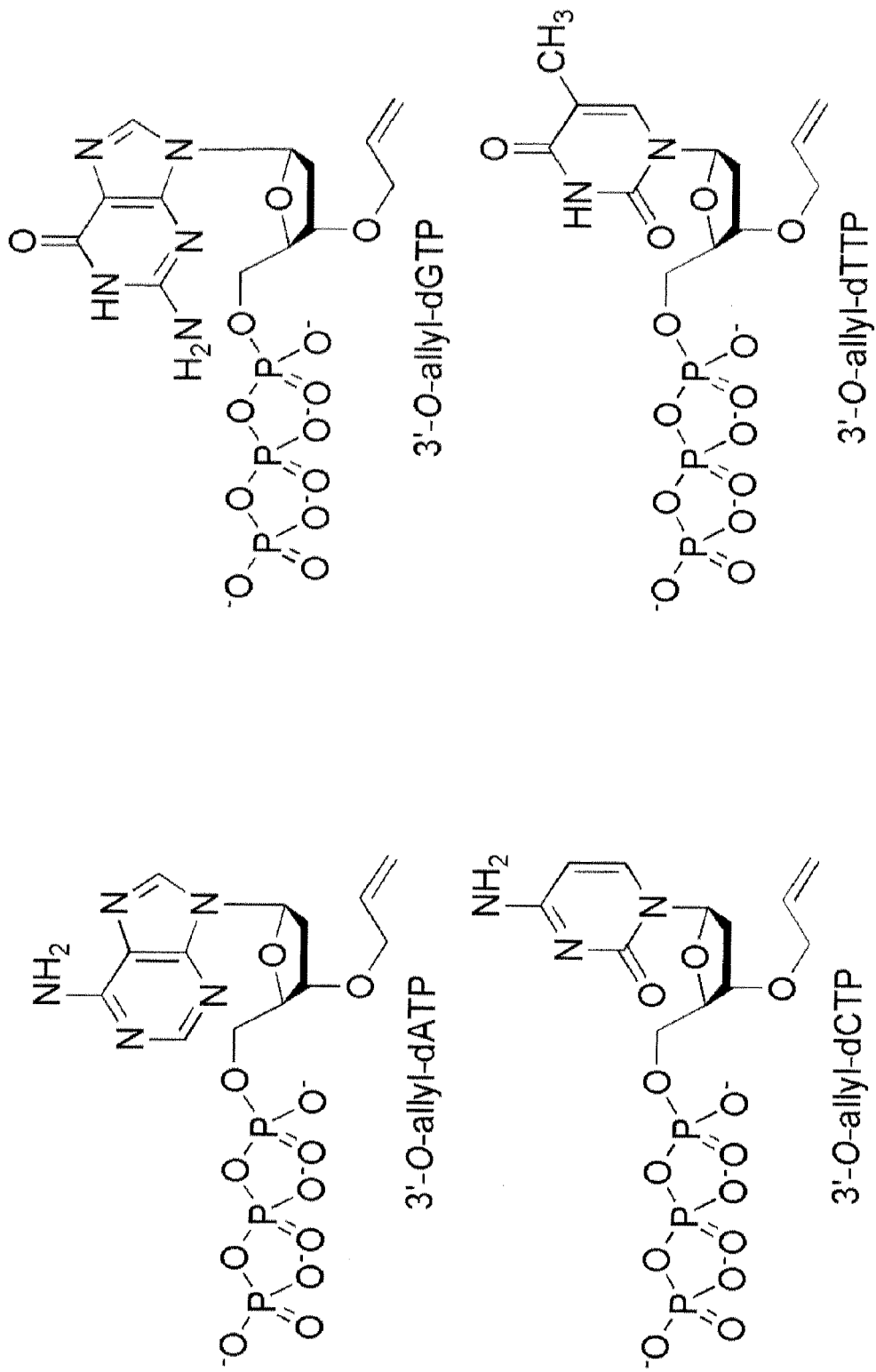
FIG. 7. Structures of 3'-O-allyl-dATP, 3'-O-allyl-dCTP, 3'-O-allyl-dGTP, and 3'-O-allyl-dTTP.

SBS was first performed on a chip-immobilized DNA template that has no homopolymer sequences using the four chemically cleavable fluorescent nucleotide reversible terminators (3'-O-allyl-dCTP-allyl-Bodipy-FL-510, 3'-O-allyl-dUTP-allyl-R6G, 3'-O-allyl-dATP-allyl-ROX and 3'-O-allyl-dGTP-allyl-Cy5) and the results are shown in FIG. 6. The structure of the self-priming DNA moiety is shown schematically in FIG. 6A, with the first 13 nucleotide sequences immediately after the priming site. The de novo sequencing reaction on the chip was initiated by extending the self-priming DNA using a solution containing all four 3'-O-allyl-dNTPs-allyl-fluorophore, and a 9°N mutant DNA polymerase. In order to negate any lagging fluorescence signal that is caused by previously unextended priming strand, a synchronization step was added to reduce the amount of unextended priming strands after the extension with the fluorescent nucleotides. A synchronization reaction mixture consisting of all four 3'-O-allyl-dNTPs (FIG. 7), which have a higher polymerase incorporation efficiency due to the lack of a fluorophore compared to the bulkier 3'-O-allyl-dNTPs-allyl-fluorophore, was used along with the 9° N mutant DNA polymerase to extend any remaining priming strand that has a free 3'-OH group to synchronize the incorporation. The extension by 3'-O-allyl-dNTPs also enhances the enzymatic incorporation of the next nucleotide analogue, because after cleavage to remove the 3'-O-allyl group, the DNA product extended by 3'-O-allyl-dNTPs carry no modification groups. After washing, the extension of the primer by only the complementary fluorescent nucleotide was confirmed by observing a red signal (the emission from Cy5) in a 4-color fluorescent scanner [FIG. 6B (1)]. After detection of the fluorescent signal, the chip surface was immersed in a deallylation cocktail [1× Thermolpol I reaction buffer/$Na_2PdCl_4$/P($PhSO_3Na$)$_3$] and incubated for 5 min at 60° C. to cleave both the fluorophore and 3'-O-allyl group simultaneously. The chip was then immediately immersed in a 3 M Tris-HCl buffer (pH 8.5) and incubated for 5 min at 60° C. to remove the Pd complex. The surface was then washed, and a negligible residual fluorescent signal was detected to confirm cleavage of the fluorophore. This was followed by another extension reaction using 3'-O-allyl-dNTPs-allyl-fluorophore mixture to incorporate the next fluorescent nucleotide complementary to the subsequent base on the template. The entire process of incorporation, synchronization, detection and cleavage was performed multiple times using the four chemically cleavable fluorescent nucleotide reversible terminators to identify 13 successive bases in the DNA template. The fluorescence image of the chip for each nucleotide addition is shown in FIG. 6B, while a plot of the fluorescence intensity vs. the progress of sequencing extension (raw 4-color sequencing data) is shown in FIG. 6C. The DNA sequences are unambiguously identified from the 4-color raw fluorescence data without any processing.

Comparison of 4-Color SBS with Pyrosequencing.

Figure 8:
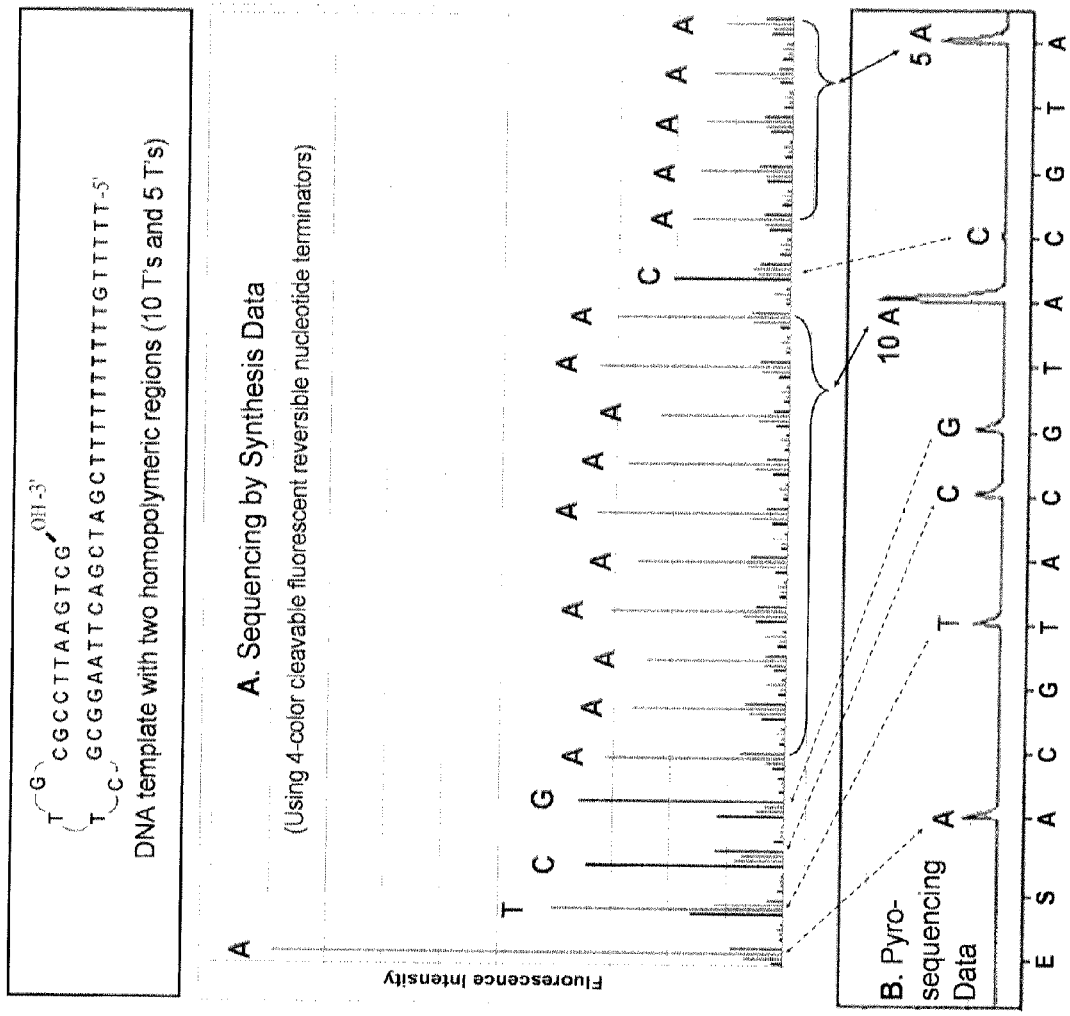
FIG. 8. (A) 4-color DNA sequencing raw data with our sequencing by synthesis chemistry using a template containing two homopolymeric regions. The individual base (A, T, C, G), the 10 repeated A's and the 5 repeated A's are clearly identified. The small groups of peaks between the identified bases are fluorescent background from the DNA chip, which does not build up as the cycle continues. (B) The pyrosequencing data of the same DNA template containing the homopolymeric regions (10 T's and 5 T's). The first 4 individual bases are clearly identified. The two homopolymeric regions (10 A's) and (5 A's) produce two large peaks, making it very difficult to determine the exact sequence from the data.

To further verify the advantage of SBS method using the four chemically cleavable fluorescent nucleotide reversible terminators, we carried out similar sequencing reaction as described above on a DNA template which contained two separate homopolymeric regions (stretch of 10 T's and 5 T's) as shown in FIG. 8 (panel A). These sequencing raw data were produced by adding all 4 fluorescent nucleotide reversible terminators together to the DNA template immobilized on the chip followed by synchronization reaction with four 3'-O-allyl-dNTPs, detecting the unique fluorescence emission for sequence determination, then cleaving the fluorophore and the 3'-O-allyl group in one step to continue the sequencing cycles. All 20 bases including the individual base (A, T, C, G), the repeated A's and the 5 repeated A's are clearly identified. The small groups of peaks between the identified bases are fluorescent background from the DNA chip, which does not build up as the cycle continues. Panel B in FIG. 8 shows the pyrosequencing data of the same DNA template containing the homopolymeric sequences. The first 4 individual bases are clearly identified. The two homopolymeric regions (10 A's) and (5 A's) produce two large peaks, but it is very difficult to identify the exact sequence from the data.

Conclusion

Four novel chemically cleavable fluorescent nucleotide analogues have been synthesized and characterized and have been used to produce a 4-color de novo DNA sequencing data on a chip. In doing so, two critical requirements for using SBS method to sequence DNA have been achieved unambiguously. First, a strategy to use a chemically reversible moiety to cap the 3'-OH group of the nucleotide has been successfully implemented so that the nucleotide terminates the polymerase reaction to allow the identification of the incorporated nucleotide. In addition these reversible terminators allow for the addition of all four nucleotides simultaneously in performing SBS. This ultimately reduces the number of cycles needed to complete the sequencing cycle, increases sequencing accuracy due to competition of the 4 nucleotides in the polymerase reaction, and enables accurate determination of homopolymeric regions of DNA template. Second, efficient removal of both the fluorophore and the 3'-OH capping group after the fluorescence signal detection have successfully been carried out which increases the overall efficiency of SBS.

The key factor governing the sequencing readlength of our 4-color SBS approach is the stepwise yield that are determined by the nucleotide incorporation efficiency and the yield of the cleavage of the fluorophore and the 3'-OH capping group from the DNA extension products. This stepwise yield here is ~99% based on measurement of the DNA products in solution phase. The yield on the surface is difficult to measure precisely due to fluctuations in the fluorescence imaging using the current manual fluorescent scanner. The strong fluorescence signal even for the 20$^{th}$ base shown in FIG. 8 indicates that we should be able to extend the readlength even further. In terms of readlength, Sanger sequencing is still the gold standard with readlength of over 800 bp but limited in throughput and cost. The readlength of pyrosequencing is ~100 bp but with high error rate due to difficulty in accurately determining the sequences of homopolymers. The 4-color SBS readlength on a manual fluorescent scanner is currently at ~20 bp with high accuracy. This readlength will increase with automation of the extension, cleavage and washing steps. The DNA polymerases and fluorescent labeling used in the automated 4-color Sanger sequencing method have undergone almost two decades of consistent incremental improvements after the basic fluorescent Sanger methods were established (2, 3). Following the same route, it is expected that the basic principle and strategy outlined in our 4-color SBS method will stimulate further improvement of the sequencing by synthesis methodology with engineering of high performance polymerases tailored for the cleavable fluorescent nucleotide terminators and testing alternative linkers and 3'-OH reversible capping moiety. It has been well established that using emulsion PCR on microbeads, millions of different DNA templates are immobilized on a surface of a chip (11, 16). This high density DNA templates coupled with our 4-color SBS approach will generate a high-throughput (>20 millions bases/chip) and high-accurate platform for a variety of sequencing and digital gene expression analysis projects.

Materials and Methods $^1$H NMR spectra were recorded on a Bruker DPX-400 (400 MHz) spectrometer and reported in ppm from a CD$_3$OD or DMSO-d internal standard (3.31 or 2.50 ppm respectively). Data were reported as follows: (s=singlet, d=doublet, t=triplet, q=quartet, m=multiplet, dd=doublet of doublets, ddd=doublet of doublets of doublets; coupling constant(s) in Hz; integration; assignment). Proton decoupled $^{13}$C NMR spectra were recorded on a Bruker DPX-400 (100 MHz)

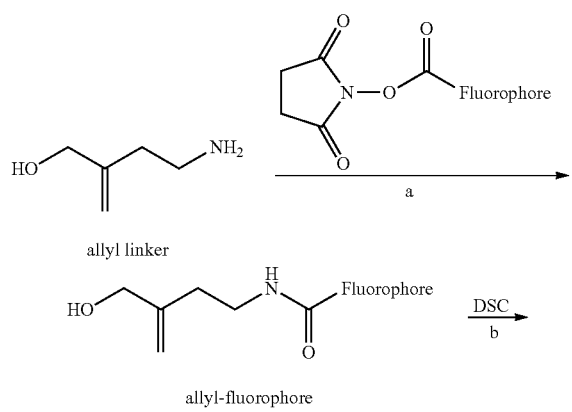

allyl linker allyl-fluorophore

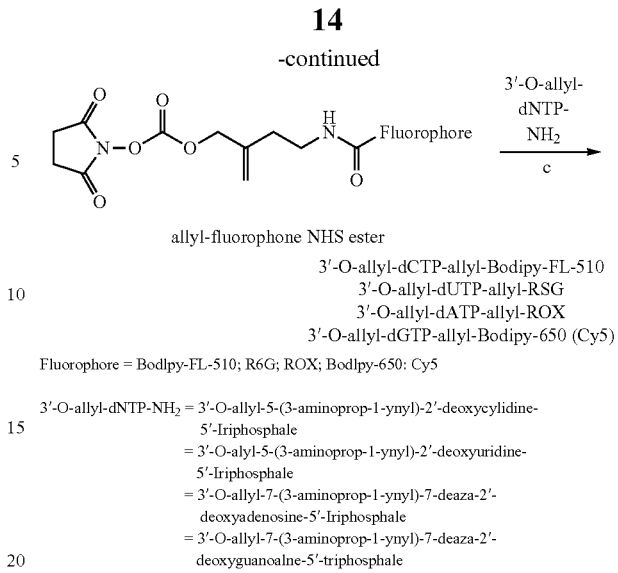

allyl-fluorophone NHS ester

3'-O-allyl-dCTP-allyl-Bodipy-FL-510
3'-O-allyl-dUTP-allyl-RSG
3'-O-allyl-dATP-allyl-ROX
3'-O-allyl-dGTP-allyl-Bodipy-650 (Cy5)

Fluorophore = Bodlpy-FL-510; R6G; ROX; Bodlpy-650: Cy5

3'-O-allyl-dNTP-NH$_2$ = 3'-O-allyl-5-(3-aminoprop-1-ynyl)-2'-deoxycylidine-5'-Iriphosphale
= 3'-O-alyl-5-(3-aminoprop-1-ynyl)-2'-deoxyuridine-5'-Iriphosphale
= 3'-O-allyl-7-(3-aminoprop-1-ynyl)-7-deaza-2'-deoxyadenosine-5'-Iriphosphale
= 3'-O-allyl-7-(3-aminoprop-1-ynyl)-7-deaza-2'-deoxyguanoalne-5'-triphosphale Synthetic scheme to prepare the chemically cleavable fluorescent nucleotides. a, DMF/1 M NaHCO$_3$ solution; b, N'-disuccinimidyl carbonate (DSC), triethylamine; c, 0.1 M NaHCO$_3$/Na$_2$CO$_3$ aqueous buffer (pH 8.7) spectrometer and reported in ppm from a CD$_3$OD, DMSO-d$_6$ or CDCl$_3$ internal standard (49.0, 39.5 or 77.0 ppm respectively). Proton decoupled $^{31}$P NMR spectra were recorded on a Bruker DPX-300 (121.4 MHz) spectrometer and reported in ppm from an 85% H$_3$PO$_4$ external standard. High Resolution Mass Spectra (HRMS) were obtained on a JEOL JMS HX 110A mass spectrometer. Compounds 30 and 32 were purchased from Berry & Associates. All Dye NHS esters were purchased from Molecular Probes and GE Healthcare. All other chemicals were purchased from Sigma-Aldrich.

I. Synthesis of 3'-O-allyl-dNTPs-allyl-Fluorophore

Chemically cleavable fluorescent nucleotides 3'-O-allyl-dCTP-allyl-Bodipy-FL-510, 3'-O-allyl-dUTP-allyl-R6G, 3'-O-allyl-dATP-allyl-ROX, 3'-O-allyl-dGTP-allyl-Bodipy-650 and 3'-O-allyl-dGTP-allyl-Cy5 were synthesized according to the above Scheme. A chemically cleavable linker 4-amino-2-methylene-1-butanol (allyl-linker) was reacted with the N-hydroxysuccinimide (NHS) ester of the corresponding fluorescent dye to produce an intermediate allyl-fluorophore, which was converted to an allyl-fluorophore NHS ester by reacting with N,N'-disuccinimidyl carbonate. The coupling reaction between the different allyl-fluorophore NHS esters and 3'-O-allyl-dNTPs-NH$_2$ produced the four chemically cleavable fluorescent nucleotides.

1. Synthesis of Allyl-Linker

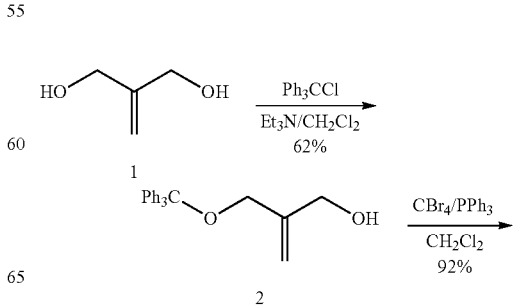

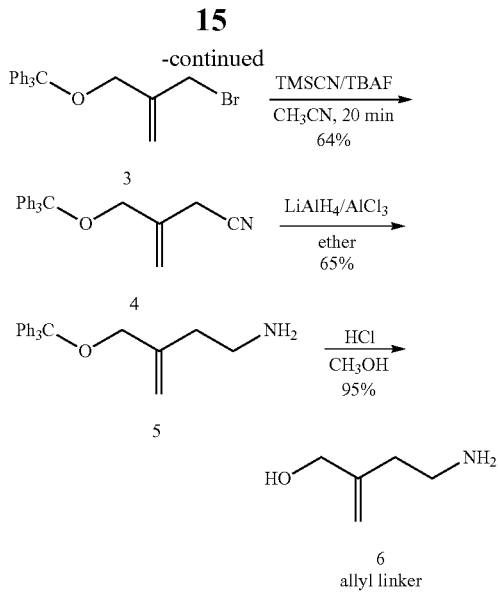

2-Triphenylmethoxymethyl-2-propen-1-ol (2). To a stirred solution of trityl chloride (4.05 g; 14.3 mmol) and 2-methylenepropane-1,3-diol 1 (1.20 mL; 14.3 mmol) in dry $CH_2Cl_2$ (20 mL), triethylamine (4.0 mL; 28.5 mmol) was added slowly at room temperature. The mixture was stirred at room temperature for 1 h, and then ethyl acetate (100 mL) and saturated aqueous $NaHCO_3$ (30 mL) were added. The organic phase was washed with saturated aqueous $NaHCO_3$, NaCl, and dried over anhydrous $Na_2SO_4$. After evaporation, the residue was purified by flash column chromatography using ethyl acetate-hexane (1:10~5) as the eluent to afford 2 as a white solid (2.89 g; 62% yield): $^1$H NMR (400 MHz, $CDCl_2$) δ 7.42-7.48 (m, 6H, six of ArH), 7.27-7.33 (m, 6H, six of ArH), 7.20-7.27 (m, 3H, three of ArH), 5.26 (s, 1H, one of $C=CH_2$), 5.17 (s, 1H, one of $C=CH_2$), 4.13 (d, J=6.1 Hz, 2H, $CH_2OH$), 3.70 (s, 2H, $Ph_3COCH_2$), 1.72 (t, J=6.1 Hz, 1H, $CH_2OH$); $^{13}$C NMR (100 MHz, $CDCl_3$) δ 145.4, 143.6, 128.3, 127.6, 126.8, 111.6, 87.0, 65.3, 64.5.

1-Bromo-2-triphenylmethoxymethyl-2-propene (3). To a stirred solution of 2 (2.56 g; 7.74 mmol) in $CH_2Cl_2$ (75 ml), $CBr_4$ (3.63 g; 10.83 mmol) and triphenylphosphine (2.47 g; 9.31 mmol) were added respectively at 0° C. The mixture was stirred at room temperature for 40 min.

Ethyl acetate (100 mL) and saturated aqueous $NaHCO_3$ (30 mL) were added at 0° C. The organic phase was washed with saturated aqueous NaCl, and dried over anhydrous $Na_2SO_4$. After evaporation, the residue was purified by flash column chromatography using $CH_2Cl_2$-hexane (1:5) as the eluent to afford 3 as white solid (3.02 g; 92% yield): $^1$H NMR (400 MHz, $CDCl_3$) δ 7.42-7.48 (m, 6H, six of ArH), 7.27-7.33 (m, 6H, six of ArH), 7.20-7.27 (m, 3H, three of ArH), 5.37 (s, 1H, one of $C=CH_2$), 5.31 (s, 1H, one of $C=CH_3$), 4.01 (s, 2H, $CH_2Br$), 3.75 (S, 2H, $Ph_3COCH_2$); $^{13}$C NMR (100 MHz, $CDCl_3$) δ 143.6, 142.6, 128.4, 127.6, 126.9, 115.8, 86.9, 64.2, 33.5.

3-Triphenylmethoxymethyl-3-butenonitrile (4). To a stirred solution of 3 (1.45 g; 3.69 mmol) and in dry $CH_3CN$ (37 mL), trimethylsilyl cyanide (0.49 mL; 3.69 mmol) was added. Then, 1 M tetrabutylammonium fluoride (TBAF) in THF solution (3.69 mL, 3.69 mmol) was added into the above reaction mixture slowly at room temperature. The mixture was stirred for 20 min. After evaporation, the residue was diluted with ethyl acetate (100 mL) and saturated aqueous $NaHCO_3$ (30 mL). The organic phase was washed with saturated aqueous NaCl and dried over anhydrous $Na_2SO_4$. After evaporation, the residue was purified by flash column chromatography using acetate-hexane (1:10) as the eluent to afford 4 as white solid (1.01 g; 64% yield):
$^1$H NMR (400 MHz, $CDCl_3$) δ 7.39-7.45 (m, 6H, six of ArH), 7.21-7.34 (m, 9H, nine of ArH), 5.31 (s, 2H, $C=CH_2$), 3.64 (s, 2H, $Ph_3COCH_2$), 3.11 (s, 2H, $CH_2CN$); $^{13}$C NMR (100 MHz, $CDCl_3$) δ 143.3, 135.5, 128.2, 127.7, 126.9, 116.8, 114.7, 87.0, 65.7, 21.9.

3-Triphenylmethoxymethyl-3-buten-1-amine (5). To a stirred solution of $LiAlH_4$ (119 mg; 2.98 mmol) in dry ether (5 mL), $AlCl_3$ (400 mg; 2.94 mmol) was added slowly at 0° C. and the mixture was stirred for 15 min. The mixture of 4 (829 mg; 2.44 mmol) in dry ether (9 mL) was added and then continued to stir at 0° C. for another 3 h. Afterwards, 10% aqueous NaOH (10 mL) was added to quench the reaction. The organic phase was washed with saturated aqueous $NaHCO_3$, NaCl, and dried over anhydrous $K_2CO_3$. After evaporation, the residue was further purified by flash column chromatography using $CH_3OH$—$CH_2Cl_2$ (1:20~5) as the eluent to afford 5 as colorless oil (545 mg; 65% yield): $^1$H NMR (400 MHz, $CDCl_3$) δ 7.41-7.48 (m, 6H, six of ArH), 7.26-7.33 (m, 6H, six of ArH), 7.19-7.26 (m, 3H, three of ArH), 5.33 (s, 1H, one of $C=CH_2$), 4.96 (s, 1H, one of $C=CH_2$), 3.53 (s, 2H, $Ph_3COCH_2$), 2.70 (m, 2H, $CH_2CH_2NH_2$) 2.18 (t, J=6.7 Hz, 2H, $CH_2CH_2NH_2$), 2.06 (br s, 2H, $NH_2$); $^{13}$C NMR (100 MHz, $CDCl_3$) δ 143.6, 143.4, 128.1, 127.4, 126.5, 111.3, 86.5, 66.1, 39.8, 37.4; HRMS (FAB+) calcd for $C_{24}H_{26}ON$ (M+H$^+$): 344.2014. found: 344.2017.

4-Amino-2-methylene-1-butanol (6). To a stirred solution of 5 (540 mg; 1.57 mmol) in $CH_3OH$ (11 mL), HCl (2M solution in ether; 5.5 mL) was added at room temperature and the mixture was stirred for 1 h. Then 7M ammonia in $CH_3OH$ solution (2.7 mL) was added into the above mixture at room temperature and continued to stir for another 10 min. After filtration, the solid was washed with $CH_3OH$ and combined with the filtrate. After evaporation, the crude product was further purified by flash column chromatography using $CH_3OH$—$CH_2Cl_2$ (1:4) as the eluent to afford 6 as colorless oil (151 mg; 95% yield): $^1$H NMR (400 MHz, $CD_3OD$) δ 5.19 (s, 1H, one of $C=CH_2$), 5.01 (s, 1H, one of $C=CH_2$), 4.06 (s, 2H, $CH_2OH$), 3.10 (t, J=7.5 Hz, 2H, $CH_2CH_2NH_2$), 2.46 (t, J=7.5 Hz, 2H, $CH_2CH_2NH_2$); $^{13}$C NMR (100 MHz, $CD_3OD$) δ 145.3, 113.7, 65.5, 39.5, 32.0; MS (FAB+) calcd for $C_5H_{12}ON$ (M+H$^+$): 102.09. found: 102.12.

2. Synthesis of Allyl-Fluorophore

A general procedure for the synthesis of Allyl-Fluorophore is as follows. To a stirred solution of 6 (3.5 mg; 34.6 μmol) in DMF (450 μL), aqueous $NaHCO_3$ (1M solution; 100 μL) was added at room temperature. The mixture was stirred for 5 min. Dye NHS (N-hydroxysuccinimide) ester (5 mg) in DMF (450 μL) was added and then the mixture was stirred at room temperature for 6 h. The crude product was further purified by a preparative TLC plate using $CH_3OH$—$CH_2Cl_2$ as the eluent to afford Allyl-Fluorophore.

Allyl-Bodipy-FL-510 (7). $^1$H NMR (400 MHz, $CD_3OD$) δ 7.42 (s, 1H), 7.00 (d, J=4.0 Hz, 1H), 6.32 (d, J=4.0 Hz, 1H), 6.21 (s, 1H), 5.06 (s, 1H, one of $C=CH_2$), 4.87 (s, 1H, one of $C=CH_2$, partly superimposed by solvent signal), 4.01 (s, 2H, $CH_3OH$), 3.33 (t, J=7.5 Hz, 2H, partly superimposed by solvent signal), 3.21 (t, J=7.7 Hz, 2H), 2.59 (t, J=7.7 Hz, 2H), 2.51 (s, 3H, one of $ArCH_3$), 2.28 (s, 3H), 2.26 (t, J=7.1 Hz, 2H); HRMS (FAB+) calcd for $C_{19}H_{24}O_2N_3F_2B$ (M+): 375.1933. found: 375.1957.

Allyl-R6G (8). $^1$H NMR (400 MHz, CD$_3$OD) δ 8.12 (d, J=8.1 Hz, 1H), 8.05 (dd, J=1.8, 8.1 Hz, 1H), 7.66 (d, J=1.6 Hz, 1H), 7.02 (s, 2H), 6.88 (s, 2H), 5.08 (s, 1H, one of C=CH$_2$), 4.92 (s, 1H, one of C=CH$_2$), 4.06 (s, 2H, CH$_2$OH), 3.48-3.56 (m, 6H), 2.40 (t, J=7.2 Hz, 2H), 2.13 (s, 6H), 1.36 (t, J=7.2 Hz, 6H); HRMS (FAB+) calcd for C$_{22}$H$_{26}$O$_5$N$_3$ (M+H$^+$): 542.2655. found: 542.2648.

Allyl-ROX (9). $^1$H NMR (400 MHz, CD$_3$OD) δ 8.03 (d, J=8.1 Hz, 1H), 7.98 (dd, J=1.6, 8.1 Hz, 1H), 7.60 (d, J=1.4 Hz, 1H), 6.75 (s, 2H), 5.08 (s, 1H, one of C=CH$_2$), 4.91 (s, 1H, one of C=CHO), 4.05 (s, 2H, CH$_2$OH), 3.45-3.57 (m, 10H), 3.03-3.10 (m, 4H), 2.64-2.73 (m, 4H), 2.38 (t, J=7.1 Hz, 2H), 2.04-2.15 (m, 4H), 1.89-1.99 (m, 4H); HRMS (FAB+) calcd for C$_{38}$H$_{40}$O$_5$N$_3$ (M+H$^+$); 618.2968. found: 618.2961.

Allyl-Bodipy-650 (10). $^1$H NMR (400 MHz, CD$_3$OD) δ 8.12 (dd, J=0.9, 3.8 Hz, 1H), 7.63 (m, 3H), 7.54 (d, J=6.4 Hz, 2H), 7.35 (s, 1H), 7.18-7.22 (m, 2H), 7.12 (m, 2H), 7.06 (d, J=8.8 Hz, 2H), 6.85 (d, J=4.2 Hz, 1H), 5.06 (s, 1H, one of C=CH$_2$), 4.86 (s, 1H, one of C=CH$_2$), 4.56 (s, 2H), 4.00 (s, 2H, CH$_2$OH), 3.28 (m, 4H), 2.23 (t, J=7.1 Hz, 2H), 2.14 (t, J=7.5 Hz, 2H), 1.49-1.62 (m, 4H), 1.25-1.34 (m, 2H); HRMS (FAB+) calcd for C$_{34}$H$_{37}$O$_4$N$_4$F$_2$SB (M$^+$): 646.2603. found: 646.2620.

Allyl-Cy5 (11). $^1$H NMR (400 MHz, CD$_3$OD) 7.75-7.86 (m, 2H), 7.43-7.62 (m, 3H), 6.65 (m, 1H), 6.25-6.53 (m, 5H), 5.06 (s, 1H, one of C=CH$_2$), 4.86 (s, 1H, one of CαCH$_2$), 4.56 (s, 2H), 4.00 (s, 2H, CH$_2$OH), 3.28 (m, 6H), 2.03-2.40 (m, 4H), 1.55 (t, J=7.2 Hz, 3H), 1.31 (s, 6H), 1.26 (s, 6H), 1.25-1.64 (m, 6H); HRMS (FAB+) calcd for C$_{38}$H$_{48}$O$_8$N$_3$S$_2$ (M$^+$): 738.2888. found: 738.2867.

3. Synthesis of Allyl-Fluorophore NHS Ester

A general procedure for the synthesis of Allyl-Dye NHS ester is as follows. To a stirred solution of Allyl-Fluorophore (4 mg) in dry DMF (350 μL), DSC (8.0 mg; 31.2 μmol) and triethylamine (5.0 μL; 35.4 μmol) were added respectively. The reaction mixture was stirred at room temperature for 10 h. After evaporation, the crude product was further purified by flash column chromatography using CH$_3$OH—CH$_2$Cl$_2$ as the eluent to afford Allyl-Fluorophore NHS ester, which was used directly for the next step.

4. Synthesis of 3'-O-allyl-dCTP-allyl-Bodipy-FL-510 (23)

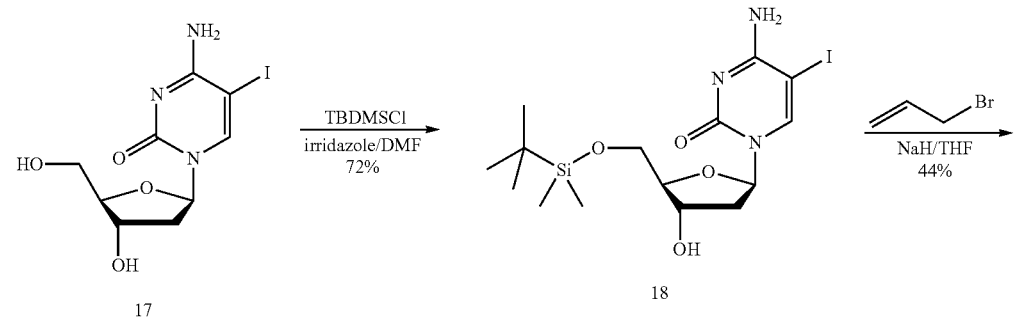

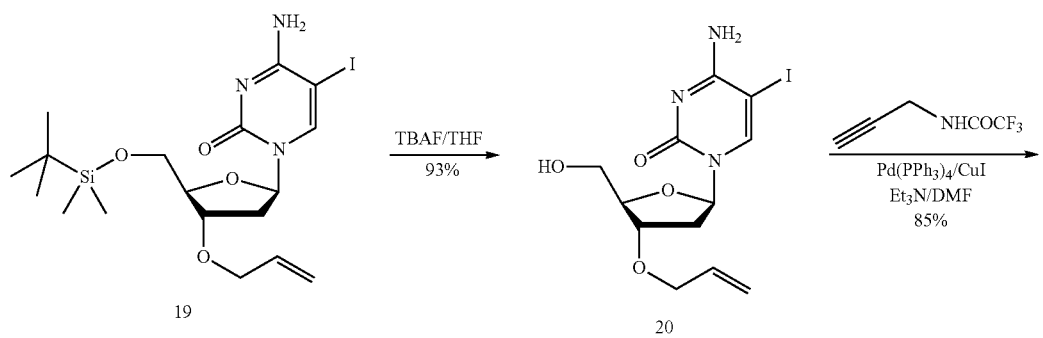

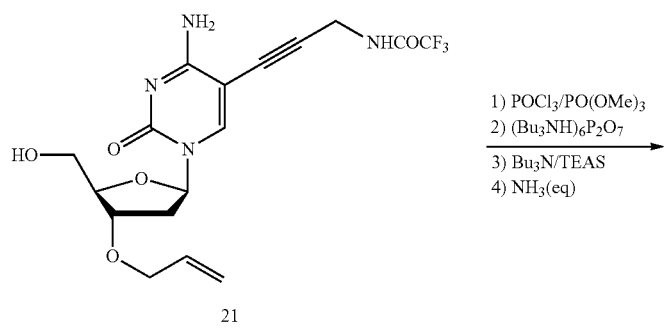

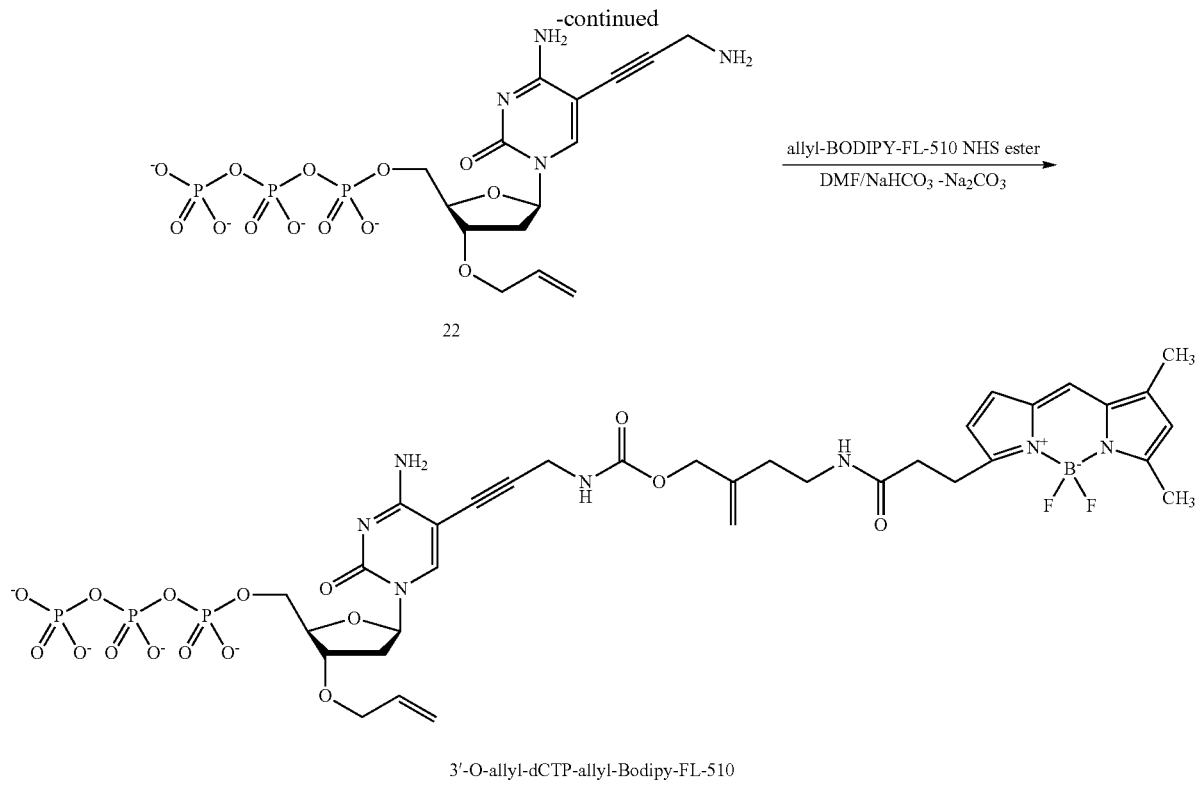

3'-O-allyl-dCTP-allyl-Bodipy-FL-510

5'-O-(tert-Butyldimethylsilyl)-5-iodo-2'-deoxycytidine (18). To a stirred mixture of 17 (1.00 g; 2.83 mmol) and imidazole (462 mg; 6.79 mmol) in anhydrous DMF (14.0 mL), tert-butyldimethylsilyl chloride (TBDMSCl) (510 mg; 3.28 mmol) was added. The reaction mixture was stirred at room temperature for 20 h. After evaporation, the residue was purified by flash column chromatography using $CH_3OH$—$CH_2Cl_2$ (1:20) as the eluent to afford 18 as white solid (1.18 g; 89% yield): $^1H$ NMR (400 MHz, $CD_3OD$) δ 8.18 (s, 1H, 6-H), 6.17 (dd, J=5.8, 7.5 Hz, 1H, 1'-H), 4.34 (m, 1H, 3'-H), 4.04 (m, 1H, 4'-H), 3.93 (dd, J=2.5, 11.6 Hz, 1H, one of 5'-H), 3.84 (dd, J=2.9, 11.6 Hz, 1H, one of 5'-H), 2.41-2.48 (ddd, J=2.5, 5.8, 13.5 Hz, 1H, one of 2'-H), 2.01-2.08 (ddd, J=5.9, 7.6, 13.5 Hz, 1H, one of 2'-H), 0.95 (s, 9H, $C(CH_3)_3$), 0.17 (s, 3H, one of $SiCH_3$), 0.16 (s, 3H, one of $SiCH_3$); $^{13}C$ NMR (100 MHz, $CD_3OD$) δ 165.5, 156.8, 147.8, 89.4, 88.3, 72.8, 64.6, 57.1, 43.1, 26.7, 19.4, −4.8, −4.9; HRMS (FAB+) calcd for $C_{15}H_{27}O_4N_3SiI$ ($M+H^+$): 468.0816. found: 468.0835.

3'-O-Allyl-5'-O-(tert-butyldimethylsilyl)-5-iodo-2'-deoxycytidine (19). To a stirred solution of 18 (1.18 g; 2.52 mmol) in anhydrous THF (43 mL), 95% NaH powder (128 mg; 5.07 mmol) was added. The suspension mixture was stirred at room temperature for 45 min. Allyl bromide (240 μL, 2.79 mmol) was then added at 0° C. and the reaction was stirred at room temperature for another 14 h with exclusion of moisture. Saturated aqueous $NaHCO_3$ (10 mL) was added at 0° C. and the reaction mixture was stirred for 10 min. After evaporation, the residue was dissolved in ethyl acetate (150 mL). The solution was then washed with saturated aqueous $NaHCO_3$ and NaCl, and dried over anhydrous $Na_3SO_4$. After evaporation, the residue was purified by flash column chromatography using ethyl acetate as the eluent to afford 19 as white solid (601 mg; 47% yield) $^1H$ NMR (400 MHz, $CD_3OD$) δ 8.15 (s, 1H, 6-H), 6.12 (dd, J=5.6, 8.0 Hz, 1H, 1'-H), 4.17 (m, 1H, 4'-H), 4.14 (m, 1H, 3'-H), 3.98-4.10 (m, 2H, $CH_2CH=CH_2$), 3.93 (dd, J=2.8, 11.5 Hz, 1H, one of 5'-H), 3.83 (dd, J=2.8, 11.5 Hz, 1H, one of 5'-H), 2.53-2.60 (ddd, J=1.7, 5.6, 13.6 Hz, 1H, one of 2'-H), 1.94-2.02 (ddd, J=5.9, 8.0, 13.6 Hz, 1H, one of 2'-H), 0.94 (s, 9H, $C(CH_3)_3$), 0.17 (s, 3H, one of $SiCH_3$), 0.16 (s, 3H, one of $SiCH_3$); $^{13}C$ NMR (100 MHz, $CD_3OD$) δ 165.4, 156.7, 147.7, 135.5, 117.2, 88.2, 87.0, 80.4, 70.9, 64.8, 57.3, 40.1, 26.7, 19.4, −4.7, −4.9; HRMS (FAB+) calcd for $C_{18}H_{31}O_4N_3SiI$ ($M+H^+$): 508.1129. found: 508.1123.

3'-O-Allyl-5-iodo-2'-deoxycytidine (20). To a stirred solution of 19 (601 mg; 1.18 mmol) in anhydrous THF (28 mL), 1 M TBAF in THF solution (1.31 mL; 1.31 mmol) was added and the reaction mixture was stirred at room temperature for 1 h. After evaporation, the residue was dissolved in ethyl acetate (100 mL). The solution was then washed with saturated aqueous NaCl and dried over anhydrous $Na_2SO_4$. After evaporation, the residue was purified by flash column chromatography using $CH_2OH$—$CH_2Cl_2$ (1:10) as the eluent to afford 20 as white crystals (329 mg; 71% yield): $^1H$ NMR (400 MHz, $CD_3OD$) δ 8.47 (s, 1H, 6-H), 6.15 (dd, J=6.2, 6.7 Hz, 1H, 1'-H), 5.87-5.98 (m, 1H, $CH_2CH=CH_2$), 5.26-5.33 (dm, J=17.2 Hz, 1H, one of $CH_2CH=CH_2$), 5.14-5.19 (dm, J=10.5 Hz, 1H, one of $CH_2CH=CH_2$), 4.18 (m, 1H, 3'-H), 4.08 (m, 1H, 4'-H), 3.98-4.10 (m, 2H, $CH_2CH=CH_2$), 3.82 (dd, J=3.2, 13.0 Hz, 1H, one of 5'-H), 3.72 (dd, J=3.3, 13.0 Hz, 1H, one of 5'-H), 2.44-2.51 (ddd, J=3.2, 6.0, 13.6 Hz, 1H, one of 2'-H), 2.07-2.15 (m, 1H, one of 2'-H); $^{13}C$ NMR (100 MHz, $CD_3OD$) δ 165.4, 156.9, 148.8, 135.6, 117.0, 87.9, 86.9, 79.6, 71.2, 62.7, 57.2, 39.7; HRMS (FAB+) calcd for $C_{12}H_{17}O_4N_3I$ ($M+H^+$): 394.0264. found: 394.0274.

3'-O-Allyl-5-{(3-[(trifluoroacetyl)amino]prop-1-ynyl}-2'-deoxycytidine (21). To a stirred solution of 20 (329 mg;

0.84 mmol) in anhydrous DMF (3.7 mL), tetrakis(triphenylphosphine)palladium(0) (97 mg; 0.084 mmol) and CuI (35 mg; 0.18 mmol) were added. The reaction mixture was stirred at room temperature for 10 min. Then N-propargyltrifluoroacetamide (379 mg; 2.51 mmol) and Et$_3$N (233 µL; 1.68 mmol) were added into the above reaction mixture. The reaction was stirred at room temperature for 1.5 h with exclusion of air and light. After evaporation, the residue was dissolved in ethyl acetate (100 mL). The mixture was washed with saturated aqueous NaHCO$_3$, NaCl, and dried over anhydrous Na$_2$SO$_4$. After evaporation, the residue was purified by flash column chromatography using CH$_3$OH—CH$_2$Cl$_2$ (0~1:10) as the eluent to afford 21 as yellow crystals (290 mg; 83% yield): $^1$H NMR (400 MHz, CD$_3$OD) δ 8.31 (s, 1H, 6-H), 6.17 (dd, J=6.0, 7.3 Hz, 1H, 1'-H), 5.87-5.97 (m, 1H, CH$_2$CH=CH$_2$), 5.26-5.33 (dm, J=17.3 Hz, 1H, one of CH$_2$CH=CH$_2$), 5.15-5.19 (dm, J=10.4 Hz, 1H, one of CH$_2$CH=CH$_2$), 4.31 (s, 2H, C=CCH$_2$), 4.17 (m, 1H, 3'-H), 4.09 (m, 1H, 4'-H), 3.98-4.10 (m, 2H, CH$_2$CH=CH$_2$), 3.80 (dd, J=3.4, 12.0 Hz, 1H, one of 5'-H), 3.72 (dd, J=3.6, 12.0 Hz, 1H, one of 5'-H), 2.46-2.53 (ddd, J=2.9, 5.3, 13.6 Hz, 1H, one of 2'-H), 2.04-2.12 (m, 1H, one of 2'-H); $^{13}$C NMR (100 MHz, CD$_3$OD) δ 166.0, 158.4 (q, J=38 Hz, COCF$_3$), 156.3, 145.8, 135.6, 117.1 (q, J=284 Hz, COCF$_3$), 117.0, 91.9, 90.7, 88.0, 87.0, 79.8, 75.5, 71.2, 62.8, 39.6, 31.0; HRMS (FAB+) calcd for C$_{17}$H$_{20}$O$_5$N$_4$F$_2$ (M+H$^+$): 417.1386. found: 417.1377.

3'-O-Allyl-5-(3-aminoprop-1-ynyl)-2'-deoxycytidine-5'-triphosphate (22). 21 (133 mg; 0.319 mmol) and proton sponge (83.6 mg; 0.386 mmol) were dried in a vacuum desiccator over P$_2$O$_5$ overnight before dissolving in trimethylphosphate (0.60 mL). Freshly distilled POCl$_3$ (36 µL; 0.383 mmol) was added dropwise at 0° C. and the mixture was stirred for 3 h. Then the solution of tributylammonium pyrophosphate (607 mg) and tributylamine (0.61 mL; 2.56 mmol) in anhydrous DMF (2.56 mL) was well vortexed and added in one portion at room temperature and the reaction mixture was stirred for 30 min. After that triethylammonium bicarbonate solution (TEAB) (0.1 M; 16 mL) was added and the mixture was stirred for 1 h. Then aqueous ammonia (28%; 16 mL) was added and the reaction mixture was stirred for 12 h. After most liquid was removed under vacuum, the residue was redissolved in water (2 mL) and filtered. The aqueous solution was purified by DEAE Sephadex A25 ion exchange column using gradient aqueous TEAB solution (from 0.1 M to 1.0 M) as eluent to afford 22 as colorless syrup after evaporation: $^1$H NMR (300 MHz, D$_3$O) δ 8.43 (s, 1H, 6-H), 6.21 (t, J=6.7 Hz, 1H, 1'-H), 5.85-6.00 (m, 1H, CH$_3$CH=CH$_2$), 5.28-5.38 (dm, J=17.3 Hz, 1H, one of CH$_2$CH=CH$_2$), 5.19-5.27 (dm, J=10.4 Hz, 1H, one of CH$_2$CH=CH$_2$), 4.22-4.41 (m, 3H, 3'-H and C=CCH$_2$), 4.05-4.18 (m, 3H, 4'-H and CH$_2$CH=CH$_2$), 3.94-4.01 (m, 2H, 5'-H), 2.47-2.59 (m, 1H, one of 2'-H), 2.20-2.32 (m, 1H, one of 2'-H); $^{31}$P NMR (121.4 MW, D$_2$O) δ −7.1 (d, J=19.8 Hz, 1P, γ-P), −11.1 (d, J=19.1 Hz, 1P, α-P), −21.9 (t, J=19.5 Hz, 1P, β-P).

3'-O-Allyl-dCTP-allyl-Bodipy-FL-510 (23). To a stirred solution of allyl-Bodipy-FL-510 NHS ester 12 in DMF (300 µL), 3'-O-allyl-dCTP-NH$_2$ 22 in 1M NaHCO$_3$—Na$_2$CO$_3$ buffer (300 µL; pH 8.7) was added. The reaction mixture was stirred at room temperature for 7 h and the crude product was purified by a preparative TLC plate using CH$_3$OH—CH$_2$Cl$_2$ (1:1) as the eluent. The crude product was further purified by reverse-phase HPLC using a 150×4.6 mm C18 column to afford compound 23 (retention time=35 min). Mobile phase: A, 4.4 mM Et$_3$N/98.3 mM 1,1,1,3,3,3-hexafluoro-2-propanol in water (pH=8.1); B, methanol. Elution was performed from 100% A isocratic over 10 min followed by a linear gradient of 0-50% B for 20 min and then 50% B isocratic over 20 min. The product was characterized by the following single base extension reaction to generate DNA extension product 24 and characterized by MALDI-TOF MS.

A general procedure of primer extension using 3'-O-allyl-dNTPs-allyl-Fluorophore. The polymerase extension reaction mixture consisted of 50 pmol of primer (5'-GTTGATG-TACACATTGTCAA-3', SEQ ID NO:1), 80 pmol of 100-mer template (5'-TACCCGGAGGCCAAGTACGGCGGG-TACGTCCTTGACAATGTGTACATCAA-CATCACCTACCACCATGTCAGTCTCGGT-TGGATCCTCTATTGTGTCCGGG-3', SEQ ID NO:2), 120 pmol of 3'-O-allyl-dNTP-allyl-Fluorophore, 1X Thermopol II reaction buffer [20 mM Tris-HCl/ 10 mM (NH$_4$)$_2$SO$_4$/10 mM KCl/2 mM MnCl$_2$/0.1% Triton X-100, pH 8.8, New England Biolabs], and 6 units of 9° N Polymerase (exo-) A485L/Y409V in a total volume of 20 µL.

General one-pot dual-deallylation procedure of DNA extension products. The DNA product from above (20 pmol) was added to a mixture of degassed 1× Thermopol I reaction buffer (20 mM Tris-HCl/10 mM (NH$_4$)$_2$SO$_4$/10 mM KCl/2 mM MgSO$_4$/0.1% Triton X-100, pH 8.8, 1 µL), Na$_2$PdCl$_4$ in degassed H$_2$O (7 µL, 23 nmol) and P(PhSO$_3$Na)$_3$ in degassed H$_2$O (10 µL, 176 nmol) to perform an one-pot dual-deallylation reaction. The reaction mixture was then placed in a heating block and incubated at 70° C. for 30 seconds to yield quantitatively deallylated DNA product and characterized by MALDI-TOF MS as a single peak.

5. Synthesis of 3'-O-allyl-dUTP-allyl-R6G (27)

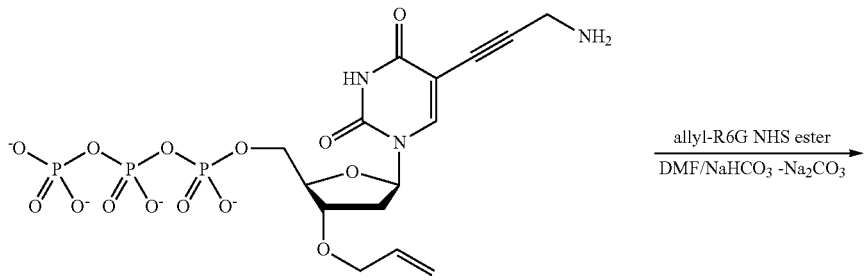

Figure 9:
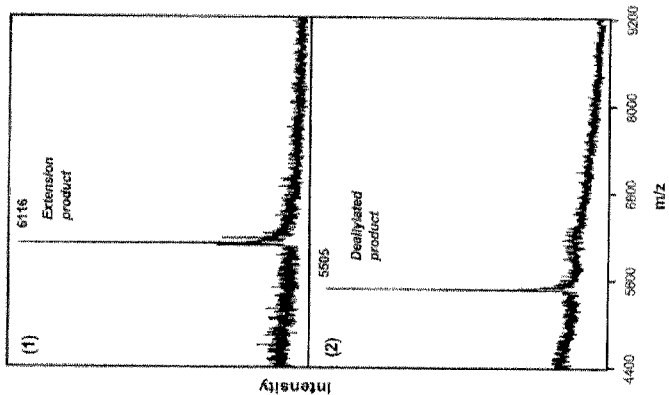
FIG. 9. Single base extension reaction and MALDI-TOF MS of 3'-O-Allyl-dUTP-allyl-R6G.
Figure 9:
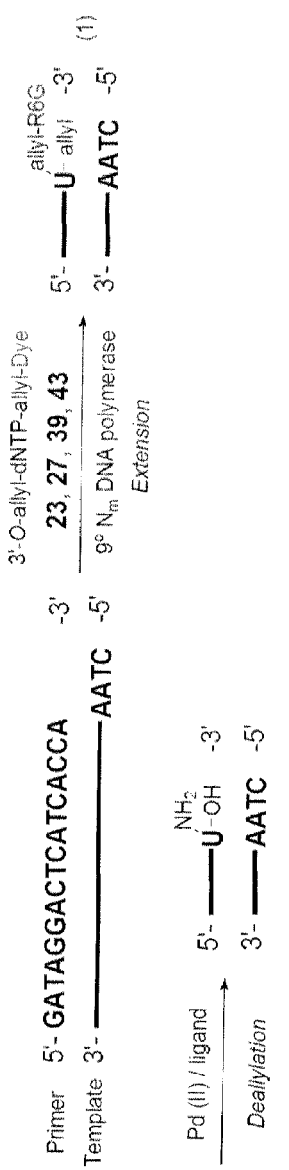
Figure 9:
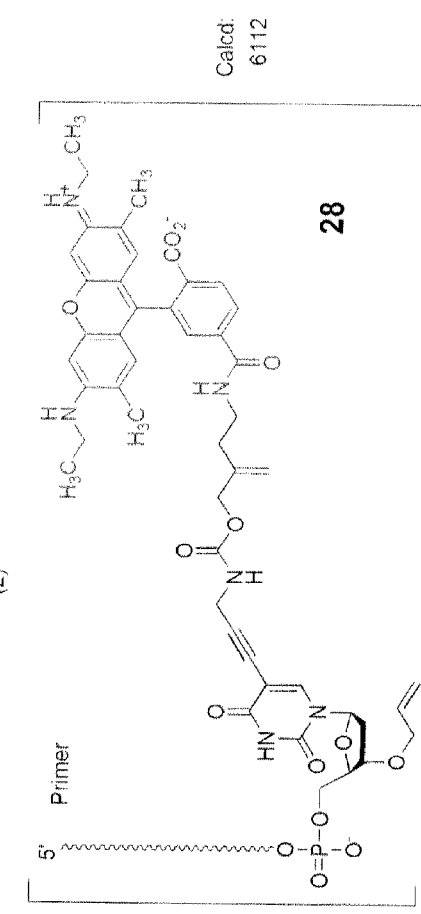
Figure 9:
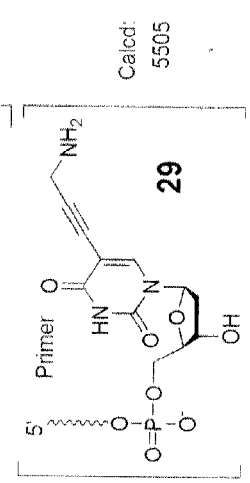

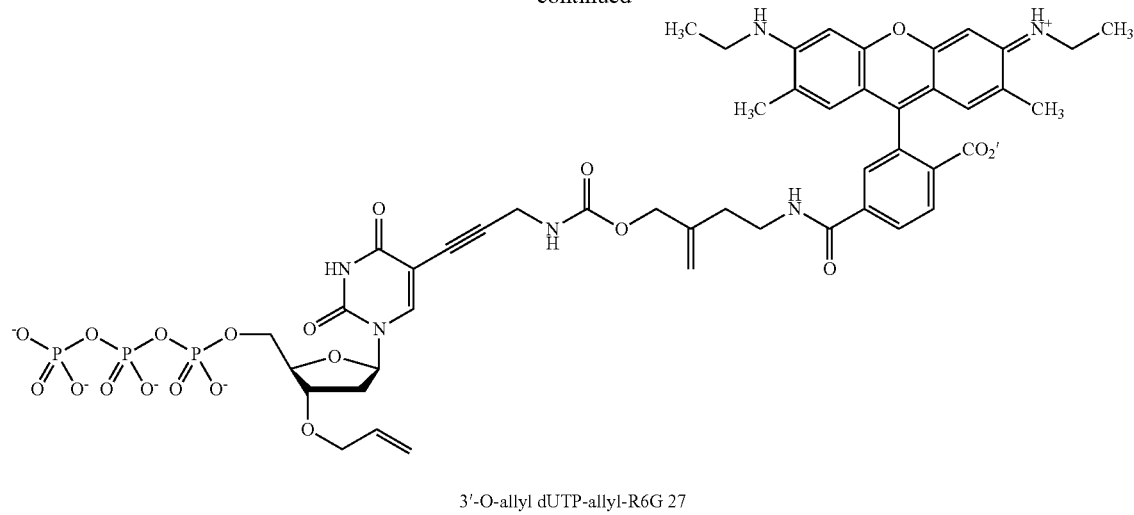
3'-O-allyl dUTP-allyl-R6G 27
Synthesis of 3'-O-allyl-dUTP-NH₂ 26 was performed according to the procedures in reference (28).
3'-O-Allyl-dUTP-allyl-R6G (27). The procedure was similar to the synthesis of 23. The product was characterized by the single base extension reaction and MALDI-TOF MS in FIG. 9.
6. Synthesis of 3'-O-allyl-dATP-allyl-ROX (39)
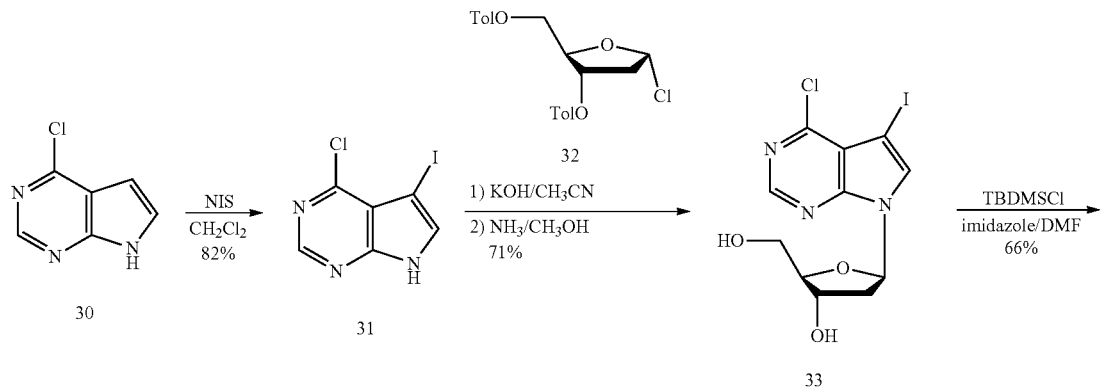
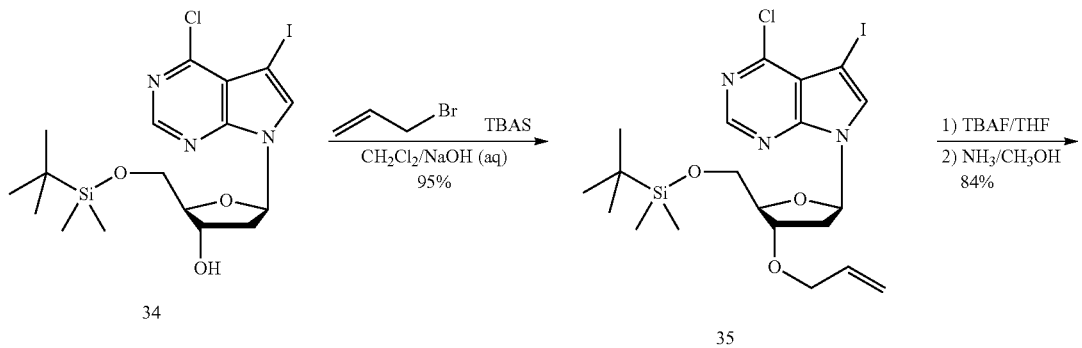

25

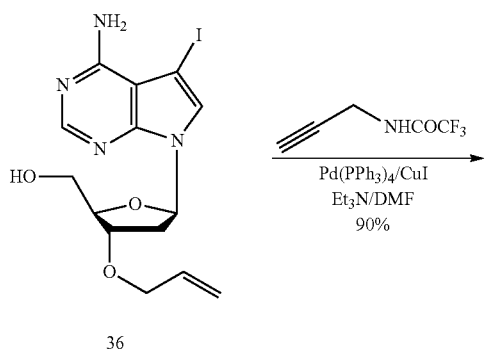

36

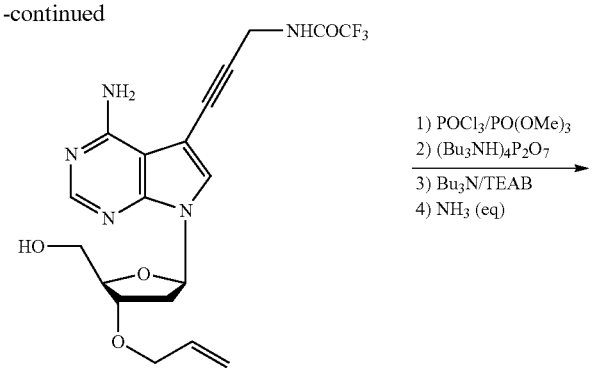

37

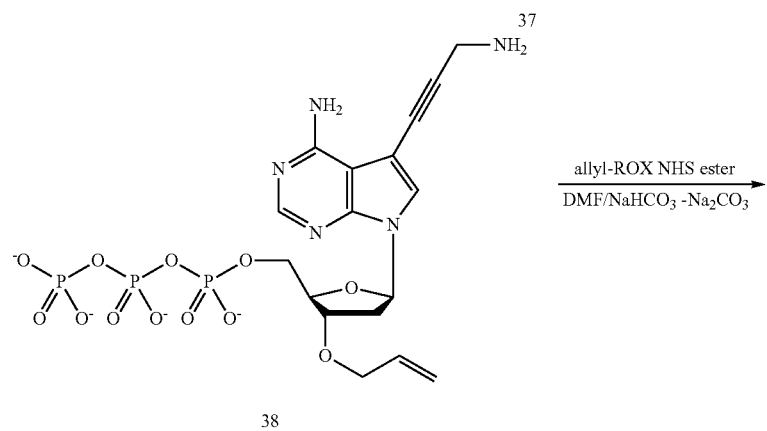

38

26

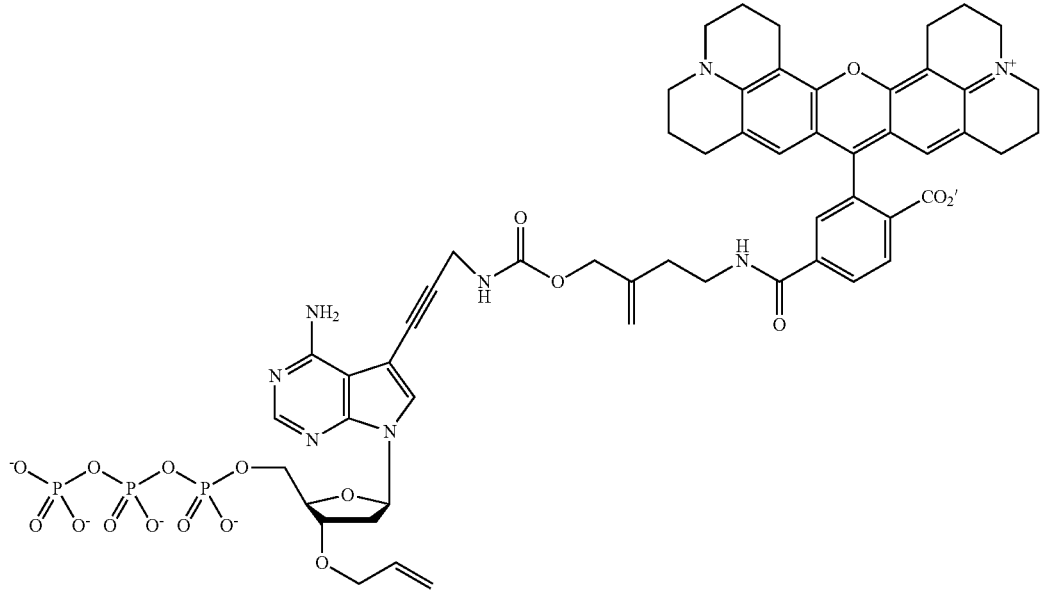

3'-O-allyl-dATP-allyl-ROX 39

6-Chloro-7-iodo-7-deazapurine (31). To a vigorously stirred solution of 30 (1.0 g; 6.51 mmol) in CH$_2$Cl$_2$ (55 mL), N-iodosuccimide (1.70 g; 7.18 mmol) was added. The suspension mixture was stirred at room temperature for 1 h, during which more precipitate was observed. The precipitate was filtered and then recrystallized in hot methanol to afford 31 (1.49 g; 82% yield): $^1$H NMR (400 MHz, DMSO-d$_6$) δ 12.96 (br s, 1H, NH), 8.59 (s, 1H, 2-H), 7.94 (s, 1H, 8-H); $^{13}$C NMR (100 MHz, DMSO-d$_6$) δ 151.2, 150.4, 150.2, 133.6, 115.5, 51.7; HRMS (FAB+) calcd for C$_5$H$_4$N$_3$C11 (M+H$^+$): 279.9139. found: 279.9141.

6-Chloro-9-(β-D-2'-deoxyribofuranosyl)-7-iodo-7-deazapurine (33). To a stirred solution of 31 (707 mg; 2.53 mmol) in CH$_3$CN (43 mL), KOH powder (355 mg; 6.34 mmol) and tris[2-(2-methoxyethoxy)ethyl]amine (TDA-1) (52 µL, 0.165 mmol) were added. The mixture was stirred at room temperature for 10 min and then 3,5-di-O-(p-toluoyl)-2-deoxy-D- ribofuranosyl chloride 32 (1.18 g; 2.73 mmol) was added. The reaction mixture was stirred vigorously at room temperature for 1 h, and the insoluble portion was filtered and washed with hot acetone. The combined solution was evaporated and dissolved in 7M ammonia in methanol solution (86 mL). The mixture was stirred at room temperature for 24 h. After evaporation, the crude product was purified by flash column chromatography using $CH_3OH$—$CH_3Cl_2$ (0-1:20) as the eluent to afford 33 as white solid (711 mg; 71% yield): $^1$H NMR (400 MHz, $CD_3OD$) δ 8.57 (s, 1H, 2-H), 8.08 (s, 1H, 8-H), 6.72 (dd, J=6.3, 7.5 Hz, 1H, 1'-H), 4.53 (m, 1H, 3'-H), 4.00 (m, 1H, 4'-H), 3.80 (dd, J=3.6, 12.0 Hz, 1H, one of 5'-H), 3.74 (dd, J=3.6, 12.0 Hz, 1H, one of 5'-H), 2.56-2.64 (ddd, J=6.1, 7.5, 13.5 Hz, 1H, one of 2'-H), 2.36-2.43 (ddd, J=3.3, 6.2, 13.5 Hz, 1H, one of 2'-H); $^{13}$C NMR (100 MHz, $CD_3OD$) δ 152.9, 151.7, 151.3, 134.7, 118.5, 89.0, 85.7, 72.6, 63.2, 52.6, 41.7; HRMS (FAB+) calcd for $C_{11}H_{12}O_3N_3ClI$ (M+H$^+$): 395.9612. found: 395.9607.

9-[β-D-5'-O-(tert-Butyldimethylsilyl)-2'-deoxyribofuranosyl]-6-chloro-7-iodo7-deazapurine (34). The procedure was similar to the synthesis of 18, and the crude product was purified by flash column chromatography using ethyl acetate-hexane (1:3-2) as the eluent to afford 34 as white solid (597 mg; 65% yield) and 33 (213 mg; 30% yield). The above procedure was repeated with the recovered 33 to achieve a 86% overall yield of 34: $^1$H NMR (400 MHz, $CD_3OD$) δ 8.56 (s, 1H, 2-H), 7.99 (s, 1H, 8-H), 6.73 ('t', J=6.7 Hz, 1H, 1'-H), 4.52 (m, 1H, 3'-H), 4.02 (m, 1H, 4'-H), 3.92 (dd, J=3.0, 11.4 Hz, 1H, one of 5'-H), 3.86 (dd, J=3.1, 11.4 Hz, 1H, one of 5'-H), 2.47-2.55 (ddd, J=5.8, 7.1, 13.4 Hz, 1H, one of 2'-H), 2.40-2.47 (ddd, J=3.6, 6.3, 13.4 Hz, 1H, one of 2'-H), 0.94 (s, 9H, C(CH$_3$)$_3$), 0.14 (s, 3H, one of SiCH$_3$), 0.13 (s, 3H, one of SiCH$_3$); $^{13}$C NMR (100 MHz, $CD_3OD$) δ 152.8, 151.5, 151.3, 133.8, 118.2, 88.9, 85.4, 72.5, 64.6, 52.6, 42.4, 26.7, 19.5, −4.9, −5.0; HRMS (FAB+) calcd for $C_{17}H_{26}O_3N_3ClSiI$ (M+H$^+$): 510.0477. found: 510.0487.

9-[β-D-3'-O-Allyl-5'-O-(tert-butyldimethylsilyl)-2'-deoxyribofuranosyl]-6-chloro-7-iodo-7-deazapurine (35). To a stirred solution of 34 (789 mg; 1.55 mmol) in $CH_2Cl_2$ (48 mL), tetrabutylammonium bromide (TBAB) (255 mg; 0.77 mmol), allyl bromide (0.69 mL, 7.74 mmol) and 40% aqueous NaOH solution (24 mL) were added respectively. The reaction mixture was stirred at room temperature for 1 h. Ethyl acetate (150 mL) was added and the organic layer was separated. The aqueous layer was extracted with ethyl acetate (2×50 mL). The combined organic layer was washed with saturated aqueous NaHCO$_3$, NaCl, and dried over anhydrous Na$_2$SO$_4$. After evaporation, the residue was purified by flash column chromatography using ethyl acetate-hexane (1:6) as the eluent to afford 35 as yellow oil (809 mg; 95% yield): $^1$H NMR (400 MHz, $CD_3OD$) δ 8.52 (s, 1H, 2-H), 7.94 (s, 1H, 8-H), 6.64 (dd, J=6.1, 7.6 Hz, 1H, 1'-H), 5.88-5.99 (m, 1H, CH$_2$CH=CH$_2$), 5.28-5.34 (dm, J=17.3 Hz, 1H, one of CH$_2$CH=CH$_2$), 5.16-5.21 (dm, J=10.4 Hz, 1H, one of CH$_2$CH=CH$_3$), 4.28 (m, 1H, 3'-H), 4.13 (m, 1H, 4'-H), 4.01-4.11 (m, 2H, CH$_3$CH=CH$_2$), 3.88 (dd, J=3.6, 11.2 Hz, 1H, one of 5'-H), 3.80 (dd, J=3.1, 11.3 Hz, 1H, one of 5'-H), 2.51-2.57 (ddd, J=2.7, 6.0, 13.5 Hz, 1H, one of 2'-H), 2.42-2.50 (ddd, J=5.7, 7.7, 13.5 Hz, 1H, one of 2'-H), 0.93 (s, 9H, C(CH$_3$)$_3$), 0.13 (s, 3H, one of SiCH$_3$), 0.12 (s, 3H, one of SiCH$_3$); $^{13}$C NMR (100 MHz, $CD_3OD$) δ 152.8, 151.4, 151.3, 135.5, 133.6, 118.2, 117.2, 86.5, 85.6, 80.2, 71.0, 64.8, 52.8, 39.7, 26.7, 19.4, −4.8, −5.0; HRMS (FAB+) calcd for $C_{30}H_{30}O_3N_3ClSiI$ (M+H$^+$): 550.0790. found: 550.0773.

3'-O-Allyl-7-deaza-7-iodo-2'-deoxyadenosine (36). To a stirred solution of 35 (809 mg; 1.47 mmol) in anhydrous THF (34 mL), 1 M TBAF in THF solution (1.62 mL; 1.62 mmol) was added and the reaction was stirred at room temperature for 1 h. After evaporation, the residue was dissolved in 7M ammonia in methanol solution (24 mL). The solution was stirred in an autoclave at 115-120° C. for 15 h. After evaporation, the residue was purified by flash column chromatography using $CH_3OH$—$CH_2Cl_2$ (1:20) as the eluent to afford 36 as white solid (514 mg; 84% yield): $^1$H NMR (400 MHz, $CD_3OD$) δ 8.08 (s, 1H, 2-H), 7.56 (s, 1H, 8-H), 6.45 (dd, J=5.8, 8.6 Hz, 1H, 1'-H), 5.90-6.00 (m, 1H, CH$_2$CH=CH$_2$), 5.29-5.35 (dm, J=17.2 Hz, 1H, one of CH$_2$CH=CH$_2$), 5.16-5.21 (dm, J=10.5 Hz, 1H, one of CH$_2$CH=CH$_2$), 4.28 (m, 1H, 3'-H), 4.12 (m, 1H, 4'-H), 4.02-4.12 (m, 2H, CH$_2$CH=CH$_2$), 3.78 (dd, J=3.7, 12.1 Hz, 1H, one of 5'-H), 3.70 (dd, J=3.6, 12.1 Hz, 1H, one of 5'-H), 2.53-2.61 (ddd, J=5.8, 8.6, 13.6 Hz, 1H, one of 2'-H), 2.41-2.47 (ddd, J=2.0, 5.8, 13.5 Hz, 1H, one of 2'-H); $^{13}$C NMR (100 MHz, $CD_3OD$) δ 158.5, 152.3, 150.3, 135.7, 128.8, 117.0, 105.3, 86.8, 86.4, 80.7, 71.0, 63.7, 51.3, 38.8; HRMS (FAB+) calcd for $C_{14}H_{18}O_3N_4I$ (M+H$^+$): 417.0424. found: 417.0438.

3'-O-Allyl-7-deaza-7-{3-[(trifluoroacetyl)amino]prop-1-ynyl}-2'-deoxyadenosine (37). The procedure was similar to the synthesis of 21, and the crude product was purified by flash column chromatography using ethyl acetate-hexane (1:1-0) as the eluent to afford 37 as yellow solid (486 mg; 90% yield): $^1$H NMR (400 MHz, $CD_3OD$) δ 8.08 (s, 1H, 2-H), 7.60 (s, 1H, 8-H), 6.41 (dd, J=5.8, 8.6 Hz, 1H, 1'-H), 5.89-6.00 (m, 1H, CH$_2$CH=CH$_2$), 5.29-5.35 (dm, J=17.3 Hz, 1H, one of CH$_2$CH=CH$_2$), 5.16-5.21 (dm, J=10.4 Hz, 1H, one of CH$_2$CH_CH$_2$), 4.31 (s, 2H, C=CCH$_2$), 4.29 (m, 1H, 3'-H), 4.13 (m, 1H, 4'-H), 4.01-4.11 (m, 2H, CH$_2$CH=CH$_2$), 3.79 (dd, J=3.6, 12.1 Hz, 1H, one of 5'-H), 3.71 (dd, J=3.5, 12.1 Hz, 1H, one of 5'-H), 2.54-2.62 (ddd, J=5.8, 8.6, 13.6 Hz, 1H, one of 2'-H), 2.42-2.48 (ddd, J=1.9, 5.8, 13.6 Hz, 1H, one of 2'-H); $^{13}$C NMR (100 MHz, $CD_3OD$) δ 158.8, 158.6 (q, J=38 Hz, COCF$_3$), 152.9, 149.6, 135.6, 128.1, 117.1 (q, J=284 Hz, COCF$_3$), 117.0, 104.5, 96.3, 87.3, 86.9, 86.8, 80.7, 77.0, 71.0, 63.8, 38.7, 31.1; HRMS (FAB+) calcd for $C_{19}H_{21}O_4N_5F_3$ (M+H$^+$): 440.1546. found: 440.1544.

3'-O-Allyl-7-(3-aminoprop-1-ynyl)-7-deaza-2'-deoxyadenosine-5'-triphosphate (38). The procedure was similar to the synthesis of 22 to yield 3B as colorless syrup: $^1$H NMR (300 MHz, $D_2O$) δ 8.02 (s, 1H, 2-H), 7.89 (s, 1H, 8-H), 6.54 (t, J=6.6 Hz, 1H, 1'-H), 5.89-6.02 (m, 1H, CH$_2$CH=CH$_2$), 5.30-5.39 (dm, J=17.3 Hz, 1H, one of CH$_2$CH=CH$_2$), 5.20-5.27 (dm, J=10.4 Hz, 1H, one of CH$_2$CH=CH$_2$), 4.48 (s, 2H, C=CCH$_2$), 4.35 (m, 1H, 3'-H), 4.05-4.17 (m, 4H, CH$_2$CH=CH$_2$ and 5'-H), 3.99 (m, 1H, 4'-H), 2.50-2.59 (m, 2H, 2'-H); $^{31}$P NMR (121.4 MHz, $D_2O$) δ −6.1 (d, J=21.1 Hz, 1P, γ-P), −10.8 (d, J=18.8 Hz, 1P, α-P), −21.9 (t, J=19.9 Hz, 1P, β-P).

Figure 10:
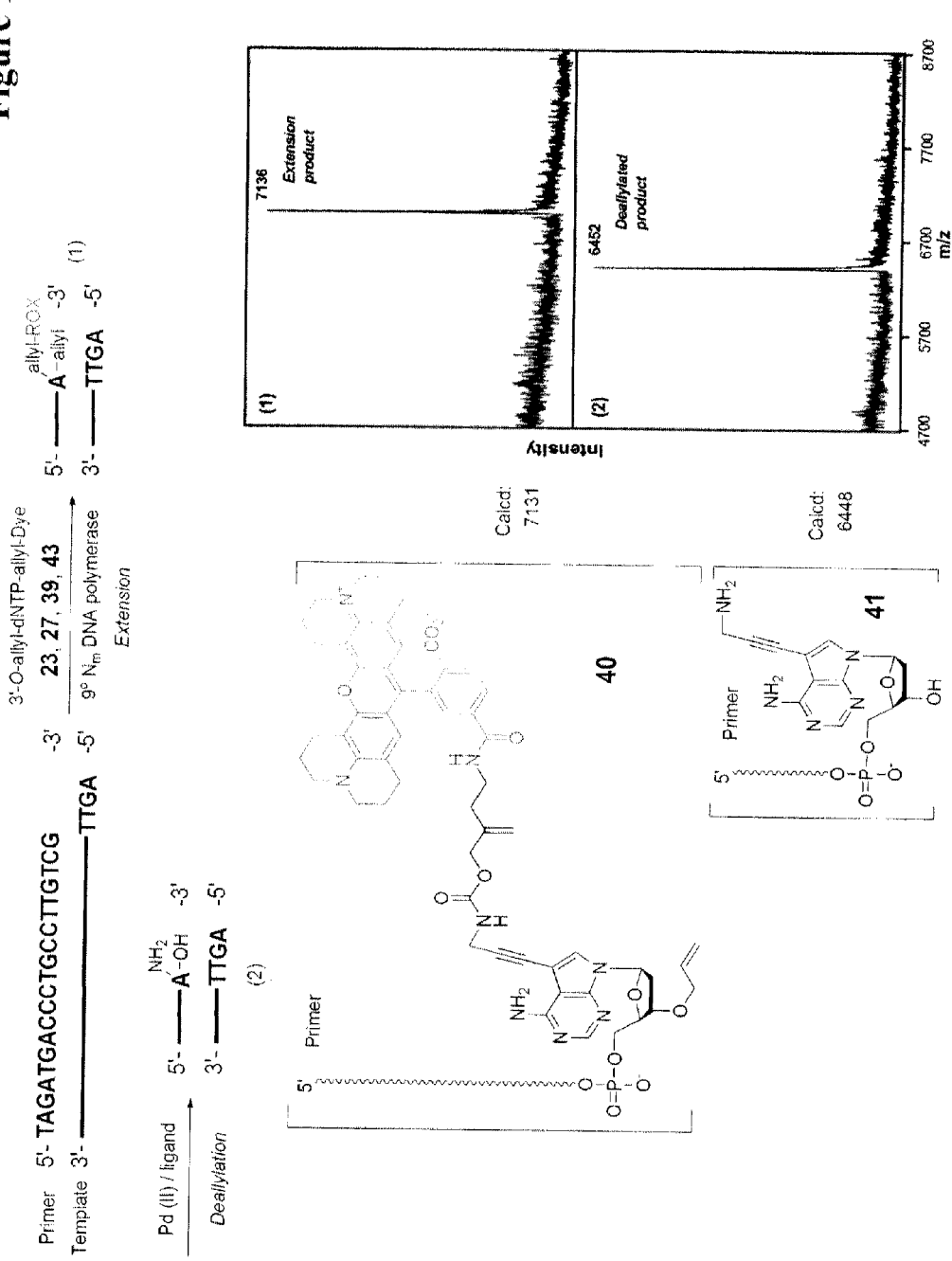
FIG. 10. Single base extension reaction and MALDI-TOF MS of 3'-O-Allyl-dATP-allyl-ROX (39).

3'-O-Allyl-dATP-allyl-ROX (39). The procedure was similar to the synthesis of 23. The product was characterized by single base extension reaction and MALDI-TOF MS. See FIG. 10.

7. Synthesis of 3'-O-allyl-dGTP-allyl-Bodipy-650 (43) and 3'-O-allyl-dGTP-allyl-Cy5 (44)
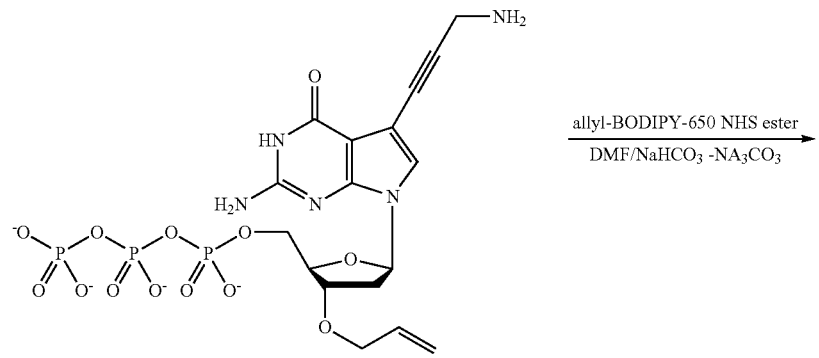
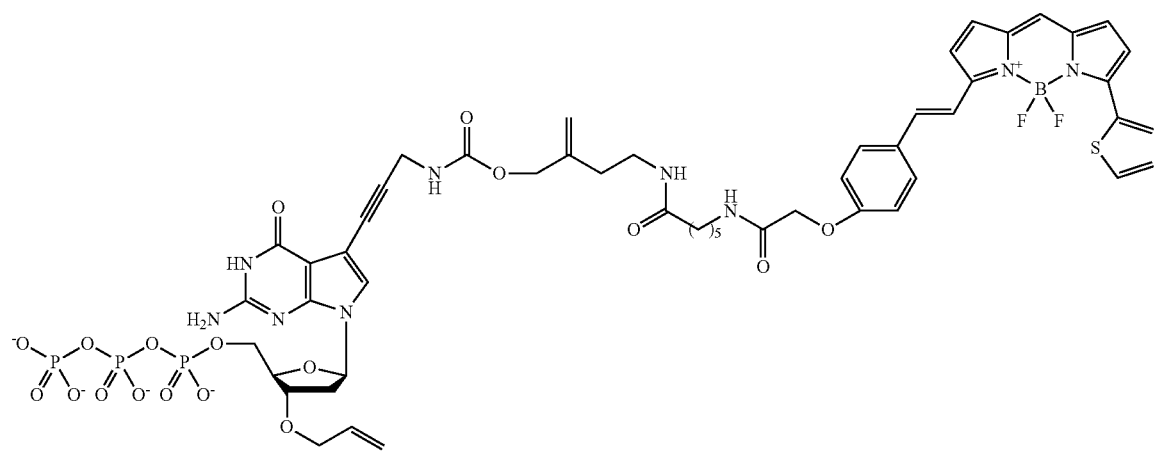
3'-O-allyl-dGTP-allyl-Bodipy-650 43
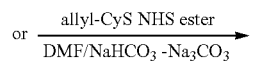
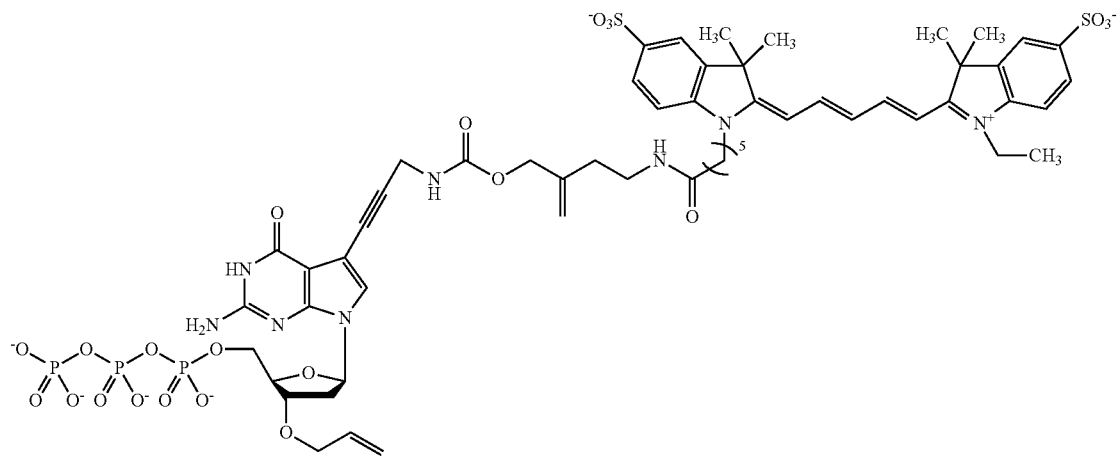
3'-O-allyl-dGTP-allyl-Cy5 44

Synthesis of 3'-O-allyl-dGTP-NH$_2$ 42 was performed according to the procedures in reference (29).

Figure 11:
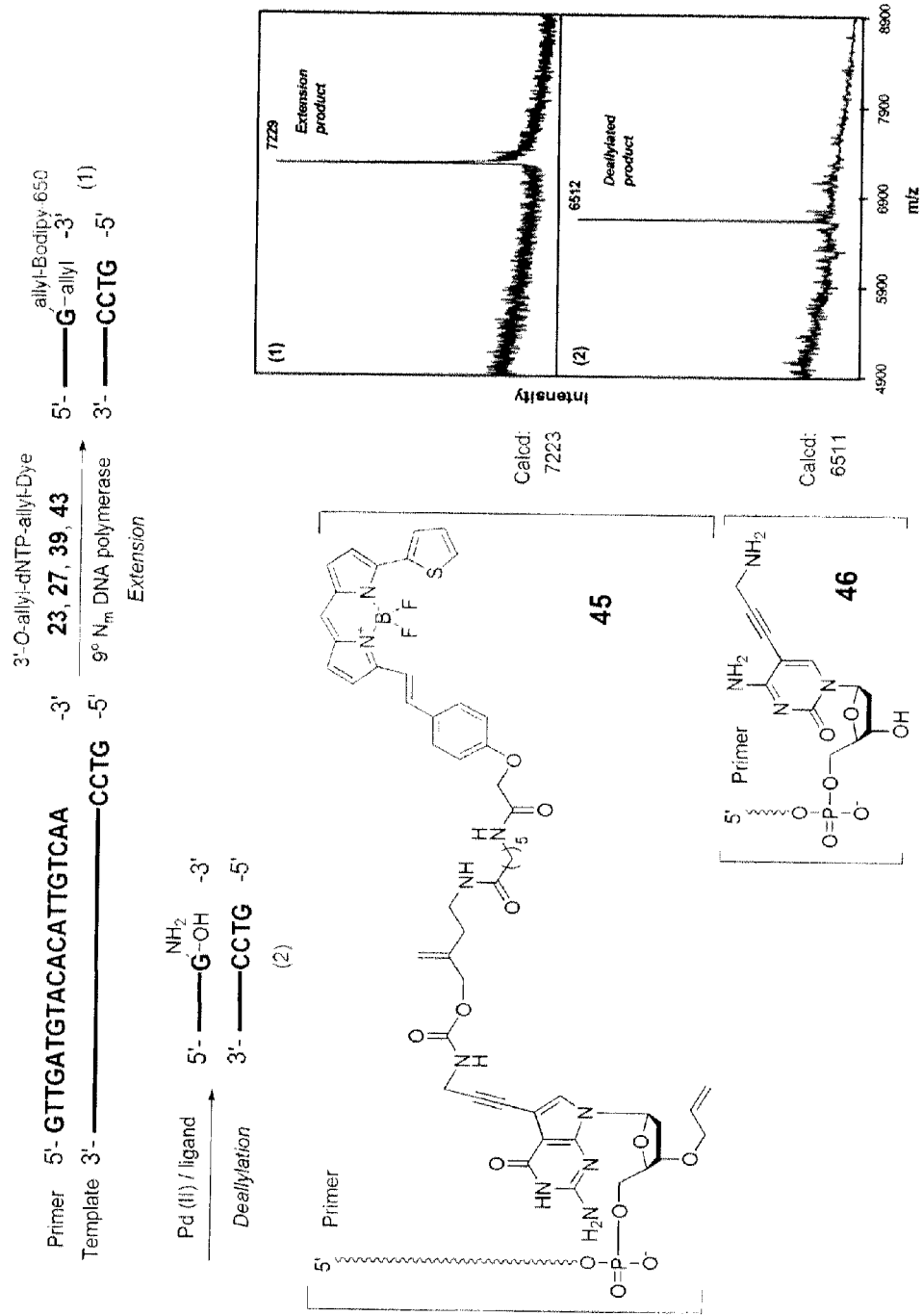
FIG. 11. Single base extension reaction and MALDI-TOF MS of 3'-O-Allyl-dGTP-allyl-Bodipy-650 (43) and 3'-O-allyl-dGTP-allyl-Cy5 (44).
Figure 12:
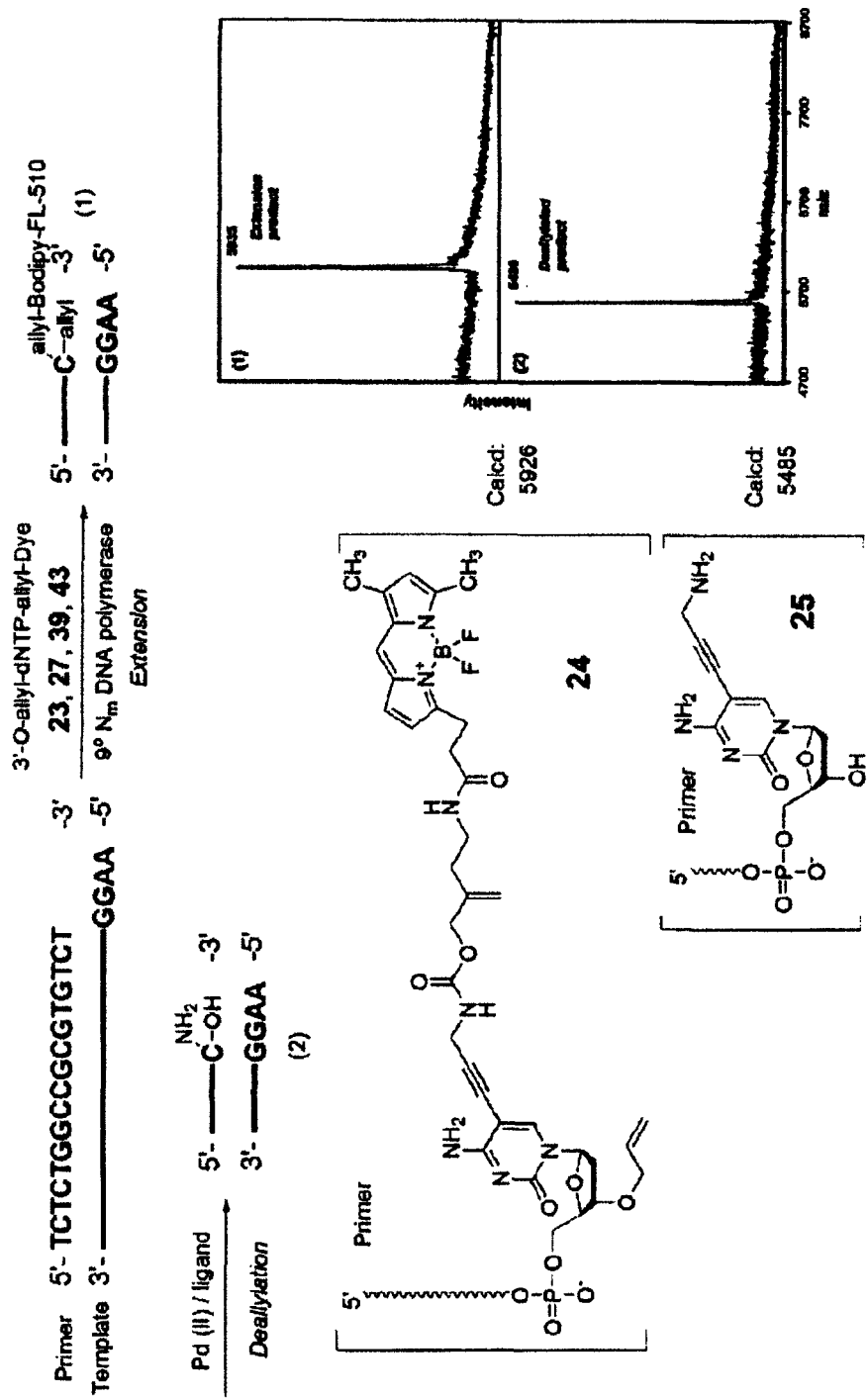
FIG. 12. Single base extension reaction and MALDI-TOF MS of 3'-O-Allyl-dCTP-allyl-Bodipy-FL-510 (23).

3'-O-Allyl-dGTP-allyl-Bodipy-650 (43) and 3'-O-allyl-dGTP-allyl-Cy5 (44). The procedures were similar to the synthesis of 23. The product was characterized by single base extension reaction and MALDI-TOF MS. See FIG. 11.

II. Synthesis of 3'-O-allyl-dNTPs

1. Synthesis of 3'-O-allyl dCTP (51)

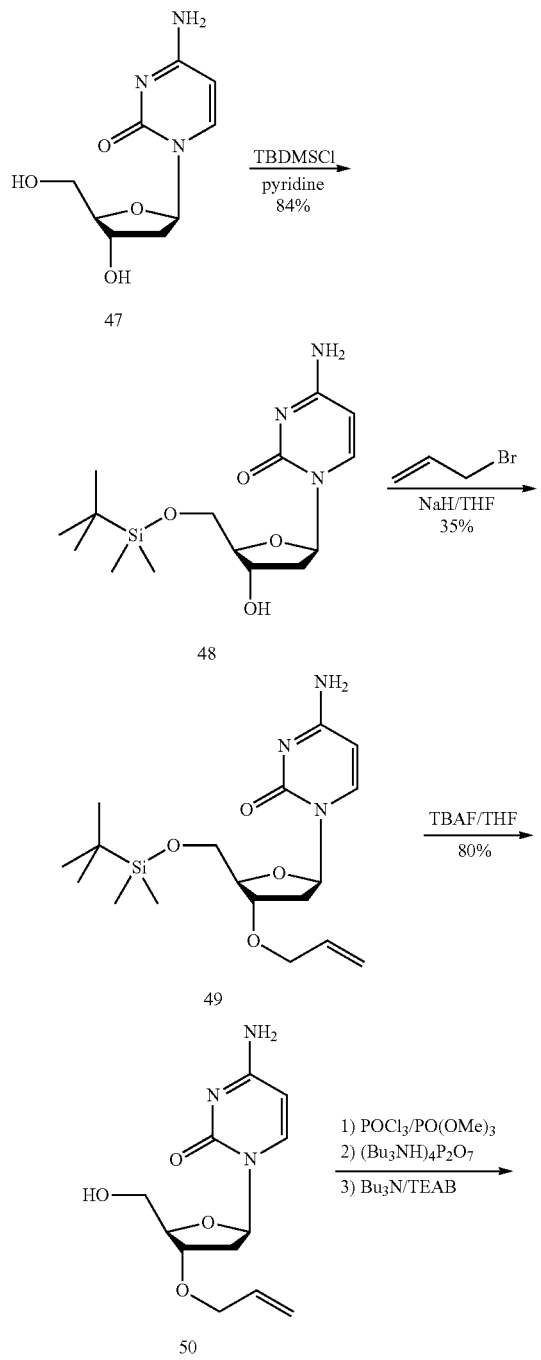

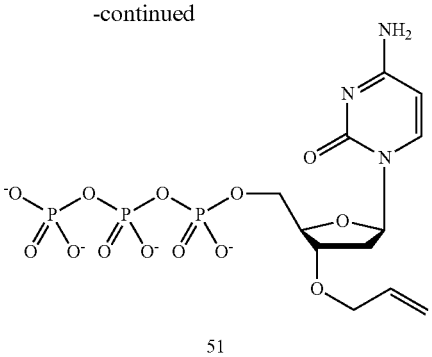

5'-O-(tert-Butyldimethylsilyl)-2'-deoxycytidine (48). To a stirred solution of 2'-deoxycytidine 47 (1.00 g; 4.40 mmol) in dry pyridine (37 mL), TBDMSCl (814 mg; 5.39 mmol) was added. The mixture was stirred at room temperature for 20 h. After evaporation, the residue was purified by flash column chromatography using CH$_3$OH—CH$_2$Cl$_2$ (1:10) as the eluent to afford 48 as white solid (1.26 g; 84% yield): $^1$H NMR (400 MHz, CH$_3$OD) δ 8.03 (d, J=7.5 Hz, 1H, 6-H), 6.23 (t, J=6.3 Hz, 1H, 1'-H), 5.86 (d, J=7.5 Hz, 1H, 5-H), 4.35 (m, 1H, 3'-H), 3.91-3.98 (m, 2H, 4'-H and one of 5'-H), 3.85 (dd. J=2.5, 11.3 Hz, 1H, one of 5'-H), 2.36-2.43 (ddd, J=4.1, 6.1, 13.5 Hz, 1H, one of 2'-H), 2.05-2.13 (m, 1H, one of 2'-H), 0.94 (s, 9H, C(CH$_3$)$_3$), 0.14 (s, 3H, one of SiCH$_3$), 0.13 (s, 3H, one of SiCH$_3$); $^{13}$C NMR (100 MHz, CD$_3$OD) δ 167.1, 157.6, 142.1, 95.6, 88.7, 87.4, 71.7, 64.1, 42.7, 26.5, 19.3, −5.2, −5.3; HRMS (FAB+) calcd for C$_{15}$H$_{28}$O$_4$N$_3$Si (M+H$^+$): 342.1849. found: 342.1844.

3'-O-Allyl-5'-O-(tert-butyldimethylsilyl)-2'-deoxycytidine (49). The procedure was similar to the synthesis of 19 and the crude product was purified by flash column chromatography using CH$_3$OH—CH$_2$Cl$_2$ (1:20) as the eluent to afford 49 as yellow solid (480 mg; 35% yield): $^1$H NMR (400 MHz, CD$_3$OD) δ 7.97 (d, J=7.5 Hz, 1H, 6-H), 6.21 (t, J=6.5 Hz, 1H, 1'-H), 5.87 (d, J=7.5 Hz, 1H, 5-H), 5.87-5.97 (m, 1H, CH$_2$CH=CH$_2$), 5.26-5.33 (dm, J=17.2 Hz, 1H, one of CH$_2$CH=CH$_2$), 5.15-5.20 (dm, J=10.5 Hz, 1H, one of CH$_2$CH=CH$_2$), 4.16 (m, 1H, 3'-H), 4.11 (m, 1H, 4'-H), 3.97-4.11 (m, 2H, CH$_2$CH=CH$_2$), 3.92 (dd, J=3.2, 11.4 Hz, 1H, one of 5'-H), 3.84 (dd, J=2.8, 11.4 Hz, 1H, one of 5'-H), 2.46-2.51 (ddd, J=3.1, 5.9, 13.6 Hz, 1H, one of 2'-H), 2.00-2.08 (m, 1H, one of 2'-H), 0.94 (s, 9H, C(CH$_3$)$_3$), 0.13 (s, 6H, Si(CH$_3$)$_2$); $^{13}$C NMR (100 MHz, CD$_3$OD) δ 167.2, 157.7, 141.9, 135.6, 117.1, 95.7, 87.5, 86.6, 79.7, 71.1, 64.4, 39.8, 26.5, 19.3, −5.1, −5.2; HRMS (FAB+) calcd for C$_{15}$H$_{28}$O$_4$N$_3$Si (M+H$^+$): 342.1849. found: 342.1844.

3'-O-Allyl-2'-deoxycytidine (50). The procedure was similar to the synthesis of 20 and the crude product was purified by flash column chromatography using CH$_3$OH-THF (1:12) and CH$_3$OH-ethyl acetate (1:4) as the eluent to afford 50 as white foam (269 mg; 80% yield):

$^1$H NMR (400 MHz, CD$_3$OD) δ 7.96 (d, J=7.5 Hz, 1H, 6-H), 6.21 (dd, J=5.9, 7.6 Hz, 1H, 1'-H), 5.89 (d, J=7.5 Hz, 1H, 5-H), 5.87-5.98 (m, 1H, CH$_2$CH=CH$_2$), 5.27-5.33 (dm, J=17.3 Hz, 1H, one of CH$_2$CH=CH$_2$), 5.15-5.19 (dm, J=10.4 Hz, 1H, one of CH$_2$CH=CH$_2$), 4.17 (m, 1H, 3'-H), 3.98-4.10 (m, 3H, 4'-H and CH$_2$CH=CH$_T$), 3.77 (dd, J=3.6, 12.0 Hz, 1H, one of 5'-H), 3.71 (dd, J=3.7, 12.0 Hz, 1H, one of 5'-H), 2.43-2.50 (ddd, J=2.7, 5.9, 13.6 Hz, 1H, one of 2'-H), 2.03-2.11 (ddd, J=6.2, 7.7, 13.6 Hz, 1H, one of 2'-H); $^{13}$C NMR (100 MHz, CD$_3$OD) δ 167.1, 157.7, 142.2, 135.5, 117.0, 96.0, 87.5, 86.6, 80.0, 71.0, 63.0, 39.1; HRMS (FAB+) calcd for $C_{12}H_{18}O_4N_2$ (M+H$^+$): 268.1297. found: 268.1307.

3'-O-Allyl-2'-deoxycytidine-5'-triphosphate (51). 50 (86 mg; 0.32 mmol) and proton sponge (84 mg; 0.39 mmol) were dried in a vacuum desiccator over $P_2O_5$ overnight before dissolving in trimethylphosphate (0.60 mL). Freshly distilled $POCl_3$ (35.8 µL; 0.383 mmol) was added dropwise at 0° C. and the mixture was stirred for 3 h. Then the solution of tributylammonium pyrophosphate (607 mg) and tributylamine (0.61 mL; 2.56 mmol) in anhydrous DMF (2.6 mL) was well vortexed and added in one portion at room temperature and the reaction was stirred for 30 min. After that triethylammonium bicarbonate solution (TEAB) (0.1 M; 16 mL) was added and the mixture was stirred for 2 h. After most liquid was removed under vacuum, the residue was redissolved in water (2 mL) and filtered. The aqueous solution was purified by DEAE Sephadex A25 ion exchange column using gradient aqueous TEAS solution (from 0.1 M to 1.0 M) as eluent to afford 51 as colorless syrup after evaporation: $^1$H NMR (300 MHz, $D_2O$) δ 7.90 (d, J=7.4 Hz, 1H, 6-H), 6.20 (dd, J=5.9, 7.6 Hz, 1H, 1'-H), 5.92 (d, J=7.4 Hz, 1H, 5-H), 5.85-5.97 (m, 1H, $CH_2CH=CH_2$), 5.25-5.34 (m, 1E, one of $CH_2CH=CH_2$), 5.15-5.20 (m, 1H, one of $CH_2CH=CH_2$), 4.15 (m, 1H, 3'-H), 3.96-4.10 (m, 3H, 4'-H and $CH_2CH=CH_2$), 3.70-3.80 (m, 2H, 5'-H), 2.43-2.52 (m, 1H, one of 2'-H), 2.05-2.14 (m, 1H, one of 2'-H); $^{31}$P NMR (121.4 MHz, $D_2O$) δ −8.8 (d, J=19.0 Hz, 1P, γ-P), −11.3 (d, J=19.6 Hz, 1P, α-P), −22.9 (t, J=19.5 Hz, 1P, β-P).

2. Synthesis of 3'-O-allyl-dTTP (53)

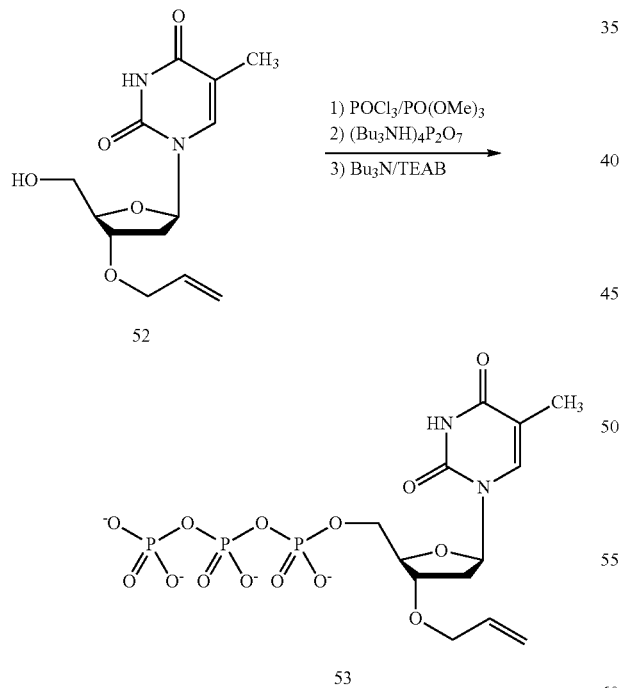

52

53

Synthesis of 3'-O-allylthymidine 52 was performed according to the procedures in reference (28).

3'-O-Allylthymidine-5'-triphosphate (53). The procedure was similar to the synthesis of 51 to yield 53 as colorless syrup: $^1$H NMR (300 MHz, $D_2O$) δ 7.80 (m, 1H, 6-H), 6.23 (dd, J=6.2, 8.1 Hz, 1H, 1'-H), 5.85-5.97 (m, 1H, $CH_2CH\_CH_2$), 5.25-5.32 (m, 1H, one of $CH_2CH=CH_2$), 5.15-5.21 (m, 1H, one of $CH_2CH=CH_2$), 4.17 (m, 1H, 3'-H), 3.97-4.11 (m, 3H, 4'-H and $CH_2CH=CH_2$), 3.70-3.80 (m, 2H, 5'-H), 2.30-2.41 (m, 1H, one of 2'-H), 2.11-2.23 (m, 1H, one of 2'-H), 1.86 (d, J=1.2 Hz, 3H, $CH_3$); $^{31}$P NMR (121.4 MHz, $D_2O$) δ −7.1 (d, J=20.1 Hz, 1P, γ-P), −10.8 (d, J=19.5 Hz, 1P, α-P), −21.8 (t, J=19.5 Hz, 1P, β-P).

3. Synthesis of 3'-O-allyl-dATP (59)

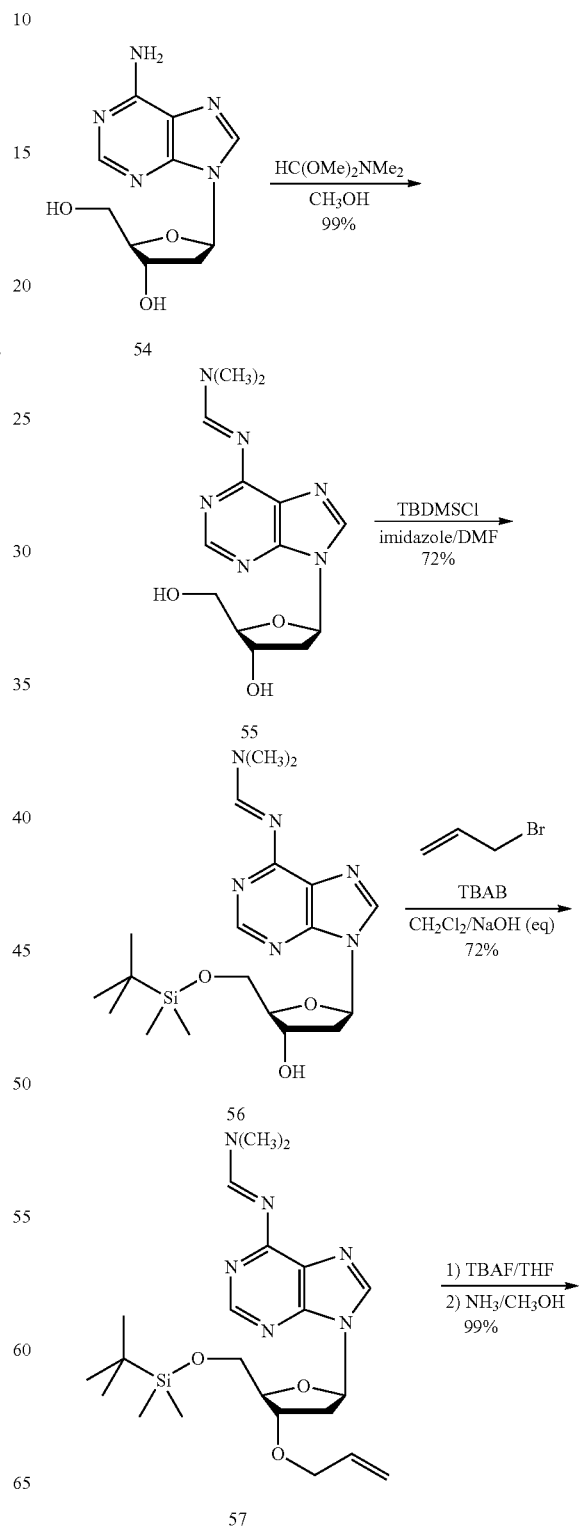

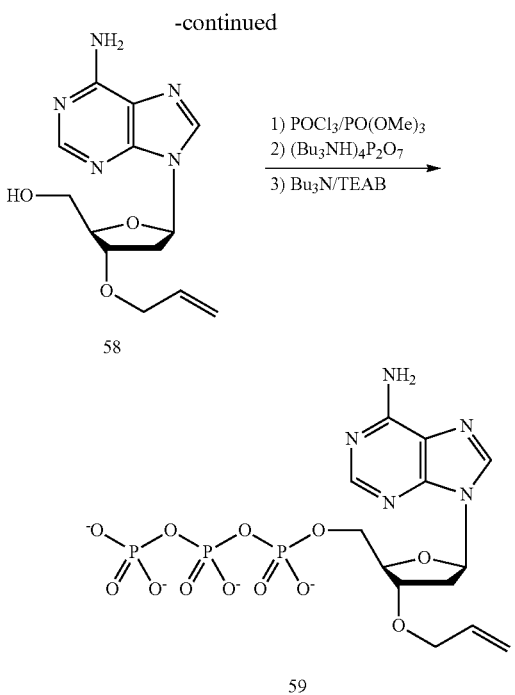

N6-((Dimethylamino)methylene)-2'-deoxyadenosine (55). To a stirred solution of 2'-deoxyadenosine monohydrate 54 (1.00 g; 3.71 mmol) in methanol (43 mL), N,N-dimethylformamide dimethyl acetal (2.48 mL; 18.6 mmol) was added. The reaction was stirred at 50° C. for 16 h. After evaporation, $CH_2Cl_2$-hexane (1:1) was added. The white solid formed was then filtered, collected and washed by hexane to afford 55 as white solid (1.13 g; 99% yield): $^1$H NMR (400 MHz, $CD_3OD$) δ 8.92 (s, 1H, $CHN(CH_3)_2$), 8.44 (s, 1H, 2-H), 8.43 (s, 1H, 8-H), 6.48 (dd, J=6.2, 7.8 Hz, 1H, 1'-H), 4.59 (m, 1H, 3'-H), 4.07 (m, 1H, 4'-H), 3.86 (dd, J=3.1, 12.2 Hz, 1H, one of 5'-H), 3.76 (dd, J=3.5, 12.2 Hz, 1H, one of 5'-H), 3.25 (s, 3H, one of $NCH_3$), 3.24 (s, 3H, one of $NCH_3$), 2.80-2.88 (ddd, J=5.9, 7.8, 13.5 Hz, 1H, one of 2'-H), 2.40-2.47 (ddd, J=2.8, 6.1, 13.4 Hz, 1H, one of 2'-H); $^{13}$C NMR (100 MHz, $CD_3OD$) δ 161.0, 159.9, 152.8, 151.1, 142.8, 127.0, 89.7, 86.9, 72.9, 63.5, 41.5 (N(CHO 2) 35.3; HRMS (FAB+) calcd for $C_{33}H_{19}O_3N_6$ (M+H$^+$): 307.1519. found: 307.1511.

5'-O-(tert-Butyldimethylsilyl)-N6-[(dimethylamino)methylene]-2'-deoxyadenosine (56). The procedure was similar to the synthesis of 18, and the crude product was purified by flash column chromatography using $CH_3OH$—$CH_2Cl_2$ (1:20) as the eluent to afford 56 as white foam (1.11 g; 72% yield): $^1$H NMR (400 MHz, $CD_3OD$) δ 8.90 (s, 1H, $CHN(CH_3)_2$), 8.45 (s, 1H, 2-H), 8.43 (s, 1H, 8-H), 6.49 (t, J=6.5 Hz, 1H, 1'-H), 4.59 (m, 1H, 3'-H), 4.04 (m, 1H, 4'-H), 3.95 (dd, J=3.7, 11.3 Hz, 1H, one of 5'-H), 3.85 (dd, J=2.8, 11.3 Hz, 1H, one of 5'-H), 3.25 (s, 3H, one of $NCH_3$), 3.24 (s, 3H, one of $NCH_3$), 2.73-2.81 (m, 1H, one of 2'-H), 2.48-2.55 (ddd, J=4.0, 6.4, 13.5 Hz, 1H, one of 2'-H), 0.90 (s, 9H, $C(CH_3)_3$), 0.08 (s, 3H, one of $SiCH_3$), 0.07 (s, 3H, one of $SiCH_3$); $^{13}$C NMR (100 MHz, $CD_3OD$) δ 160.6, 159.7, 153.0, 151.7, 141.8, 126.5, 88.9, 85.7, 72.1, 64.3, 41.6, 41.5, 35.3, 26.5, 19.3, −5.0, −5.1; HRMS (FAB+) calcd for $C_{19}H_{33}O_3N_6Si$ (M+H$^+$): 421.2383. found: 421.2390.

3'-O-Allyl-5'-O-(t-butyldimethylsilyl)-N6-[(dimethylamino)methylene]-2'-deoxyadenosine (57). The procedure was similar to the synthesis of 35, and the crude product was purified by flash column chromatography using $CH_3OH$—$CH_2Cl3$ (1:25) and $CH_3OH$-ethyl acetate (1:10) as the eluent to afford 57 as colorless oil (875 mg; 72% yield): $^1$H NMR (400 MHz, $CD_3OD$) δ 8.90 (s, 1H, $CHN(CH_3)_2$), 8.44 (s, 1H, 2-H), 8.41 (s, 1H, 8-H), 6.45 (dd, J=6.3, 7.2 Hz, 1H, 1'-H), 5.91-6.01 (to, 1H, $CH_2CH=CH_2$), 5.30-5.37 (dm, J=17.2 Hz, 1H, one of $CH_2CH=CH_2$), 5.18-5.22 (dm, J=10.5 Hz, 1H, one of $CH_2CH=CH_2$), 4.37 (m, 1H, 3'-H), 4.17 (m, 1H, 4'-H), 4.05-4.15 (m, 2H, $CH_2CH=CH_2$), 3.91 (dd, J=4.6, 11.1 Hz, 1H, one of 5'-H), 3.83 (dd, J=3.8, 11.1 Hz, 1H, one of 5'-H), 3.25 (s, 3H, one of $NCH_3$), 3.24 (s, 3H, one of $NCH_3$), 2.76-2.83 (ddd, J=6.0, 7.3, 13.6 Hz, 1H, one of 2'-H), 2.59-2.65 (ddd, J=3.0, 6.1, 13.6 Hz, 1H, one of 2'-H), 0.90 (s, 9H, $C(CH_3)_3$), 0.08 (s, 6H, $Si(CH_3)_2$); $^{13}$C NMR (100 MHz, $CD_3OD$) δ 160.7, 159.7, 153.1, 151.8, 141.9, 135.6, 126.5, 117.1, 86.7, 85.9, 80.1, 71.1, 64.5, 41.5, 38.7, 35.3, 26.5, 19.3, −5.0, −5.1; HRMS (FAB+) calcd for $C_{33}H_{37}O_3N_6Si$ (M+H$^+$): 461.2696. found: 461.2695.

3'-O-Allyl-2'-deoxyadenosine (58). To a stirred solution of 57 (875 mg; 1.90 mmol) in anhydrous THF (45 mL), 1 M TBAF in THF solution (2.09 mL; 2.09 mmol) was added and the reaction was stirred at room temperature for 1 h. After evaporation, the residue was dissolved in 7 M ammonia in methanol solution (34 mL). The mixture was then stirred in a sealed flask at 50° C. for 9 h. After evaporation, the residue was purified by flash column chromatography using $CH_3OH$—$CH_2Cl_2$ (1:10) as the eluent to afford 58 as white solid (548 mg; 99% yield): $^1$H NMR (400 MHz, $CD_3OD$) δ 8.30 (s, 1H, 2-H), 8.17 (s, 1H, 8-H), 6.38 (dd, J=5.8, 8.6 Hz, 1H, 1'-H), 5.91-6.01 (m, 1H, $CH_2CH=CH_2$), 5.30-5.37 (dm, J=17.3 Hz, 1H, one of $CH_2CH=CH_2$), 5.17-5.22 (dm, J=10.6 Hz, 1H, one of $CH_2CH=CH_2$), 4.36 (m, 1H, 3'-H), 4.21 (m, 1H, 4'-H), 4.04-4.15 (m, 2H, $CH_2CH=CH_2$), 3.85 (dd, J=3.2, 12.3 Hz, 1H, one of 5'-H), 3.74 (dd, J=3.2, 12.3 Hz, 1H, one of 5'-H), 2.75-2.83 (ddd, J=5.7, 8.6, 13.6 Hz, 1H, one of 2'-H), 2.52-2.58 (ddd, J=1.8, 5.8, 13.6 Hz, 1H, one of 2'-H); $^{13}$C NMR (100 MHz, $CD_3OD$) δ 157.1, 153.1, 149.5, 141.2, 135.6, 120.6, 117.0, 87.5, 87.2, 80.9, 71.0, 63.9, 38.7; HRMS (FAB+) calcd for $C_{13}H_{18}O_3N_5$ (M+H$^+$): 292.1410. found: 292.1426.

3'-O-Allyl-2'-deoxyadenosine-5'-triphosphate (59). The procedure was similar to the synthesis of 51 to yield 59 as colorless syrup: $^1$H NMR (300 MHz, $D_2O$) δ 8.46 (s, 1H, 2-H), 8.19 (s, 1H, 8-H), 6.43 (dd, J=6.3, 7.2 Hz, 1H, 1'-H), 5.90-6.02 (m, 1H, $CH_2CH=CH_2$), 5.31-5.40 (dm, J=17.1 Hz, 1H, one of $CH_2CH=CH_2$), 5.21-5.28 (dm, J=10.8 Hz, 1H, one of $CH_2CH=CH_2$), 4.55 (m, 1H, 3'-H), 4.40 (m, 1H, 4'-H), 4.06-4.20 (m, 4H, $CH_2CH=CH_2$ and 5'-H), 2.61-2.82 (m, 2H, 2'-H); $^1$H NMR (121.4 MHz, $D_2O$) −8.9 (d, J=19.1 Hz, 1P, γ-P), −11.2 (d, J=19.7 Hz, 1P, α-P), −22.8 (t, J=19.9 Hz, 1P, β-P).

4. Synthesis of 3'-O-allyl-dGTP (65)

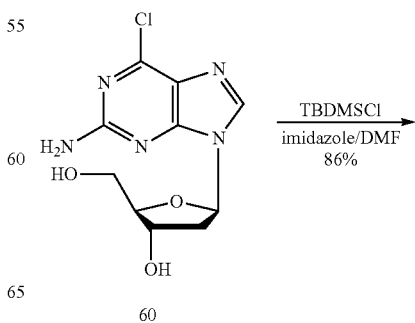

60

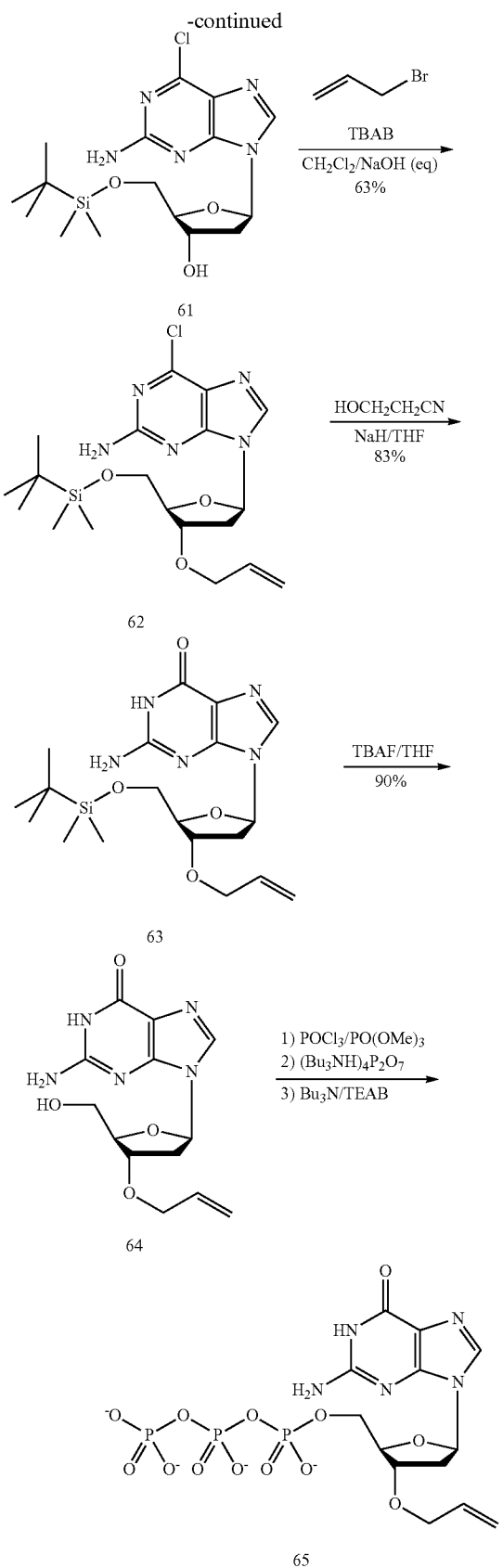

lar to the synthesis of 18, and the crude product was purified by flash column chromatography using $CH_3OH$—$CH_2Cl_2$ (1:20) as the eluent to afford 61 as white solid (1.20 g; 86% yield): $^1$H NMR (400 MHz, $CD_3OD$) δ 8.25 (s, 1H, 8-H), 6.34 (t, J=6.4 Hz, 1H, 1'-H), 4.56 (m, 1H, 3'-H), 4.01 (m, 1H, 4'-H), 3.90 (dd, J=3.5, 11.4 Hz, 1H, one of 5'-H), 3.84 (dd, J=3.8, 11.4 Hz, 1H, one of 5'-H), 2.67-2.74 (m, 1H, one of 2'-H), 2.43-2.50 (ddd, J=4.2, 6.4, 13.5 Hz, 1H, one of 2'-H), 0.89 (s, 9H, $C(CH_3)_3$), 0.07 (s, 3H, one of $SiCH_3$), 0.06 (s, 3H, one of $SiCH_2$); $^{13}$C NMR (100 MHz, $CD_3OD$) δ 161.1, 154.2, 151.2, 142.0, 124.9, 88.9, 85.5, 72.0, 64.3, 41.4, 26.5, 19.3, −5.1 (two $SiCH_3$); HRMS (FAB+) calcd for $C_{16}H_{27}O_3N_5ClSi$ (M+H$^+$): 400.1572. found: 400.1561.

2-Amino-6-chloro-9-[β-D-3'-O-allyl-5'-O-(tert-butyldimethylsilyl)-2'-deoxyribo-furanosyl]-purine (62). The procedure was the same as that of 35, and the crude product 61 converted from 60 was purified by flash column chromatography using ethyl acetate-hexane (1:2) as the eluent to afford 62 as white solid (832 mg; 63% yield): $^1$H NMR (400 MHz, $CD_3OD$) δ 8.23 (s, 1H, 8-H), 6.30 (t, J=6.7 Hz, 1H, 1'-H), 5.89-5.99 (m, 1H, $CH_2CH=CH_2$), 5.28-5.35 (dm, J=17.3 Hz, 1H, one of $CH_2CH=CH_2$), 5.16-5.21 (dm, J=10.5 Hz, 1H, one of $CH_2CH=CH_2$), 4.33 (m, 1H, 3'-H), 4.13 (m, 1H, 4'-H), 4.03-4.12 (m, 2H, $CH_2CH=CH_2$), 3.86 (dd, J=4.3, 11.2 Hz, 1H, one of 5'-H), 3.81 (dd, J=3.9, 11.2 Hz, 1H, one of 5'-H), 2.68-2.75 (m, 1H, one of 2'-H), 2.53-2.59 (ddd, J=3.2, 6.2, 13.6 Hz, 1H, one of 2'-H), 0.88 (s, 9H, $C(CH_3)_3$), 0.08 (s, 3H, one of $SiCH_3$), 0.07 (s, 3H, one of $SiCH_3$); $^{13}$C NMR (100 MHz, $CD_3OD$) δ 161.1, 154.2, 151.2, 141.9, 135.5, 124.9, 117.1, 86.7, 85.6, 80.0, 71.1, 64.5, 38.7, 26.5, 19.3, −5.1, −5.2; HRMS (FAB+) calcd for $C_{19}H_{31}O_3N_5ClSi$ (M+H$^+$): 440.1885. found: 440.1870.

3'-O-Allyl-5'-O-(tert-butyldimethylsilyl)-2'-deoxyguanosine (63). To a stirred suspension of 95% NaH power (223 mg; 8.83 mmol) in anhydrous THF (82 mL), 3-hydroxypropionitrile (550 μL; 8.00 mmol) was added and the mixture was stirred at room temperature for 20 min. Then 62 (832 mg; 1.89 mmol) in anhydrous THF (20 mL) was added and the mixture was stirred at 40° C. for 1 h. At room temperature, 80% acetic acid (630 μL; 8.83 mmol) was added and stirred for 20 min. After evaporation, ethyl acetate (100 mL) was added. The mixture was washed by saturated aqueous $NaHCO_3$, NaCl, and dried over anhydrous $Na_2SO_4$. After evaporation, the residue was purified by flash column chromatography using $CH_3OH$—$CH_2Cl_2$ (1:20) as the eluent to afford 63 as white solid (661 mg; 83% yield): $^1$H NMR (400 MHz, $CD_3OD$) δ 7.92 (s, 1H, 8-H), 6.22 (dd, J=6.4, 7.3 Hz, 1H, 1'-H), 5.89-5.99 (m, 1H, $CH_2CH=CH_2$), 5.29-5.35 (dm, J=17.3 Hz, 1H, one of $CH_2CH=CH_2$), 5.17-5.21 (dm, J=10.5 Hz, 1H, one of $CH_2CH=CH_2$), 4.30 (m, 1H, 3'-H), 4.11 (m, 1H, 4'-H), 4.03-4.12 (m, 2H, $CH_2CH=CH_2$), 3.79-3.86 (m, 2H, 5'-H), 2.56-2.64 (ddd, J=5.9, 7.4, 13.5 Hz, 1H, one of 2'-H), 2.49-2.55 (ddd, J=3.0, 6.1, 13.5 Hz, 1H, one of 2'-H), 0.91 (s, 9H, $C(CH_3)_3$), 0.10 (s, 3H, one of $SiCH_3$), 0.09 (s, 3H, one of $SiCH_2$); $^{13}$C NMR (100 MHz, $CDCl_3$) δ 158.7, 153.4, 151.0, 135.3, 134.1, 117.2, 117.1, 85.0, 83.8, 78.7, 70.2, 63.3, 38.2, 26.1, 18.5, −5.1, −5.3; HRMS (FAB+) calcd for $C_{19}H_{32}O_4N_5Si$ (M+H$^+$): 422.2224. found: 422.2209.

3'-O-Allyl-2'-deoxyguanosine (64). The procedure was similar to the synthesis of 20 and the crude product was purified by flash column chromatography using $CH_2OH$—$CH_2Cl_2$ (1:10) as the eluent to afford 64 as white solid (434 mg; 90% yield): $^1$H NMR (400 MHz, $CD_3OD$) δ 7.94 (s, 1H, 8-H), 6.22 (dd, J=5.9, 8.4 Hz, 1H, 1'-H), 5.90-6.00 (m, 1H, $CH_2CH=CH_2$), 5.29-5.36 (dm, J=17.2 Hz, 1H, one of $CH_2CH=CH_2$), 5.17-5.21 (dm, J=10.5 Hz, 1H, one of $CH_2CH=CH_2$), 4.31 (m, 1H, 3'-H), 4.14 (m, 1H, 4'-H), 4.03-

4.13 (m, 2H, CH$_2$CH=CH$_2$), 3.80 (dd, J=3.8, 12.0 Hz, 1H, one of 5'-H), 3.72 (dd, J=3.7, 12.0 Hz, 1H, one of 5'-H), 2.63-2.71 (ddd, J=5.9, 8.4, 13.6 Hz, 1H, one of 2'-H), 2.45-2.52 (ddd, J=2.1, 5.9, 13.6 Hz, 1H, one of 2'-H); $^{13}$C NMR (100 MHz, DMSO-d$_6$) δ 156.4, 153.4, 150.6, 135.1, 134.8, 116.5, 116.3, 84.9, 82.6, 79.1, 69.0, 61.8, 36.4; HRMS (FAB+) calcd for C$_{12}$H$_{15}$O$_4$N$_5$ (M+H$^+$): 308.1359. found: 308.1358.

3'-O-Allyl-2'-deoxyguanosine-5'-triphosphate (65). The procedure was similar to the synthesis of 51 to yield 65 as colorless syrup: $^1$H NMR (300 MHz, D$_2$O) δ 7.90 (s, 1H, 8-H), 6.21 (dd, J=6.1, 8.1 Hz, 1H, 1'-H), 5.86-5.96 (m, 1H, CH$_2$CH=CH$_2$), 5.27-5.35 (m, 1H, one of CH$_2$CH=CH$_2$), 5.15-5.20 (m, 1H, one of CH$_2$CH=CH$_2$), 4.30 (m, 1H, 3'-H), 4.15 (m, 1H, 4'-H), 4.02-4.14 (m, 2H, CH$_2$CH=CH$_2$), 3.75-3.85 (m, 2H, 5'-H), 2.60-2.73 (m, 1H, one of 2'-H), 2.42-2.50 (m, 1H, one of 2'-H); $^{31}$P NMR (121.4 MHz, D$_2$O) δ −10.9 (d, J=18.9 Hz, 1P, γ-P), −11.3 (d, J=19.6 Hz, 1P, α-P), −22.9 (t, J=19.6 Hz, 1P, β-P).

III. Construction of a Chip with Immobilized Self-Priming DNA Template

The DNA chip was constructed as shown in FIG. 5 and involved the following three steps:

Synthesis of the alkyne-functionalized DNA template. The 5'-amino-hairpin DNA templates (GeneLink, NY) 5'-NH$_2$-TTT-TTG-TTT-TTT-TTT-TCG-ATC-GAC-TTA-AGG-CGC-TTG-CGC-CTT-AAG-TCG-3' (SEQ ID NO:3) and 5'-NH$_2$-AGT-CAG-TCT-CTC-ATC-TCG-ACA-TCT-ACG-CTA-CTC-GTC-GAT-CGG-AAA-CAG-CTA-TGA-CCA-TGC-TTG-CAT-GGT-CAT-AGC-TGT-TTC-C-3' (SEQ ID NO:4) were coupled with 6-heptynoic acid by adding 300 μL DMSO solution of 6-heptynoic-NHS ester [succinimidyl N-(6-heptynoate)] (0.8 M) into the 1000 μL DNA template solution (200 μM, in 0.25 M Na$_2$CO$_3$/NaHCO$_3$ buffer, pH 9.0).

Azide functionalization of an amine-modified glass surface. The amine-modified glass slide (Corning® GAPS II) was cleaned and pre-treated by immersion into a basic solution [N,N-diisopropyl ethylamine (DIPEA)/dimethylformamide (DMF), 1:9 (V/V)] for 30 min. The glass slide was then washed with DMF, and transferred into the 2 mL DMF coupling solution containing 100 mM 0-(2-azidoethyl)-0'-[2-(diglycolyl-amino)-ethyl]heptaethylene glycol (Fluke, Switzerland), Benzotriazole-1-yl-oxy-tris-pyrrolidino-phosphonium hexafluorophosphate (PyBOP) (Novabiochem, CA) and 200 mM DIPEA. The reaction vessel was gently shaken for 4 h at room temperature. The azide functionalized glass slide was washed thoroughly with DMF and ethanol, and then dried under argon gas stream.

DNA immobilization on the azide-modified glass surface using 1,3-dipolar alkyne-azide cycloaddition chemistry.

A coupling mixture was prepared by mixing tetrakis-(acetonitrile)copper (I) hexafluorophosphate (2 mM/DMSO), tris-(benzyltriazolylmethyl) amine (TBTA) (2 mM/DMSO), sodium ascorbate (2.6 mM/H$_2$O) and alkynyl DNA (50 μM/H$_2$O) with a volumetric ratio of 3:3:2.3:3. This coupling mixture was then spotted onto the azide-functionalized glass slide in the form of 11.0 μL drops with the aid of adhesive silicone isolators (Grace Bio-Labs, OR) to create uniform spots on the glass surface. The DNA spotted glass slide was incubated in a humid chamber at room temperature for 8 h, then washed with de-ionized water and SPSC buffer (50 mM sodium phosphate/1 M NaCl, pH 7.5) for ½ h to remove non-specifically bound DNA, and finally rinsed with dH$_2$O. The formation of a stable hairpin was ascertained by covering the DNA spots with 1× Thermolpol II reaction buffer (10 mM KCl, 10 mM (NH$_4$)$_2$SO$_4$, 20 mM Tris-HCl, 0.1% Triton X-100, 4 mM MnCl$_2$, pH 8.8), incubating it in a humid chamber at 95° C. for 5 min to dissociate any partial hairpin structure, and then cooling slowly for re-annealing.

IV. Continuous DNA Polymerase Reaction Using Four Chemically Cleavable Fluorescent Nucleotides as Reversible Terminators in Solution We characterized the four nucleotide analogues 3'-O-allyl-dCTP-allyl-Bodipy-FL-510, 3'-O-allyl-dUTP-allyl-R6G, 3'-O-allyl-dATP-allyl-ROX and 3'-O-allyl-dGTP-allyl-Bodipy-650, by performing four continuous DNA-extension reactions sequentially using a primer (5'-AGAGGATC-CAACCGAGAC-3', SEQ ID NO:5) and a synthetic DNA template (5'-GTGTACATCAACATCACCTACCACCAT-GTCAGTCTCGGTTGGATCCTCTATTGTGTCCGG-3', SEQ ID NO:6) based on a portion of exon 7 of the human p53 gene.

The four nucleotides in the template immediately adjacent to the annealing site of the primer are 3'-ACTG-5'. First, a polymerase extension reaction using a pool of all four nucleotide analogues along with the primer and the template was performed producing a single base extension product. The reaction mixture for this, and all subsequent extension reactions, consisted of 80 pmol of template, 50 pmol of primer, 100 pmol of 3'-O-allyl-dNTPs-allyl-fluorophore, 1× Thermopol II reaction buffer, 40 nmol of Mn$^{2+}$ and 2 U of 9° N mutant DNA polymerase (exo-) A485L/Y409V in a total volume of 20 μL. The reaction consisted of 20 cycles at 94° C. for 20 sec, 48° C. for 40 sec, and 62° C. for 90 sec. Subsequently, the extension product was purified by using reverse-phase HPLC. The fraction containing the desired DNA product was collected and freeze-dried for analysis using MALDI-TOF mass spectrometry. For deallylation, the purified DNA extension product bearing the fluorescent nucleotide analogue was resuspended in degassed water and added to a deallylation cocktail [1× Thermopol I reaction buffer/ Na$_2$PdCl$_4$/P(PhSO$_2$Na)$_3$] and incubated for 30 s to yield deallylated DNA product which was characterized by MALDI-TOF MS. The DNA product with both the fluorophore and the 3'-O-allyl group removed to generate a free 3'-OH group was used as a primer for a second extension reaction using 3'-O-allyl-dNTPs-allyl-fluorophore. The second extended DNA product was then purified by HPLC and deallylated.

The third and the fourth extensions were carried out in a similar manner using the previously extended and deallylated product as the primer.

V. 4-Color SBS Reaction on a Chip with Four Chemically Cleavable Fluorescent Nucleotides as Reversible Terminators Ten microliters of a solution consisting of 3'-O-allyl-dCTP-allyl-Bodipy-FL-510 (3 pmol), 3'-O-allyl-dUTP-allyl-R6G (10 pmol), 3'-O-allyl-dATP-allyl-ROX (5 pmol) and 3'-O-allyl-dGTP-allyl-Cy5 (2 pmol), 1 U of 9° N mutant DNA polymerase, and 1× Thermolpol II reaction buffer was spotted on the surface of the chip, where the self-primed DNA moiety was immobilized. The nucleotide analogue complementary to the DNA template was allowed to incorporate into the primer at 68° C. for 10 min. To synchronize any unincorporated templates, an extension solution consisting of 30 pmol each of 3'-O-allyl-dCTP, 3'-O-allyl-dTTP, 3'-O-allyl-dATP and 3'-O-allyl-dGTP, 1 U of 9° N mutant DNA polymerase, and 1× Thermolpol II reaction buffer was spotted on the same spot and incubated at 68° C. for 10 min. After washing the chip with a SPSC buffer containing 0.1% Tween 20 for 5 min, the surface was rinsed with dH$_2$O, dried briefly and then scanned with a 4-color ScanArray Express scanner (Perkin-Elmer Life Sciences) to detect the fluorescence signal. The 4-color scanner is equipped with four lasers with excitation wavelengths of 488, 543, 594, and 633 nm and emission filters centered at 522, 570, 614, and 670 nm. For deallylation, the chip was immersed in a deallylation cocktail [1× Thermolpol I reaction buffer/Na$_2$PdCl$_4$/P(PhSO$_3$Na)$_3$] and incubated for 5 min at 60° C. The chip was then immediately immersed in a 3 M Tris-HCl buffer (pH 8.5) and incubated for 5 min at 60° C. Finally, the chip was rinsed with acetonitrile/dH$_2$O (1:1, V/V) and dH$_2$O. The chip surface was scanned again to compare the intensity of fluorescence after deallylation with the original fluorescence intensity. This process was followed by the next polymerase extension reaction using 3'-O-allyl-dNTPs-allyl-fluorophore and 3'-O-allyl-dNTPs, with the subsequent washing, fluorescence detection, and deallylation processes performed as described above. The same cycle was repeated multiple times using the four chemically cleavable fluorescent nucleotide mixture in polymerase extension reaction to obtain de novo DNA sequencing data on various different DNA templates.

REFERENCES

1. Collins, F. S., Green, E. D., Guttmacher, A. E. & Guyer, M. S. (2003) *Nature* 422, 835-847.
2. Smith, L. M., Sanders, J. Z., Kaiser, R. J., Hughes, P., Dodd, C., Connell, C. R., Heiner, C., Kent, S. B. & Hood, L. E. (1986) *Nature* 321, 674-679.
3. Prober, J. M., Trainor, G. L., Dam, R. J., Hobbs, F. W., Robertson, C. W., Zagursky, R. J., Cocuzza, A. J., Jensen, M. A. & Baumeister, K. (1987) *Science* 238, 336-341.
4. Ju, J., Ruan, C., Fuller, C. W., Glazer, A. N. & Mathies, R. A. (1995) *Proc. Natl. Acad. Sci. USA* 92, 4347-4351.
5. Kan, C. W., Doherty, E. A. & Barron, A. E. (2003) *Electrophoresis* 24, 4161-4169.
6. Drmanac, S., Kita, D., Labat, I., Hauser, B., Schmidt, C., Burczak, J. D. & Drmanac, R. (1998) *Nat. Biotechnol.* 16, 54-58.
7. Fu, D. J., Tang, K., Braun, A., Reuter, D., Darnhofer-Demar, B., Little, D. P., O'Donnell, M. J., Cantor, C. R. & Koster, H. (1998) *Nat. Biotechnol.* 16, 381-384.
8. Roskey, M. T., Juhasz, P., Smirnov, I. P., Takach, E. J., Martin, S. A. & Haff, L. A. (1996) *Proc. Natl. Acad. Sci. USA* 93, 4724-4729.
9. Edwards, J. R., Itagaki, Y. & Ju, J. (2001) *Nucleic Acids Res.* 29, E104-4.
10. Kasianowicz, J. J., Brandin, E., Branton, D. & Deamer, D. W. (1996) *Proc. Natl. Acad. Sci. USA* 93, 13770-13773.
11. Shendure, J., Porreca, G. J., Reppas, N. B., Lin, X., McCutcheon, J. P., Rosenbaum, A. M., Wang, M. D., Zhang, K., Mitra, R. D. & Church, G. M. (2005) *Science* 309, 1728-1732.
12. Ronaghi, M., Uhlen, M. & Nyren, P. (1998) *Science* 281, 363-365.
13. Braslaysky, I., Hebert, B., Kartalov, E. & Quake, S. R. (2003) *Proc. Natl. Acad. Sci. USA* 100, 3960-3964.
14. Mitra, R. D., Shendure, J., Olejnik, J., Edyta Krzymanska, O. & Church, G. M. (2003) *Anal. Biochem.* 320, 55-65.
15. Hyman, E. D. (1988) *Anal. Biochem.* 174, 423-436.
16. Margulies, M., Egholm, M., Altman, W. E., Attiya, S., Bader, J. S., Bemben, L. A., Berka, J., Braverman, M. S., Chen, Y.-J., Chen, Z., et. al. (2005) *Nature* 437, 376-380.
17. Cheeseman, P. C. (1994) U.S. Pat. No. 5,302,509.
18. Metzker, M. L., Raghavachari, R., Richards, S., Jacutin, S. E., Civitello, A., Burgess, K. & Gibbs, R. A. (1994) *Nucleic Acids Res.* 22, 4259-4267.
19. Welch, M. B. & Burgess, K. (1999) *Nucleosides Nucleotides* 18, 197-201.
20. Lu, G. & Burgess, K. (2006) *Bioorg. Med. Chem. Lett.* 16, 3902-3905.
21. Metzker, M. L. (2005) *Genome Res.* 15, 1767-1776.
22. Pelletier, H., Sawaya, M. R., Kumar, A., Wilson, S. H. & Kraut, J. (1994) *Science* 264, 1891-1903.
23. Rosenblum, B. B., Lee, L. G., Spurgeon, S. L., Khan, S. H., Menchen, S. M., Heiner, C. R. & Chen, S. M. (1997) *Nucleic Acids Res.* 25, 4500-4504.
24. Zhu, Z., Chao, J., Yu, H. & Waggoner, A. S. (1994) *Nucleic Acids Res.* 22, 3418-3422.
25. Ju, J., Li, Z., Edwards, J. & Itagaki, Y. (2003) U.S. Pat. No. 6,664,079.
26. Seo, T. S., Bai, X., Kim, D. H., Meng, Q., Shi, S., Ruparel, H., Li, Z., Turro, N. J. & Ju, J. (2005) *Proc. Natl. Acad. Sci. USA* 102, 5926-31.
27. Bi, L., Kim, D. H. & Ju, J. (2006) *J. Am. Chem. Soc.* 128, 2542-2543.
28. Ruparel, H., Si, L., Li, Z., Bai, X., Kim, D. H., Turro, N. J. & Ju, J. (2005) *Proc. Natl. Acad. Sci. USA* 102, 5932-5937.
29. Meng, Q., Kim, D. H., Bai, X., Si, L., Turro, N. J. & Ju, J. (2006) *J. Org. Chem.* 71, 3248-3252.
30. Barnes, C., Balasubramanian, S., Liu, X., Swerdlow, H., Milton, J. (2006) U.S. Pat. No. 7,057,026.

What is claimed is:

1. A method for determining the sequence of a DNA comprising performing the following steps for each residue of the DNA to be sequenced:

(a) contacting the DNA with a DNA polymerase in the presence of (i) a primer and (ii) four nucleotide analogues under conditions permitting the DNA polymerase to catalyze DNA synthesis, wherein (1) the nucleotide analogues consist of an analogue of dGTP, an analogue of dCTP, an analogue of dTTP or dUTP, and an analogue of dATP, (2) each nucleotide analogue comprises (i) a base selected from the group consisting of adenine, guanine, cytosine, thymine or uracil, and analogues thereof, (ii) a deoxyribose, (iii) a moiety cleavably linked to the 3'-oxygen of the deoxyribose and (iv) a unique label cleavably linked to the base, so that a nucleotide analogue complementary to the residue being sequenced is incorporated into the DNA by the DNA polymerase, and (3) each of the four analogues has a unique label which is different than the unique labels of the other three analogues;

(b) removing unbound nucleotide analogues;

(c) again contacting the DNA with a DNA polymerase in the presence of (i) a primer and (ii) four reversible terminators under conditions permitting the DNA polymerase to catalyze DNA synthesis, wherein (1) the reversible terminators consist of an analogue of dGTP, an analogue of dCTP, an analogue of dTTP or dUTP, and an analogue of dATP, (2) each nucleotide analogue comprises (i) a base selected from the group consisting of adenine, guanine, cytosine, thymine or uracil, and analogues thereof, which base does not have a unique label bound thereto, (ii) a deoxyribose, and (iii) a moiety cleavably linked to the 3'-oxygen of the deoxyribose;
(d) removing unbound reversible terminators;
(e) determining the identity of the nucleotide analogue incorporated in step (a) via determining the identity of the corresponding unique label, with the proviso that step (e) can either precede step (c) or follow step (d); and
(f) following step (e), except with respect to the final DNA residue to be sequenced, cleaving from the incorporated nucleotide analogues the unique label, if applicable, and the moiety linked to the 3'-oxygen atom of the deoxyribose, thereby determining the sequence of the DNA.

2. The method of claim 1, wherein step (e) is performed before step (c).

3. The method of claim 1, wherein the moiety cleavably linked to the 3'-oxygen of the deoxyribose is chemically cleavable or photocleavable.

4. The method of claim 1, wherein the unique label is bound to the base via a chemically cleavable or photocleavable linker.

5. The method of claim 1, wherein the unique label bound to the base via a cleavable linker is a dye, a fluorophore, a chromophore, a combinatorial fluorescence energy transfer tag, a mass tag, or an electrophore.

6. The method of claim 1, wherein the primer is a self-priming moiety.

7. The method of claim 1, wherein the DNA is bound to a solid substrate.

8. The method of claim 7, wherein the DNA is bound to the solid substrate via 1,3-dipolar azide-alkyne cycloaddition chemistry.

9. The method of claim 7, wherein the DNA is alkyne-labeled.

10. The method of claim 7, wherein the DNA is bound to the solid substrate via a polyethylene glycol molecule and the solid substrate is azide-functionalized.

11. The method of claim 7, wherein the DNA is immobilized on the solid substrate via an azido linkage, an alkynyl linkage, or biotin-streptavidin interaction.

12. The method of claim 7, wherein the solid substrate is in the form of a chip, a bead, a well, a capillary tube, a slide, a wafer, a filter, a fiber, a porous media, or a column.

13. The method of claim 7, wherein the solid substrate is gold, quartz, silica, plastic, glass, diamond, silver, metal, or polypropylene.

14. The method of claim 7, wherein the solid substrate is porous.

15. A kit for performing the method of claim 1, comprising, in separate compartments,
(a) nucleotide analogues of (i) GTP, (ii) ATP, (iii) CTP and (iv) TTP or UTP, wherein each analogue comprises (i) a base selected from the group consisting of adenine, guanine, cytosine, thymine or uracil, or an analogue thereof, (ii) a deoxyribose, (iii) a cleavable moiety bound to the 3'-oxygen of the deoxyribose and (iv) a unique label bound to the base via a cleavable linker,
(b) reversible terminators comprising a nucleotide analogue of (i) GTP, (ii) ATP, (iii) CTP and (iv) TTP or UTP, wherein each analogue comprises (i) a base selected from the group consisting of adenine, guanine, cytosine, thymine or uracil, or an analogue thereof, which base does not have a unique label bound thereto, (ii) a deoxyribose, and (iii) a cleavable moiety bound to the 3'-oxygen of the deoxyribose;
(c) reagents suitable for use in DNA polymerization; and
(d) instructions for use.

16. The kit of claim 15, wherein the nucleotide analogues of part (a) are 3'-O-allyl-dGTP-allyl-Cy5, 3'-O-allyl-dCTP-allyl-Bodipy-FL-510, 3'-O-allyl-dATP-allyl-ROX and 3'-O-allyl-dUTP-allyl-R6G.

17. The kit of claim 15, wherein the nucleotide analogues of part (a) are 3'-O-allyl-dGTP-allyl-Bodipy-FL-510, 3'-O-allyl-dCTP-allyl-Bodipy-650, 3'-O-allyl-dATP-allyl-ROX and 3'-O-allyl-dUTP-allyl-R6G.

18. The kit of claim 15, wherein the nucleotide analogues of part (a) are 3'-O-allyl-dGTP-allyl-Bodipy-650, 3'-O-allyl-dCTP-allyl-Bodipy-FL-510, 3'-O-allyl-dATP-allyl-ROX and 3'-O-allyl-dUTP-allyl-R6G.

19. The kit of claim 15, wherein the nucleotide analogues of part (b) are 3'-O-allyl-dGTP, 3'-O-allyl-dCTP, 3'-O-allyl-dATP and 3'-O-allyl-dUTP.

20. The method of claim 15, wherein the reversible terminators in step (c) are 3'-O-2-nitrobenzyl-dGTP, 3'-O-2-nitrobenzyl-dCTP, 3'-O-2-nitrobenzyl-dATP and 3'-O-2-nitrobenzyl-dUTP.

* * * * *